(12) United States Patent
Bamdad

(10) Patent No.: US 12,195,728 B2
(45) Date of Patent: Jan. 14, 2025

(54) METHOD FOR MAKING PLURIPOTENT STEM CELLS

(71) Applicant: Minerva Biotechnologies Corporation, Waltham, MA (US)

(72) Inventor: Cynthia Bamdad, Boston, MA (US)

(73) Assignee: MINERVA BIOTECHNOLOGIES CORPORATION, Waltham, MA (US)

(*) Notice: Subject to any disclaimer, the term of this patent is extended or adjusted under 35 U.S.C. 154(b) by 0 days.

(21) Appl. No.: 18/742,215

(22) Filed: Jun. 13, 2024

(65) Prior Publication Data

US 2024/0368578 A1    Nov. 7, 2024

Related U.S. Application Data

(60) Continuation of application No. 16/912,135, filed on Jun. 25, 2020, now Pat. No. 12,049,618, which is a division of application No. 14/029,651, filed on Sep. 17, 2013, now Pat. No. 10,724,027, which is a continuation of application No. PCT/US2012/029706, filed on Mar. 19, 2012.

(60) Provisional application No. 61/474,236, filed on Apr. 11, 2011, provisional application No. 61/472,516, filed on Apr. 6, 2011, provisional application No. 61/453,917, filed on Mar. 17, 2011.

(51) Int. Cl.
| | |
|---|---|
| C07K 16/00 | (2006.01) |
| A61K 31/7088 | (2006.01) |
| C07K 16/28 | (2006.01) |
| C07K 16/30 | (2006.01) |
| C12N 5/0735 | (2010.01) |
| C12N 5/074 | (2010.01) |
| C12N 11/06 | (2006.01) |
| C12Q 1/6881 | (2018.01) |

(52) U.S. Cl.
CPC .......... *C12N 11/06* (2013.01); *A61K 31/7088* (2013.01); *C07K 16/2863* (2013.01); *C07K 16/3092* (2013.01); *C12N 5/0606* (2013.01); *C12N 5/0696* (2013.01); *C12Q 1/6881* (2013.01); *C07K 2317/35* (2013.01); *C07K 2317/75* (2013.01); *C12N 2500/98* (2013.01); *C12N 2501/115* (2013.01); *C12N 2501/727* (2013.01); *C12N 2533/50* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 4,675,189 A | 6/1987 | Kent et al. | |
| 4,816,567 A | 3/1989 | Cabilly et al. | |
| 5,075,109 A | 12/1991 | Tice et al. | |
| 5,133,974 A | 7/1992 | Paradissis et al. | |
| 5,225,539 A | 7/1993 | Winter | |
| 5,407,686 A | 4/1995 | Patel et al. | |
| 5,585,089 A | 12/1996 | Queen et al. | |
| 5,693,762 A | 12/1997 | Queen et al. | |
| 5,736,152 A | 4/1998 | Dunn | |
| 5,834,217 A | 11/1998 | Levine et al. | |
| 5,859,205 A | 1/1999 | Adair et al. | |
| 6,087,117 A | 7/2000 | King et al. | |
| 6,617,135 B1 | 9/2003 | Gillies et al. | |
| 7,129,058 B2 | 10/2006 | Yamashita | |
| 7,700,715 B2 | 4/2010 | Bamdad et al. | |
| 8,535,944 B2 | 9/2013 | Bamdad | |
| 8,859,495 B2 | 10/2014 | Bamdad | |
| 9,334,331 B2 | 5/2016 | Igawa et al. | |
| 10,421,807 B2 | 9/2019 | Gonzales et al. | |
| 10,703,821 B2 | 7/2020 | Bamdad | |
| 10,724,027 B2 | 7/2020 | Bamdad | |
| 11,591,565 B2 | 2/2023 | Bamdad et al. | |
| 11,898,160 B2 | 2/2024 | Bamdad et al. | |
| 11,976,295 B2 | 5/2024 | Bamdad et al. | |
| 12,049,618 B2 | 7/2024 | Bamdad | |
| 2002/0119568 A1 | 8/2002 | Berenson et al. | |
| 2002/0142964 A1 | 10/2002 | Nissen et al. | |
| 2002/0156112 A1 | 10/2002 | Bamdad et al. | |
| 2002/0169290 A1 | 11/2002 | Bornaes et al. | |
| 2003/0036199 A1 | 2/2003 | Bamdad et al. | |
| 2004/0002119 A1 | 1/2004 | Iannone et al. | |
| 2004/0009147 A1 | 1/2004 | Ebner et al. | |
| 2004/0067585 A1 | 4/2004 | Wang et al. | |
| 2004/0137513 A1 | 7/2004 | Devaux et al. | |
| 2004/0180823 A1 | 9/2004 | Pasquale et al. | |
| 2004/0192898 A1 | 9/2004 | Jia et al. | |
| 2005/0054752 A1 | 3/2005 | O'Brien et al. | |

(Continued)

FOREIGN PATENT DOCUMENTS

| | | |
|---|---|---|
| CN | 101273060 A | 9/2008 |
| EP | 0239400 A2 | 9/1987 |

(Continued)

OTHER PUBLICATIONS

Alberts et al. Cell Biology: The Endless Frontier. Mol Biol Cell 21:129-130 (1994).

Al-Hajj et al. Prospective identification of tumorigenic breast cancer cells. PNAS 100(7):3983-3988 (2003).

Al-Hajj et al. Self-renewal and solid tumor stem cells. Oncogene, 23:7274-7282 (2004).

Allsopp et al. Comparison of numerous delivery systems for the induction of cytotoxic T lymphocytes by immunization. Eur. J. Immunol 26:1951-1959 (1996).

Altschul, Stephen F. et al. Gapped Blast and PSI-Blast: A New Generation of Protein Database Search Programs. Nucleic Acids Research 25(17):3389-3402 (1997).

(Continued)

*Primary Examiner* — Michail A Belyavskyi
(74) *Attorney, Agent, or Firm* — WILSON SONSINI GOODRICH & ROSATI

(57) ABSTRACT

The present application discloses a method for inducing cells to gain characteristics of naïve stem cell state comprising culturing the cells in the presence of a MUC1* activator.

6 Claims, 44 Drawing Sheets

Specification includes a Sequence Listing.

(56) References Cited

U.S. PATENT DOCUMENTS

| | | |
|---|---|---|
| 2005/0112607 A1 | 5/2005 | Bamdad et al. |
| 2006/0173171 A1 | 8/2006 | Bamdad |
| 2006/0222637 A1 | 10/2006 | Bamdad |
| 2006/0228357 A1 | 10/2006 | Chang et al. |
| 2006/0252087 A1 | 11/2006 | Tang et al. |
| 2007/0009918 A1 | 1/2007 | Glimcher et al. |
| 2007/0134713 A1 | 6/2007 | Cao |
| 2007/0243171 A1 | 10/2007 | Bunce |
| 2007/0264306 A1 | 11/2007 | Flameng et al. |
| 2008/0044424 A1 | 2/2008 | Cohen et al. |
| 2008/0233601 A1 | 9/2008 | Ippoliti et al. |
| 2008/0306006 A1 | 12/2008 | Croce et al. |
| 2009/0075926 A1 | 3/2009 | Bamdad |
| 2009/0142790 A1 | 6/2009 | Fang et al. |
| 2009/0148535 A1 | 6/2009 | Bamdad |
| 2009/0175867 A1 | 7/2009 | Thompson et al. |
| 2009/0191171 A1 | 7/2009 | Ma |
| 2009/0306035 A1 | 12/2009 | Peng et al. |
| 2010/0003674 A1 | 1/2010 | Cope et al. |
| 2010/0055678 A1 | 3/2010 | Jaatinen et al. |
| 2010/0173359 A1 | 7/2010 | Ladine et al. |
| 2010/0184032 A1 | 7/2010 | Georgantas et al. |
| 2010/0278788 A1 | 11/2010 | Badoer et al. |
| 2010/0285014 A1 | 11/2010 | Cox, III et al. |
| 2010/0311955 A1 | 12/2010 | Guo et al. |
| 2010/0316688 A1 | 12/2010 | Bamdad |
| 2011/0009469 A1 | 1/2011 | Mendell et al. |
| 2011/0014164 A1 | 1/2011 | Huangfu et al. |
| 2012/0115225 A1 | 5/2012 | Xu |
| 2012/0128655 A1 | 5/2012 | Kim et al. |
| 2012/0156246 A1 | 6/2012 | Bamdad |
| 2014/0044696 A1 | 2/2014 | Bamdad |
| 2014/0065113 A1 | 3/2014 | Bamdad et al. |
| 2015/0017726 A1 | 1/2015 | Bamdad et al. |
| 2015/0203823 A1 | 7/2015 | Bamdad |
| 2015/0320840 A1 | 11/2015 | Bamdad |
| 2020/0062812 A1 | 2/2020 | Bamdad et al. |
| 2020/0385485 A1 | 12/2020 | Bamdad |
| 2021/0054358 A1 | 2/2021 | Bamdad |
| 2022/0252604 A1 | 8/2022 | Bamdad |
| 2023/0049461 A1 | 2/2023 | Bamdad |
| 2024/0247229 A1 | 7/2024 | Bamdad et al. |
| 2024/0294590 A1 | 9/2024 | Bamdad et al. |

FOREIGN PATENT DOCUMENTS

| | | |
|---|---|---|
| JP | 2008543276 A | 12/2008 |
| JP | 2009539413 A | 11/2009 |
| WO | WO-8809344 A1 | 12/1988 |
| WO | WO-8909622 A1 | 10/1989 |
| WO | WO-9007861 A1 | 7/1990 |
| WO | WO-9110741 A1 | 7/1991 |
| WO | WO-9402602 A1 | 2/1994 |
| WO | WO-9524929 A2 | 9/1995 |
| WO | WO-9600782 A1 | 1/1996 |
| WO | WO-9633735 A1 | 10/1996 |
| WO | WO-9634096 A1 | 10/1996 |
| WO | WO-0034783 A1 | 6/2000 |
| WO | WO-0043791 A2 | 7/2000 |
| WO | WO-0236626 A1 | 5/2002 |
| WO | WO-02056022 A2 | 7/2002 |
| WO | WO-02077199 A2 | 10/2002 |
| WO | WO-03074074 A1 | 9/2003 |
| WO | WO-03106495 A2 | 12/2003 |
| WO | WO-03106618 A2 | 12/2003 |
| WO | WO-2004002259 A2 | 1/2004 |
| WO | WO-2004022590 A2 | 3/2004 |
| WO | WO-2005000899 A2 | 1/2005 |
| WO | WO-2005017148 A1 | 2/2005 |
| WO | WO-2005019269 A2 | 3/2005 |
| WO | WO-2005056780 A2 | 6/2005 |
| WO | WO-2005073383 A2 | 8/2005 |
| WO | WO-2006105448 A2 | 10/2006 |
| WO | WO-2007053135 A1 | 5/2007 |
| WO | WO-2007081740 A2 | 7/2007 |
| WO | WO-2008035110 A1 | 3/2008 |
| WO | WO-2008067065 A2 | 6/2008 |
| WO | WO-2008070171 A2 | 6/2008 |
| WO | WO-2009042814 A1 | 4/2009 |
| WO | WO-2009097136 A1 | 8/2009 |
| WO | WO-2009105570 A2 | 8/2009 |
| WO | WO-2009123349 A1 | 10/2009 |
| WO | WO-2009149233 A1 | 12/2009 |
| WO | WO-2009149956 A2 | 12/2009 |
| WO | WO-2009152084 A2 | 12/2009 |
| WO | WO-2009103969 A8 | 1/2010 |
| WO | WO-2010003118 A1 | 1/2010 |
| WO | WO-2010017510 A1 | 2/2010 |
| WO | WO-2010036939 A2 | 4/2010 |
| WO | WO-2010042562 A2 | 4/2010 |
| WO | WO-2010042891 A2 | 4/2010 |
| WO | WO-2010042981 A1 | 4/2010 |
| WO | WO-2010048567 A1 | 4/2010 |
| WO | WO-2010056737 A2 | 5/2010 |
| WO | WO-2010144887 A1 | 12/2010 |
| WO | WO-2011058558 A2 | 5/2011 |
| WO | WO-2011103049 A2 | 8/2011 |
| WO | WO-2011159960 A2 | 12/2011 |
| WO | WO-2012008302 A1 | 1/2012 |
| WO | WO-2012051515 A2 | 4/2012 |
| WO | WO-2012126013 A2 | 9/2012 |
| WO | WO-2012154759 A2 | 11/2012 |
| WO | WO-2013059373 A2 | 4/2013 |
| WO | WO-2014012115 A2 | 1/2014 |
| WO | WO-2014018679 A2 | 1/2014 |

OTHER PUBLICATIONS

Andrews et al. Comparative Analysis of Cell Surface Antigens Expressed by Cell Lines Derived From Human Germ Cell Tumors. Int J Cancer 66:806-816 (1996).

Aoi et al. Generation of pluripotent stem cells from adult mouse liver and stomach cells. Science 321:699-702 (2008).

Arndt et al. Characterization of global microRNA expression reveals oncogenic potential of miR-145 In metastatic colorectal cancer. BMC Cancer 9(374)1-17 (2009).

Bader et al. The Promise of MicroRNA Replacement Therapy. Cancer Res 70(18):7027-7030 (2010).

Bamdad, Cynthia. The Use of Variable Density Self-Assembled Monolayers to Probe the Structure of a Target Molecule. Biophysical Journal vol. 75,4: pp. 1989-1996 (1998).

Barratt-Boyes et al. Immunization of chimpanzees with tumor antigen MUC1 mucin tandem repeat peptide elicits both helper and cytotoxic T-cell responses. Clinical Cancer Research 5:1918-1924 (1999).

Bilitou et al. The NM23 family in development. Mol Cell Biochem 329(1-2):17-33 (2009).

Bonnet et al. Human acute myeloid leukemia is organized as a hierarchy that originates from a primitive hematopoietic cell. Nat. Med. 3:730-737 (1997).

Boyer, Laurie A et al. Core Transcriptional Regulatory Circuitry in Human Embryonic Stem Cells. Cell vol. 122,6: pp. 947-956 (2005).

Briasoulis et al. G-CSF induces elevation of circulating CA 15-3 in breast carcinoma patients treated in an adjuvant setting. Cancer 91:909-917 (2001).

Burchell et al. Development and characterization of breast cancer reactive monoclonal antibodies directed to the core protein of the human milk mucin. Cancer Res., 47:5476-5482 (1987).

Burdon et al. Suppression of SHP-2 and ERK signalling promotes self-renewal of mouse embryonic stem cells. Dev Biol 210(1):30-43 (1999).

Byrd et al. Mucins and mucin binding proteins in colorectal cancer. Cancer Metastasis Review 23(1-2):77-99 (2004).

Calin et al. MicroRNA signatures in human cancers. Nat. Rev. Cancer 6(11):857-866, 2006.

Campbell et al. Oct4 targets regulatory nodes to modulate stem cell function. PLoS One 2(6):e553 (2007).

Cao et al. Construction and characterization of an enhanced GFP-tagged anti-BAFF scFv antibody. Appl Microbiol Biotechnol. 79(3):423-31 (2008).

(56) References Cited

OTHER PUBLICATIONS

Cao et al. Evolutionary Emergence of microRNAs in Human Embryonic Stem Cells. PLoS One 3(7):e2820.
Chengalvala et al. Replication and immunogenicity of Ad7-, Ad4-, and Ad5-hepatitis B virus surface antigen recombinants, with or without a portion of E3 region, in chimpanzees. Vaccine 15:335-339 (1997).
Ciafre et al. Extensive modulation of a set of MicroRNAs in primary glioblastoma. Biochem Biophys Res Commun. 334(4): 1351-1358 (2005).
Clarke. Isolation and Characterization of Human Mammary Stem Cells. Cell Prolif. 38:375-386 (2005).
Cloosen et al. Mucin-1 is expressed on dendritic cells, both in vitro and in vivo. Int. Immunol. 11:1561-71 (2004).
Corsten et al. Therapeutic stem-cells for cancer treatment: hopes and hurdles in tactical warfare. Cytotechncology 9:376-84 (2008).
Dahiyat et al.: De novo protein design: fully automated sequence selection. Science 278(5335):82-87 (1997).
Davis et al. A viral vaccine vector that expresses foreign genes in lymph nodes and protects against mucosal challenge. J. Virol. 70:3781-3787 (1996).
Dellatore et al. Mimicking stem cell niches to increase stem cell expansion. Curr Opin Biotechnol 19(5):534-540 (Oct. 1, 2008).
Dexheimer, Thomas S et al. NM23-H2 May Play an Indirect Role in Transcriptional Activation of c-myc Gene Expression But Does Not Cleave The Nuclease Hypersensitive Element III(1). Molecular Cancer Therapeutics vol. 5,5: pp. 1363-1377 (2009).
Dubreuil-Lemaire et al. Lenograstim for the treatment of neutropenia in patients receiving ganciclovir for cytomegalovirus infection: a randomised, placebo-controlled trial in AIDS patients. Eur J Haematol 65:337-343 (2000).
Edwards, et al. The Remarkable Flexibility of the Human Antibody Repertoire; Isolation of Over One Thousand Different Antibodies to a Single Protein, BLyS. Journal of Molecular Biology 334(1):103-118 (2003).
Eloit et al. High level of transgene expression in cell cultures and in the mouse by replication-incompetent adenoviruses harboring modified VAI genes. J. Virol. 7:5375-5381 (1997).
Entry for "Pluripotent cell" from Append B: Glossary in 2008 Amendments to the National Academies' Guidelines for Human Embryonic Stem Cell Research. Natl. Res. Counc. and Inst. of Med. Human Embryonic Stem Cell Research Advisor Committee. Washington (DC): National Academies Press (2008).
Eridani et al. Siem cells: From embryology to cellular therapy? An appraisal of the present state of art. Cytotechnology 44:125-41 (2004).
Fessler et al. MUC1 is a determinant of trastuzumab (Herceptin) resistance in breast cancer cells. Breast Cancer Res Treat 118:113-134 (2009).
Foster et al. Induction of KLF4 in basal keratinocytes blocks the proliferation-differentiation switch and initiates squamous epithelial dysplasia. Oncogene 211(9):1491-1590 (2005).
Fraley et al. New generation liposomes: the engineering of an efficient vehicle for intracellular delivery of nucleic acids. Trends Biochem. Sci. 6:77 (1981).
Fraschini et al. Selective oxidation of primary alcohol groups of 13-cyclodextrin mediated by 2,2,6,6-tetramethylpiperidine-I-oxyl radical (TEMPO). Carbohydrate Research 328(4):585-589 (2000).
Gad et al. Muc1-Derived Glycopeptide Libraries With Improved Mhc Anchors Are Strong Antigens and Prime Mouse T Cells for Proliferative Responses to Lysates of Human Breast Cancer Tissue. Eur. J Immunol 33:1624-1632 (2003).
Garzon et al. Targeting microRNA's in cancer: rationale, strategies and challenges. Nature Re-views 9(10):775-89 (2010).
Gendler, Sandra J et al. Molecular Cloning and Expression of Human Tumor-associated Polymorphic Epithelial Mucin. The Journal of Biological Chemistry vol. 265,25: pp. 15286-15293 (1990).
Gervasi et al. nm23 influences proliferation and differentiation of PC12 cells in response to nerve growth factor. Cell Growth Differ 7:1689-1695 (1996).
Gill et al. The novel PARP1-selective inhibitor AZD5305 has reduced haematological toxicity when compared to PARP1/2 inhibitors in pre-clinical models. Poster # 1374 AACR 2021 Annual Apr. 10-19, 2020.
Goel, et al. Plasticity within the Antigen-Combining Site May Manifest as Molecular Mimicry in the Humoral Immune Response. Journal of Immunology 173:7358-7367 (2004).
Goldspiel, Barry R. et al. Human Gene Therapy. Clinical Pharmacy 12(7):488-505 (1993).
Gollub et al. Regulation of mucin gene expression in secretory epithelial cells. Biochemical and Biophysical Research Communications 197(2):667-73 (1993) (Abstract).
Graham et al. Intramuscular immunisation with MUC1 cDNA can protect C57 mice challenged with MUC1-expressing syngeneic mouse tumour cells. Int J Cancer 65(5):664-70 (1996).
Gregoriadis. Liposomes for drugs and vaccines. Trends in Biotechnology 3:235-241 (1985).
Gunathilake et al. Fabrication of Porous Materials from Natural/Synthetic Biopolymers and Their Composites. Materials 9(991):1-32 (2016).
Guo et al. Klf4 reverts developmentally programmed restriction of ground state pluripotency. Development 136(7):1063-1069 (2009).
Han et al. Tumor initialing cancer stem cells from human breast cancer cell lines. Int J Oncol 34:1449-53 (2009).
Hande et al. Structure-based and property-based drug design of AZD5305, a highly selective PARP1 inhibitor and trapper. Poster #296 AACR 2021. Apr. 10-15, 2021.
Hanisch. Design of a Muc1-Based Cancer Vaccine. Biochem Soc Trans 33:705-708 (2005).
Hanna, Jacob et al. Human Embryonic Stem Cells With Biological and Epigenetic Characteristics Similar to Those of Mouse ESCs. Proceedings of the National Academy of Sciences of the United States of America vol. 107,20: pp. 9222-9227 (2010).
Hikita, Sherry T et al. MUC1 Mediates the Growth of Human Pluripotent Stem Cells. PLoS One vol. 3,10: e3312, pp. 1-13 (2008).
Huang et al. MUC1 oncoprotein blocks glycogen synthase kinase 3beta-mediated phosphorylation and degradation of beta-catenin. Cancer Res 65(22):10413-22 (2005).
Huangfu et al. Induction of pluripotent stem cells by defined factors is greatly improved by small-molecule compounds. Nat Biotechnol 26(7):795-797 (2006).
Huangfu et al. Induction of pluripotent stem cells from primary human fibroblasts with only Oct4 and Sox2. Nat Biotechnol. 26(11):1269-75 (2008).
Illuzzi et al. In vitro cellular profiling of AZD5305, novel PARP1-selective inhibitor and trapper. Poster #1272 AACR2021, Apr. 10-15, 2021.
Irwin et al. Direct injection of a recombinant retroviral vector induces human immunodeficiency virus-specific immune responses in mice and nonhuman primates. J. Virol. 68:5036-5044 (1994).
Jaenisch, Rudolf et al. Stem Cells, The Molecular Circuitry of Pluripotency and Nuclear Reprogramming. Cell vol. 132,4: pp. 567-582 (2008).
Jarrad et al. MUC1 is a novel marker for the type II pneumocyte lineage during lung carcinogenesis. Cancer Research, 58(23):5582-5589 (1998).
Jiang et al. Surface-immobilization of adhesion peptides on substrate for ex vivo expansion of cryopreserved cord blood CD34+ cells. Biomaterials 27(13):2723-2732 (May 1, 2006).
Johannes et al. Discovery and first structural disclosure of AZD5305, a next generation, highly selective PARP1 inhibitor and trapper. AstraZeneca—AZD5305—a best in class highly selective PARP1 inhibitor. Presentation at AACR 2021 Apr. 10, 2021.
John et al. Tissue Engineered Bone and Adipose Tissue—An In Vitro Study. Trends Biomater Artif Organs 16:28-33 (2002).
Kaji et al. Virus-free induction of pluripotency and subsequent excision of reprogramming factors. Nature 458:771-775 (2009).
Kamata et al. Vaccination of mice with MUC1 cDNA suppresses the development of lung metastases. Clin Exp Metastasis 19(8):689-96 (2002).
Kawamura et al. Linking the p53 tumour suppressor pathway to somatic cell reprogramming. Nature 436:1140-4 (2009).

(56) References Cited

OTHER PUBLICATIONS

Khan et al. Adjustable Locks and Flexible Keys: Plasticity of Epitope—Paratope Interactions in Germline Antibodies. Journal of Immunology 192:5398-5405 (2014).

Kim, Young-In et al. Point Mutations Affecting the Oligomeric Structure of Nm23-H1 Abrogates its Inhibitory Activity on Colonization and Invasion of Prostate Cancer Cells. Biochemical and Biophysical Research Communications vol. 307,2: pp. 281-289 (2003).

Koller, Beverly H, and Oliver Smithies. Inactivating the beta 2-microglobulin locus in mouse embryonic stem cells by homologous recombination. Proceedings of the National Academy of Sciences 86:8932-8935 (1989).

Komarov et al. A chemical inhibitor of p53 that protects mice from the side effects of cancer therapy. Science 235:1733-7 (1999).

Kruyt et al. Optimization of Bone Tissue Engineering in Goats. 49th Meeting of the Orthopaedic Research Society, Poster #0929 (Nov. 15, 2007) www.ors.org/Transactions/49/0929.pdf.

Kuchenbauer et al. In-depth characterization of the microRNA trascriptome in a leukemia progression model. Genome Res 18:1787-1797 (2008).

Kufe, et al. Differential reactivity of a novel monoclonal antibody (DF3) with human malignant versus benign breast tumors. Hybridoma 3:223-232 (1984).

Kunath et al. FGF stimulation of the Erk1/2 signalling cascade triggers transition of pluripotent embryonic stem cells from self-renewal to lineage commitment. Development 134(16):2895-902 (2007).

Kunkel, Thomas A. Rapid and Efficient Site-Specific Mutagenesis without Phenotypic Selection. Proceedings of the National Academy of Sciences of the United States of America 82(2):488-492 (1985).

Lakso et al. Embryonic Expression of nm23 during Mouse Organonesis. Cell Growth Differ 3:873-879 (1992).

Lapidot et al. A cell initiating human acute myeloid leukaemia after transplantation into SCID mice. Nature 367:645-648 (1994).

Lascu et al. Quaternary Structure of Nucleoside Diphosphate Kineses. J Bioenerg Biomembr 32(3):227-236 (2000).

Leong et al. Epithelial membrane antigen (EMA) or MUC1 expression in monocytes and monoblasts. Pathology 35:422-427 (2003).

Ligtnberg, Marjolijn et al. Episialin, a Carcinoma Associated Mucin, is Generated by a Polymorphic Gene Encoding Splice Variants With Alternative Amino Termini. The Journal of Biological Chemistry vol. 265,10: pp. 5573-5578 (1990).

Lin et al. Glial-derived nexin, a differentially expressed gene during neuronal differentiation, transforms HEK cells into neuron-like cells. Int J of Dev Neurosci 23:9-14 (2005).

Lin et al. p53 induces differentiation of mouse embryonic stem cells by suppressing Nanog expression. Nat Cell Biol 7(2):165-171 (2005).

Lloyd, C. et al. Modelling the Human Immune Response: performance of a $10^{11}$ Human Antibody Repertoire Against a Broad Panel of Therapeutically Relevant Antigens. Protein Engineering Design and Selection 22(3):159-168 (2009).

Lombardi et al. nm23: Unraveling its Biological Function in Cell Differentiation. J Cell Physiol 182:144-149 (2000).

Lowry, W E et al. Generation of Human Induced Pluripotent Stem Cells From Dermal Fibroblasts. Proceedings of the National Academy of Sciences of the United States of America vol. 105,8: pp. 2883-2888 (2008).

Lu et al. MicroRNA expression profiles classify human cancers. Nature, 435(7043):834-838 (2005).

Luong et al. Expression of Nm23-H1 in AML correlates with white cell count at diagnosis and in vitro acts as a survival factor for primary AMLs cells: evidence of a novel autocrine survival factor in AML. Blood 102(part1of 2):2255 (2003).

Lyssiotis et al. Reprogramming of murine fibroblasts to induced pluripotent stem cells with chemical complementation of KIf4. PNAS USA 106:8912-8917 (2009).

MacDonald et al. Site-Directed Mutagenesis of nm23-HI. J Biol Chem 271(41):25107-25116 (1996).

Mahanta, Sanjeev et al. A Minimal Fragment of MUCI Mediates Growth of Cancer Cells. PLoS One vol. 3,4: e2054, pp. 1-12 (2008).

Maherali et al. A high-efficiency system for the generation and study of human induced pluripotent stem cells. Cell Stem Cell 3(3):340-345 (w/Supp Information) (2008).

Maherali, Nimet et al. Directly Reprogrammed Fibroblasts Show Global Epigenetic Remodeling And Widespread Tissue Contribution. Cell Stem Cell vol. 1,1: pp. 55-70 (2007).

Maimets et al. Activation of p53 by nutlin leads to rapid differentiation of human embryonic stem cells. Oncogene 27:5277-5237 (2008).

Makino et al. Immobilization of leukemia inhibitory factor (LIF) to culture murine embryonic stem cells. J Biosci Bioeng 98(5):374-379 (Jan. 1, 2004).

Masip et al. Reprogramming with defined factors: from induced pluripotency to induced transdifferentiation. Molecular Human Reproduction 16(11):856-868 (2010).

Matsui et al. Characterization of clonogenic multiple myeloma cells. Blood 103:2332-2336 (2004).

Meiri et al. Discovery of microRNAs and other small RNA in solid tumors. Nucleic Acids Res. 38(18):6234-6246 (2010).

Meseguer et al. Human endometrial mucin MUC1 is up-regulated by progesterone and down-regulated in vitro by the human blastocyst. Biol. Reprod. 64(2) 590-601 (2001).

Miyazaki et al. Overexpression of nm23-H2/NDP Kinase B in a Human Oral Squamous Cell Carcinoma Cell Line 36 Results in Reduced Metastasis, Differentiated Phenotype in the Metastatic Site, and Growth Factor-independent Proliferative Activity in Culture. Clin Cancer Res 5(12):4301-7 (1999).

Morgan, Richard A, and WF Anderson. Human Gene Therapy. Annual Review of Biochemistry 62:191-217 (1993).

Morin et al. Application of massively parallel sequencing to microRNA profiling and discovery in human embryonic stem cells. Genome Res 18:610-621 (2008).

Moss. Genetically engineered poxviruses for recombinant gene expression, vaccination, and safety. PNAS USA 93:11341-11348 (1996).

Moss. Replicating and host-restricted non-replicating vaccinia virus vectors for vaccine development. Dev. Biol. Stand. 82:55-63 (1994).

Mulligan, Richard C. The Basic Science of Gene Therapy. Science 260(5110):926-932 (1993).

Nakagawa et al., Generation of induced pluripotent stem cells without Myc from mouse and human fibroblasts. Nature Biotechnology 26:101-106 (2008).

Negroni et al. Neuroblastoma Specific Effects of DR-nrn23 and its Mutant Forms on Differentiation and Apoptosis. Cell Death Differ 7:843-850 (2000).

Neveu et al. MicroRNA Profiling Reveals Two Distinct p53-Related Human Pluripotent Stem Cell States. Cell Stem Cell 7(6):671-81 (2010).

Nichols, Jennifer et al. Naive and Primed Pluripotent States. Cell Stem Cell vol. 4,6: pp. 487-492 (2009).

Okabe-Kado et al., Inhibitory Action of nm23 Proteins on Induction of Erythroid Differentiation of Human Leukemia Cells. Biochimica Biophys Acta 1267:101-106 (1995).

Okabe-Kado et al. Physiological and Pathological Relevance of Extracellular NM23INDP Kinases, J Bioenerg Biomembr 35(1):89-93 (2003).

Okabe-Kado, Junko et al. A New Function of Nrn23INDP Kinase as a Differentiation Inhibitory Factor, Which Does Not Require it's Kinase Activity. FEES Letters vol. 363,3: pp. 311-315 (1995).

Okabe-Kado, Junko et al. Characterization of a Differentiation-Inhibitory Activity from Nondifferentiating Mouse Myeloid Leukemia cells. Cancer Research vol. 45, 10: pp. 4848-4852 (1985).

Okabe-Kado, Junko et al. Identity of a Differentiation Inhibiting Factor for Mouse Myeloid Leukemia Cells With NM23/Nucleoside Diphosphate Kinase. Biochemical and Biophysical Research Communications vol. 182,3: pp. 987-994 (1992).

Okita et al. Generation of mouse induced pluripotent stem cells without viral vectors. Science 322(5903):949-953 (2008).

(56) References Cited

OTHER PUBLICATIONS

Okita, keisuke et al. Generation of Germline-competent Induced Pluripotent Stem Cells. Nature vol. 448,7151: pp. 313-317 (2007).
Paoletti, Enzo. Applications of Pox Virus Vectors to Vaccination: An Update. Proceedings of the National Academy of Sciences of the United States of America vol. 93,21: pp. 11349-11353 (1996).
Park, In-Hyun et al. Reprogramming of Human Somatic Cells to Pluripotency with Defined Factors. Nature vol. 451,7175: pp. 141-146 (2008).
PCT/US2006/012092 International Search Report Nov. 13, 2006.
PCT/US2009/060272 International Search Report and Written Opinion dated Oct. 17, 2012.
PCT/US2010/038438 International Search Report and Written Opinion dated Nov. 5, 2010.
PCT/US2011040792 International Search Report and Written Opinion dated Feb. 29, 2012.
PCT/US2012/029706 International Search Report and Written Opinion dated Oct. 1, 2012.
Plunkett et al. Protection against MUC1 expressing mouse tumours by intra-muscular injection of MUC1 cDNA requires functional COB+ and CD4+ T cells but does not require the MUC1 tandem repeat domain. Int J Cancer 109(5):691-7 (2004).
Poosarla, et al. Computational de novo design of antibodies binding to a peptide with high affinity. Biotechnology and Bioengineering 114(6):1331-1342 (2017).
Pugachev et al. Double-subgenomic Sindbis virus recombinants expressing immunogenic proteins of Japanese encephalitis virus induce significant protection in mice against lethal JEV infection. Virology 212:587-594 (1995).
Qaraghuli, et al. Antibody-protein binding and conformational changes: identifying allosteric signalling pathways to engineer a better effector response. Nature Scientific Reports 10(1):13969, 1-10 (2020).
Rabia, et al. Understanding and overcoming trade-offs between antibody affinity, specificity, stability and solubility. Biochemical engineering journal 137:365-374 (2018).
Raina et al. Direct targeting of the mucin 1 oncoprotein blocks survival and tumorigenicity of human breast carcinoma cells. Cancer Res 69(12):5133-5141 (2009).
Rajabi et al. Mucin 1 oncoprotein expression is suppressed by the miR-125b oncomir. Genes & Cancer 1(1):82-68 (2010).
Rudikoff et al. Single amino acid substitution altering antigen-binding Specificity. PNAS USA 79:1979-1983 (1982).
Rughetti et al. Regulated expression of MUC1 epithelial antigen in erythropoiesis. Br. J. Haematol 120(2):344-352 (2003).
Sachdeva et al. MicroRNA-145 suppresses cell invasion and metastasis by directly targeting mucin 1. Cancer Res. 70(1):378-87 (2010).
Sassen et al. MicroRNA-implications for cancer. Virchows Archive 452(1):1-10 (Nov. 27, 2007).
Sato et al. Maintenance of pluripotency in human and mouse embryonic stem cells through activation of Wnt signaling by a pharmacological GSK-3-specific inhibitor. Nat Med. 10(1):55-63 (2004).
Sawhney et al., Bioerodible Hydogels Based on Photopolymerized Poly(ethyleneglycol)-co-poly(d-hydroxy acid) Diacrylate Macromers. Macromolecules 26:81-587 (1993).
Schepeler et al. Diagnostic and Prognostic MicroRNAs in Stage II Colon Cancer. Cancer Research 68(15):6416-6426 (2008).
Shan et al. Transplant for marrow stem cell on ischemic heart disease. Chinese Journal Clinical Pharmacology and Therapeutics 7(5):473-476 (2002).
Shaw et al. Preferential transformation of human neuronal cells by human adenoviruses and the origin of HEK 293 cells. FASEB 16:869-71 (2002).
Siegfried Culture of primary lung tumors using medium conditioned by a lung carcinoma cell line. J. Cell Biochem. 41:91-95 (1989).
Silva et al. Capturing Pluripotency. Cell 132(4):532-6 (2008).
Silva et al., Promotion of reprogramming to ground state pluripotency by signal inhibition. PLoS Biol. 6(10):e253 (2008).
Singh et al. Identification of a cancer stem cell in human brain tumors. Cancer Res., 63(18):5821-8 (2003).
Smagghe et al. MUCI ligand, NM23-H1, is a novel growth factor that maintains human stem cells in a more naive state. PLoS One 8(3):E58601 (Mar. 2013).
Snoek et al. Protein Kinase C and Phorbol Ester Receptor expression Related to Growth and Differentiation of Nullipotent and Pluripotent Embryonal Carcinoma Cells. Developmental Biology 115(2):282-292 (1986).
Soldner et al. Parkinson's Disease Patient-Derived Induced Pluripotent Stem Cells Free of Viral Reprogramming Factors. Cell 136(5):964-977 (2009).
Sommer et al.: Induced pluripotent stem cell generation using a single lentiviral stem cell cassette. Stem Cells 27(3):543-549 (2009).
Sorscher et al. Microinjection of an NM23 specific antibody inhibits cell division in rat embryo fibroblasts. Biochem Biophy Res Commun 195(1):336-345 (1993).
Spicer et al. Molecular cloning and analysis of the mouse homologue of the tumor-associated mucin, MUC1, reveals conservation of potential O-glycosylation sites, transmembrane, and cytoplasmic domains and a loss of minisatellite-like polymorphism. J. Biol. Chem 266(23):15099-15109 (1991).
Spizzo et al. miR-145 participates with TP53 in a death-promoting regulatory loop and targets estrogen receptor -[alpha] in human breast cancer cells. Cell Death and Differentiation 17(2):246-254 (Sep. 4, 2009).
Sridharan et al. Role of the murine reprogramming factors in the induction of pluripotency. Cell 136(2):364-377 (2009).
Stadtfeld et al. Induced pluripotent stem cells generated without viral integration. Science 322(5903):945-9 (2008).
Staniszewska et al. The novel PARP1-selective inhibitor, AZD5305, is efficacious as monotherapy and in combination with standard of care chemotherapy in in vivo preclinical models. Poster #1270 AACR 2021. Apr. 10-15 and May 17-21, 2021.
Stavridis et al. A discrete period of FGF-induced Erk1/2 signalling is required for vertebrate neural specification. Development 134:2889-2894 (2007).
Stingl, John et al. Epithelial Progenitors in the Normal Human mammary Gland. Journal of Mammary Gland Biology and Neoplasia vol. 10,1: pp. 49-59 (2005).
Strom et al. Small-molecule inhibitor of p53 binding to mitochondria protects mice from gamma radiation. Nat Chem Biol. 2(9)474-9 (2006).
Subramaniam et al. Cancer stem cells: a novel paradigm for cancer prevention and treatment. Mini Rev Med Chem 10(5):359-371 (2010).
Takahashi, Kazutoshi et al. Induction of pluripotent stem cells from adult human fibroblasts by defined factors. Cell 131(5):861-872 (2007).
Takahashi, Kazutoshi et al. Induction of Pluripotent Stem Cells from Mouse Embryonic and Adult Fibroblast Cultures by Defined Factors. Cell vol. 126,4: pp. 663-676 (2006).
Taulli et al. The muscle-specific microRNA miR-206 blocks human rhabdomyosarcoma growth in xenotransplanted mice by promoting myogenic differentiation. J. Clin. Invest. 119(8):2366-2378 (2009).
Thathiah et al. MT1-MMP mediates MUC1 Shedding independent of TACE/ADAM17. Biochem. J. 382:363-373 (2004).
Thathiah et al., Tumor Necrosis Factor alpha Stimulates Muc1 Synthesis and Ectodomain Release in a Human Uterine Epithelial Cell Line. Endocrinology 145(9):4192-4203 (2004).
Thathiah et al., Tumor Necrosis Factor-alpha Converting Enzyme/Adam 17 Mediates Muc1 Shedding. J Biol Chem 278(5):3386-3394 (2003).
ThermoScientific Datasheet entitled Thermo Scientific Nunclon Vita Surface, 2010 [online]. [Retrieved on Sep. 13, 2012]. Retrieved from the internet: < url: >http://www.thermofisher.com.au/Uploads/file/Scientific/Bio-Innovation/Thermo-Scientific-Nunclon-Vita-Surface-Application-Note.pdf .</url.
Thomson et al. Embryonic stem cell lines derived from human blastocysts. Science 282(5391):1145-1147 (1998).
Tolstoshev, Paul. Gene Therapy, Concepts, Current Trials and Future Directions. Annual Review Pharmacology and Toxicology 32:573-596 (1993).

(56) References Cited

OTHER PUBLICATIONS

Townsend et al. Characterization of CD8+ cytotoxic T-lymphocyte responses after genetic immunization with retrovirus vectors expressing different forms of the hepatitis B virus core and e antigens. J. Virol. 71:3365-3374 (1997).
U.S. Appl. No. 11/278,122 Office Action dated Jan. 11, 2010.
U.S. Appl. No. 11/278,122 Office Action dated Jan. 31, 2008.
U.S. Appl. No. 11/278,122 Office Action dated May 3, 2010.
U.S. Appl. No. 11/278,122 Office Action dated Nov. 22, 2013.
U.S. Appl. No. 11/278,122 Office Action dated Oct. 31, 2008.
U.S. Appl. No. 11/278,122 Office Action dated Sep. 13, 2013.
U.S. Appl. No. 12/577,103 Office Action dated Aug. 5, 2015.
U.S. Appl. No. 12/577,103 Office Action dated Dec. 2, 2019.
U.S. Appl. No. 12/577,103 Office Action dated Feb. 9, 2017.
U.S. Appl. No. 12/577,103 Office Action dated Jan. 24, 2011.
U.S. Appl. No. 12/577,103 Office Action dated Jun. 6, 2023.
U.S. Appl. No. 12/577,103 Office Action dated Mar. 11, 2021.
U.S. Appl. No. 12/577,103 Office Action dated Mar. 8, 2019.
U.S. Appl. No. 12/577,103 Office Action dated Nov. 18, 2011.
U.S. Appl. No. 12/577,103 Office Action dated Nov. 22, 2021.
U.S. Appl. No. 12/577,103 Office Action dated Nov. 28, 2014.
U.S. Appl. No. 12/577,103 Office Action dated Oct. 12, 2017.
U.S. Appl. No. 12/577,103 Office Action dated Sep. 15, 2022.
U.S. Appl. No. 12/814,420 Office Action dated Nov. 13, 2012.
U.S. Appl. No. 13/162,558 Office Action dated Aug. 18, 2017.
U.S. Appl. No. 13/162,558 Office Action dated Feb. 10, 2015.
U.S. Appl. No. 13/162,558 Office Action dated Jun. 26, 2013.
U.S. Appl. No. 13/162,558 Office Action dated Jun. 8, 2018.
U.S. Appl. No. 13/162,558 Office Action dated Nov. 2, 2015.
U.S. Appl. No. 13/162,558 Office Action dated Nov. 29, 2016.
U.S. Appl. No. 13/966,214 Office Action dated Aug. 12, 2015.
U.S. Appl. No. 13/966,214 Office Action dated Aug. 20, 2020.
U.S. Appl. No. 13/966,214 Office Action dated Jul. 15, 2016.
U.S. Appl. No. 13/966,214 Office Action dated Mar. 7, 2019.
U.S. Appl. No. 13/966,214 Office Action dated May 18, 2018.
U.S. Appl. No. 13/966,214 Office Action dated Nov. 8, 2019.
U.S. Appl. No. 13/966,214 Office Action dated Sep. 21, 2017.
U.S. Appl. No. 14/209,651 Office Action dated Feb. 4, 2016.
U.S. Appl. No. 14/209,651 Office Action dated Jul. 6, 2017.
U.S. Appl. No. 14/209,651 Office Action dated Jul. 8, 2015.
U.S. Appl. No. 14/480,586 Office Action dated Apr. 7, 2016.
U.S. Appl. No. 14/596,051 Office Action dated Aug. 11, 2023.
U.S. Appl. No. 14/604,579 Office Action dated Sep. 13, 2022.
U.S. Appl. No. 16/912,135 Office Action dated Apr. 17, 2023.
U.S. Appl. No. 16/912,135 Office Action dated Jul. 27, 2023.
U.S. Appl. No. 16/921,352 Office Action dated May 5, 2021.
Vacanti et al. Identification and initial characterization of spore-like cells in adult mammals. J Cell Biochem 80:455-60 (2001).
Vassilev et al. In vivo activation of the p53 pathway by small-molecule antagonists of MDM2. Science 303:844-848 (2004).
Venturelii et al. Overexpression of dr-nrn23, a protein encoded by a member of the nm23 gene family, inhibits granulocyte differentiation and induces apoptosis in 32d013 myeloid cells. PNAS USA 92:7435-7439 (1995).
Villa-Diaz et al. Synthetic polymer coatings for long-term growth of human embryonic stem cells. Nature Biotechnol 28(6):581-583 (2010).
Wagner et al. Potent and selective inhibition of gene expression by an antisense heptanucleotide. Nat Biotechnol 14:840-844 (1996).
Wang et al. miR-145 inhibits breast cancer cell growth through RTKN. International Journal of Oncology 34:1461-1466 (May 1, 2009).
Watanabe, Kiichi et al. A Rock Inhibitor Permits Survival of Dissociated Human Embryonic Stem Cells. Nature Biotechnology vol. 25,6: pp. 681-686 (2007).
Wei et al. Human MUC1 oncoprotein regulates p53-responsive gene transcription in the genotoxic stress response. Cancer Cell. 7(2):167-78 (2005).
Wei et al. Human mucin 1 oncoprotein represses transcription of the p53 tumor suppressor gene. Cancer Res 67(4):1853-1858 (2007).
Wen et al. Nuclear association of the cytoplasmic tail of MUC1 and beta-catenin. J Biol Chem. 278(39):38029-39 (2003).
Wernig, Marius et al. c-Myc is Dispensable for Direct Reprogramming of Mouse Fibroblasts. Cell Stem Cell vol. 2,1: pp. 10-12 (2008).
Wernig, Marius et al. In Vitro Reprogramming of Fibroblasts Into a Pluripotent ES-cell-like State. Nature vol. 448,7151: pp. 318-324 (2007).
Willems et al. Decrease in Nucleoside Diphosphate Kinase (NDPK/nm23) Expression during Hematopoietic Maturation. J Biol Chem 273(22):13663-8 (1998).
Willems et al. Extracellular Nucleoside Diphosphate Kinase NM231NDPK Modulates Normal Hematopoietic Differentiation. Experimental Hematology 30:640-648 (2002).
Woltjen, Knut et al. Piggybac Transposition Reprograms Fibroblasts to Induced Pluripotent Stem Cells. Nature vol. 458,7239: pp. 766-770 (2009).
Wright et al. Cytotoxic T lymphocytes from humans with adenocarcinomas stimulated by native MUC1 mucin and a mucin peptide mutated at a glycosylation site. J Immunother 23(1)2-10 (2000).
Wu et al. Receptor-mediated in vitro gene transformation by a soluble DNA carrier system. J Biol Chem 262(10):4429-4432 (1987).
Wu, George Y, and C H Wu et al. Delivery systems for Gene Therapy. Biotherapy 3(1):87-95 (1991).
Xiang et al. A replication-defective human adenovirus recombinant serves as a highly efficacious vaccine carrier. Virology 219:220-227 (1996).
Xu et al. MicroRNA-145 Regulates OCT4, SOX2, and KLF4 and Represses Pluripotency in Human Embryonic Stem Cells. Cell. 137(4):647-658 (2009).
Yamanaka, Shinya. Strategies and New Developments in the Generation of Patient-specific Pluripotent Stem Cells. Cell Stem Cell vol. 1,1: pp. 39-49 (2007).
Yamashita et al. Forskolin and phorbol ester have opposite effects on the expression of mucin-associated sialyl-LewisAa in pancreatic cancer cells. European Journal of Cancer 36(1):113-120 (2000).
Yu et al. Induced pluripotent stem cell lines derived from human somatic cells. Science 318:1917-1920 (2007).
Yu, Junying et al. Human Induced Pluripotent Stem Cells Free of Vector and Transgene Sequences. Science vol. 324,5928: pp. 797-801 (2009).
Yunbin et al. Effect of hematopoietic growth factors on short expansion of umbilical cord blood CD34+ cells in vitro. Journal Fujian Medical College 37(2):147-50 (2003).
Zhao et al. Generation of cytotoxic and humoral immune responses by nonreplicative recombinant Semliki Forest virus. PNAS USA 92:3009-3013 (1995).
Zhong XY, et al. Evaluation of MUC1 and EGP40 in Bone marrow and Peripheral Blood as a Marker for Occult breast cancer. Archvies of Gynecology and Obstetrics vol. 264,4: pp. 177-181 (2001).
Zhou et al. Expression and purification of single chain anti-HBx antibody in E. coli. 123(11-12):609-13 (1997).
Zhou, Hongyan et al. Generation of Induced Pluripotent Stem Cells Using Recombinant Proteins. Cell Stem Cell vol. 4,5: pp. 381-384 (2009).
Zijlstra, Maarten et al. Germ-line transmission of a disrupted β2-microglobulin gene produced by homologous recombination in embryonic stem cells. Nature 342:435-438 (1989).
Zotter et al. Monoclonal antibodies to epithelial sialomucins recognize epitopes at different cellular sites in adenolymphomas of the parotid gland. Int J Cancer Suppl 3:38-44 (1988).
Zou, Xiaoming et al. P53 Deficiency Increases Transformation by V-Abl and Rescues the Ability of a C-terminally Truncated V-Abl Mutant to Induce Pre-B Lymphoma in Vivo. Molecular Cell Biology vol. 20,2: pp. 628-633 (2000).
Agou et al. Chapter 29: In Vivo Protein Cross-Linking. From Protein-Protein Interactions: Methods and Applications 261:427-442 (2004).
Amendola et al. DR-nm23 gene expression in neuroblastoma cells: relationship to integrin expression, adhesion characteristics, and differentiation. J Natl Cancer Inst. 89(17):1300-1310 (1997).

(56) References Cited

OTHER PUBLICATIONS

Bakiri et al. Promoter Specificity and Biological Activity of Tethered AP-1 Dimers. Mol Cell Biol 22(13):4952-4964 (2002).
BD ITS+. Screenprint of Becton Dickinson's webpage detailing the composition of ITS+ accessed at https://www.annericanpharnnaceuticalreview.conn/25243-Cell-Culture-Growth-Factors/5821288-ITS-Universal-Cell-Culture-Supplement-Premix/ on May 5, 2018, available online since Apr. 1, 2002 (2002).
Boissan, Mathieu et al. The Mammalian Nm23/NDPK Family: from Metastasis Control to Cilia Movement. Molecular Cell Biochemistry 329(1-2):51-62 (2009).
Breitenlechner, Christine et al. Protein Kinase A in Complex With Rho-kinase Inhibitors Y-27632, Fasudil, and H-1152p: Structural Basis of Selectivity. Structure 11(12):1595-1607 (2003).
Brugger, Wolfram et al. Expression of MUC-1 Epitopes on Normal Bone Marrow: Implications for the Detection of Micrometastatic Tumor Cells. Journal of Clinical Oncology 17(5):1535-1544 (1999).
Carter, M. G. et al. A Primitive Growth Factor, NME7AB, Is Sufficient to Induce Stable Naïve State Human Pluripotency; Reprogramming in This Novel Growth Factor Confers Superior Differentiation. Stem Cells 34(4):847-859 (2016).
Chae et al. Transactivation potential of the C-terminus of human NM23-H1. Febs Letters 423(2):235-238 (Mar. 3, 1998).
Chang et al. A nucleoside diphosphate kinase A (NM23-H1) serine 120—glycine substitution in advanced 5 stage neuroblastoma affects enzyme stability and alters protein-protein interaction. Oncogene 12(3):659-667 (Feb. 1996) (Abstract).
Chen et al., A Novel Signaling by Vitamin A/retinol Promotes Self Renewal of Mouse Embryonic Stem Cells by Activating PI3K/Akt Signaling Pathway via Insulin-Like Growth factor-1 Receptor. Stem Cells 28(1):57-63 (2010).
Chen, Guokai et al. Chemically Defined Conditions for Human iPSC Derivation and Culture. Nature Methods 8(5):424-431 (2011).
Database UniProt[online], Accession No. P15531,Nov. 30, 2010 uploaded, [retrieved on Aug. 19, 2021], ,Definition:RecName >https://www.uniprot.org/uniprot/P15531.txt?version=131,Definition:RecName : Full=Nucleoside diphosphate kinase A.
Dearolf et al. Developmental consequences of awdb3, a cell-autonomous lethal mutation of Drosophila induced by hybrid dysgenesis. Dev Biol. 129(1):159-168 (1988).
Desvignes et al., Nme protein family evolutionary history, a vertebrate perspective. BMC Evol Biol. 9:256 [1-25] (2009).
Efe et al. Conversion of mouse fibroblasts into cardiomyocytes using a direct reprogramming strategy. Nat Cell Biol. 13(3):215-222 (2011).
Fletcher et al. Variations in humanized and defined culture conditions supporting derivation of new human embryonic stem cell lines. Cloning Stem Cells 8(4):319-334 (2006).
Gauthaman et al. Effect of Rock inhibitor Y-27632 on normal and variant human embryonic stem cells (hESCs) in vitro: its benefits in hESC expansion. Stem Cell Rev Rep. 6(1):86-95 (2010).
Genbank Accession No. AAO85436. NM23-H1. Earliest Publication Date 2003.
Greber, Boris et al. FGF Signalling Inhibits Neural Induction In Human Embryonic Stem Cells. The EMBO Journal 30(24):4874-4884 (2011).
Hanna, Jacob H et al. Pluripotency and Cellular Reprogramming: Facts, Hypotheses, Unresolved Issues. Cell 143(4):508-525 (2010).
Ieda et al. Direct reprogramming of fibroblasts into functional cardiomyocytes by defined factors. Cell. 142(3):375-386 (2010).
Ikeda: NDP kinase 7 is a conserved microtubule-binding protein preferentially expressed in ciliated cells. Cell Struct Funct. 35(1):23-30 (2010).
Kim et al. A preliminary X-ray study of human nucleoside diphosphate kinase A under oxidative conditions. Acta Crystallogr. Sect. F Struct. Biol. Cryst. Commun. 66: 1490-1492 (2010).
Komander, David et al. Mechanism of Multi-site Phosphorylation From A Rock-LRhoE Complex Structure. The EMBO Journal 27(23):3175-3185 (2008).

Lacombe et al. The human Nm23/nucleoside diphosphate kinases. J Bioenerg Biomembr. 32(3):247-258 (2000).
Lilly et al. Nm23-h1 indirectly promotes the survival of acute myeloid leukemia blast cells by binding to more mature components of the leukemic clone. Cancer Res. 71(3):1177-1186 (2011).
Lin, Tongxiang et al. A Chemical Platform For Improved Induction of Human iPSCs. Nature Methods 6(11):805-808 (2009).
Lombardi et al. The association of the Nm23-M1 protein and beta-tubulin correlates with cell differentiation. Exp Cell Res. 217(2):267-271 (1995).
Mehus et al. NDK7_Human UniProt Submission Accession No. Q9Y5B8 https://www.uniprot.org/uniprot/Q9Y5B8.txt?version=97 [1-4] (May 31, 2011).
Mehus et al. NME6: a new member of the nm23/nucleoside diphosphate kinase gene family located on human chromosome 3p21.3. Hum Genet. 104(6):454-459 (1999).
Milon et al. The Human NM-23-H4 gene product is a mitochondrial nucleoside diphosphate kinase. J Biol Chem 275(19): 14264-14272 (May 12, 2000).
Miranda-Vizuete et al. Cloning and developmental analysis of murid spermatid-specific thioredoxin-2 (SPTRX-2), a novel sperm fibrous sheath protein and autoantigen. J Biol Chem. 278(45):44874-44885 (2003).
Miyamoto, Masaaki et al. Role of nm23 in the Regulation of Cell Shape and Migration via Rho Family GTPase Signals. Molecular and Cell Biochemistry 329(1-2):175-179 (2009).
Morera et al. X-ray structure of human nucleoside diphosphate kinase B complexed with GDP at 2 A resolution. Structure 3:1307-14 (1995).
Munoz-Dorado et al. Nucleoside diphosphate kinase from Myxococcus xanthus. II. Biochemical characterization. J Biol Chem. 265(5):2707-2712 (1990).
Murakami et al. The suppressor of metastasis Nm23-H1 interacts with the Cdc42 Rho family member and the pleckstrin homology domain of oncoprotein Dbl-1 to suppress cell migration. Cancer Biol Ther 7(5):677-688 (2008.
Murakami, Masanao et al. Nm23-H1 Modulates the Activity of the Guanine Exchange Factor Dbl-1. International Journal of Cancer 123(3):500-510 (2008).
Neuhold et al. HLH forced dimers: Tethering MyoD to E47 generates a dominant positive myogenic factor insulated from negative regulation by Id. Cell 74(6):1033-1042 (Sep. 24, 1993).
Ohata, Hirokazu et al. Induction of The Stem-like Cell Regulator CD44 by Rho Kinase Inhibition Contributes to The Maintenance of Colon Cancer-initiating Cells. Cancer Research 72(19):5101-5110 (2012).
Ohgushi, Masatoshi et al. Molecular Pathway and Cell State Responsible for Dissociation-induced Apoptosis in Human Pluripotent Stem Cells. Cell Stem Cell 7(2):225-239 (2010).
Olson, Michael F. Applications for Rock Kinase Inhibition. Current Opinion in Cell Biology 20(2):242-248 (2008).
PCT/US2012/036975 International Search Report and Written Opinion dated Oct. 10, 2012.
PCT/US2012/060684 International Search Report and Written Opinion dated Apr. 5, 2013.
PCT/US2013/050563 International Search Report and Written Opinion dated Nov. 29, 2013.
PCT/US2013/051899 International Search Report and Written Opinion dated Dec. 3, 2013.
Pease, Shirley et al. Isolation of Embryonic Stem (ES) Cells in Media Supplemented With Recombinant Leukemia Inhibitory Factor (LIF). Developmental Biology 141(2):344-352 (1990).
Perina, Drago et al. Characterization of Nme6-like Gene/protein From Marine Sponge Suberites Domuncula. Naunyn-Schmiedeberg's Archives of Pharmacology 384(4-5):451-460 (2011).
Pluckthun et al. New protein engineering approaches to multivalent and bispecific antibody fragments. Immunotechnology 3(2):1380-2933 (Jun. 1997).
Poon et al. Tandem Dimerization of the Human p53 Tetramerization Domain Stabilizes a Primary Dinner Intermediate and Dramatically Enhances its Oligomeric Stability. J Mol Biol 365:1217-1231 (2007).

(56) References Cited

OTHER PUBLICATIONS

Postel et al. Mutational analysis of NM23-H2/NDP kinase identifies the structural domains critical to recognition of a c-myc regulatory element. PNAS USA 93(14):6892-6897 (Jul. 1996).
Postel et al. Structure-based mutational and functional analysis identify human NM23-H2 as a multifunctional enzyme. Biochemistry 41(20):6330-6337 (Apr. 27, 2002).
Rath, Nicola et al. Rho-associated Kinases in Tumorigenesis: Reconsidering ROCK Inhibition For Cancer Therapy. EMBO Reports 13(10):900-908 (2012).
Riento, Kirsi et al. RhoE Binds to ROCKI and Inhibits Downstream Signaling. Molecular and Cellular Biology 23(12):4219-4229 (2003).
Rosengard et al. Reduced Nm23/Awd protein in tumour metastasis and aberrant *Drosophila* development. Nature 342(6246):177-180 (1989) (Abstract).
Schlessinger. Cell signaling by receptor tyrosine kinases. Cell. 103(2):211-225 (2000).
Sumer et al. The use of signalling pathway inhibitors and chromatin modifiers for enhancing pluripotency. Theriogenology 74(4):525-533 (2010).
Thompson, Andrew B et al. A Gold Nanoparticle Platform for Protein-protein Interactions and Drug Discovery. ACS Applied Materials and Interfaces 3(8):2979-2987 (2011).
Timmons et al. The expression of the *Drosophila* awd gene during normal development and in neoplastic brain tumors caused by lgl mutations. Dev Biol. 158(2):364-379 (1993).
U.S. Appl. No. 14/077,061 Office Action dated Mar. 9, 2018.
U.S. Appl. No. 14/077,061 Office Action dated Nov. 25, 2015.
U.S. Appl. No. 14/077,061 Office Action dated Sep. 20, 2018.
U.S. Appl. No. 14/077,061 Office Action dated Sep. 30, 2016.
U.S. Appl. No. 14/254,749 Office Action dated Aug. 8, 2017.
U.S. Appl. No. 14/254,749 Office Action dated Feb. 19, 2020.
U.S. Appl. No. 14/254,749 Office Action dated Mar. 25, 2022.
U.S. Appl. No. 14/254,749 Office Action dated May 17, 2018.
U.S. Appl. No. 14/254,749 Office Action dated May 17, 2019.
U.S. Appl. No. 14/254,749 Office Action dated May 26, 2021.
U.S. Appl. No. 14/596,051 Office Action dated Apr. 17, 2018.
U.S. Appl. No. 14/596,051 Office Action dated Dec. 5, 2018.
U.S. Appl. No. 14/596,051 Office Action dated Feb. 23, 2017.
U.S. Appl. No. 14/596,051 Office Action dated Jan. 28, 2020.
U.S. Appl. No. 14/596,051 Office Action dated Jan. 8, 2024.
U.S. Appl. No. 14/596,051 Office Action dated Jul. 14, 2021.
U.S. Appl. No. 14/596,051 Office Action dated Jul. 27, 2020.
U.S. Appl. No. 14/596,051 Office Action dated May 19, 2016.
U.S. Appl. No. 14/596,051 Office Action dated Sep. 12, 2022.
U.S. Appl. No. 14/604,579 Office Action dated Feb. 3, 2020.
U.S. Appl. No. 14/604,579 Office Action dated Jun. 6, 2019.
U.S. Appl. No. 14/604,579 Office Action dated Mar. 20, 2018.
U.S. Appl. No. 14/604,579 Office Action dated Mar. 21, 2017.
U.S. Appl. No. 14/604,579 Office Action dated Mar. 26, 2021.
U.S. Appl. No. 14/604,579 Office Action dated Oct. 29, 2021.
U.S. Appl. No. 16/447,812 Office Action dated Apr. 1, 2022.
U.S. Appl. No. 16/447,812 Office Action dated Jan. 22, 2024.
U.S. Appl. No. 16/447,812 Office Action dated Oct. 27, 2022.
U.S. Appl. No. 16/447,812 Office Action dated Sep. 28, 2023.
U.S. Appl. No. 18/640,690 Office Action dated Aug. 2, 2024.
Valentijn et al. Read-through transcript from NM23-H1 into the neighboring NM23-H2 gene encodes a novel protein, NM23-LV. Genomics 87(4):483-489 (Jan. 25, 2006).
Wang et al. Requirement of Nanog dimerization for stem cell self-renewal and pluripotency, PNAS USA 105(17):6326-6331 (Apr. 29, 2008).
Ward, Yvona et al. The GTP Binding Proteins Gem and Rad Are Negative Regulators of The Rho-rho Kinase Pathway. Journal of Cell Biology 157(2):291-302 (2002).
Xie et al. NME1 at the human maternal-fetal interface downregulates titin expression and invasiveness of trophoblast cells via MAPK pathway in early pregnancy. Reproduction 139(4):799-808 (2010).
Yamashiro et al. Alteration of nm23 gene expression during the induced differentiation of human leukemia cell lines. Oncogene 9(9):2461-2468 (1994) (Abstract).
Zhou et al. Double mutant P96S/S120G of Nm23-H1 abrogates its NDPK activity and motility-suppressive ability. Biochem Biophys Res Commun. 356(2):348-353 (2007).

| Surface:<br>Vita + 2D6C8– no ROCi<br>Source:<br>H9s NM23 from feeders<br>Media Post – 8nM NM23-MM<br><br>• Day 1: plated<br>• Day 5: 4 ES organized colonies; no differentiation<br>• Day 8: 3 fully formed colonies, beginning to differentiate at edge; area of propagating single ES cells<br>• Day 9: these colonies harvested & passaged onto Vita + 2D6C8<br>• Day 13: 2 fully undifferentiated colonies growing | Surface:<br>Vita + 2D6C8– no ROCi<br>Source:<br>H9s bFGF-CM Matrigel<br>Media Post – 4ng/ml bFGF + 50% MEF conditioned media<br><br>• Day 1: Plated<br>• Day 5: No live ES cells; few fibroblasts<br>• Day 8: Only fibroblast-like cells | Surface:<br>Vita + 2D6C8– no ROCi<br>Source:<br>H9s bFGF-CM Matrigel<br>Media Post – 4ng/ml bFGF + 50% MEF conditioned media<br><br>• Day 1: Plated<br>• Day 5: No live ES cells; few fibroblasts<br>• Day 8: Only fibroblast-like cells |
|---|---|---|
| Surface:<br>Vita Alone – no ROCi<br>Source:<br>H9s NM23 from feeders<br>Media Post – 8nM NM23-MM<br><br>• Day 1: Plated<br>• Day 5: 4 colonies look like they may differentiate – no organized center<br>• Day 8: 3 colonies differentiated | Surface:<br>Vita Alone – no ROCi<br>Source:<br>H9s bFGF-CM Matrigel<br>Media Post – 4ng/ml bFGF + 50% MEF conditioned media<br><br>• Day 1: Plated<br>• Day 5: No live ES cells; few fibroblasts<br>• Day 8: Only fibroblast-like cells | Surface:<br>Vita Alone – no ROCi<br>Source:<br>H9s bFGF-CM Matrigel<br>Media Post – 4ng/ml bFGF + 50% MEF conditioned media<br><br>• Day 1: Plated<br>• Day 5: No live ES cells; few fibroblasts<br>• Day 8: Only fibroblast-like cells |

Fig. 1

| Plating Volume 1 ml – no growth factor in plating media<br>Time to correct volume and add NM23<br>T = 15 min<br><br>• Day 3: 14 colonies<br>• Day 6: 5-7 colonies mixture of fully undifferentiated, some edges differentiating, and some fully differentiated | Plating Volume 1 ml – no growth factor in plating media<br>Time to correct volume and add NM23<br>T = 30 min<br><br>• Day 3: 5 colonies<br>• Day 6: 5-7 colonies mixture of fully undifferentiated, some edges differentiating, and some fully differentiated | Plating Volume 1 ml – no growth factor in plating media<br>Time to correct volume and add NM23<br>T = 1 hr<br><br>• Day 3: 8 colonies<br>• Day 6: 5-7 colonies mixture of fully undifferentiated, some edges differentiating, and some fully differentiated |
|---|---|---|
| Plating Volume 1 ml – no growth factor in plating media<br>Time to correct volume and add NM23<br>T = 3 hrs<br><br>• Day 3: 8 colonies<br>• Day 6: 5-7 colonies mixture of large fully undifferentiated, some edges differentiating, and some fully differentiated | Plating Volume 1 ml – no growth factor in plating media<br>Time to correct volume and add NM23<br>T = 12 hrs<br><br>• Day 3: colonies<br>• Day 6: 5-7 colonies –do not look as good as T<O/N - mixture of fully undifferentiated, some edges differentiating, and some fully differentiated | Plating Volume 1 ml – no growth factor in plating media<br>Time to correct volume and add NM23<br>T = 24 hrs<br><br>• Day 3: 6 colonies<br>• Day 6: 5-7 colonies – do not look as good as T<O/N - mixture of fully undifferentiated, some edges differentiating, and some fully differentiated |

Fig. 5

| Surface:<br>Vita + 2D6C8-no ROCi<br>Source 1:<br>iPS NM23 on Matrigel<br>Media Post – 8nM NM23-MM<br><br>• Day 1: Plated<br>• Day 3: 2-3 undifferentiated colonies<br>• Day 6: 5-6 colonies undifferentiated, centers beginning to differentiate | Surface:<br>Vita + 2D6C3-no ROCi<br>Source 1:<br>iPS NM23 on Matrigel<br>Media Post – 8nM NM23-MM<br><br>• Day 1: Plated<br>• Day 3: 2-3 undifferentiated colonies<br>• Day 6: 5-6 colonies undifferentiated, centers beginning to differentiate | Surface:<br>Vita + 2D6C8-no ROCi<br>Source: 2<br>iPS FGF on MEF Feeders<br>Media Post – 8nM NM23-MM<br><br>• Day 1: Plated<br>• Day 3: 0 all floating<br>• Day 6: 6-7 colonies undifferentiated, centers beginning to differentiate |
|---|---|---|
| Surface:<br>Vita Alone – no ROCi<br>Source 1:<br>iPS NM23 on Matrigel<br>Media Post – 8nM NM23-MM<br><br>• Day 1: Plated<br>• Day 3: 2-3 undifferentiated colonies<br>• Day 6: 8-9 colonies mixture undifferentiated and differentiated | Surface:<br>Vita Alone – no ROCi<br>Source 2: iPS FGF on Feeders<br>Media Post – 8nM NM23-MM<br><br>• Day 1: Plated<br>• Day 3: 0 all floating<br>• Day 6: 5-6 colonies mixture undifferentiated and differentiated | Surface:<br>Vita + 2D6C3-no ROCi<br>Source: 2 iPS FGF on Feeders<br>Media Post – 8nM NM23-MM<br><br>• Day 1: Plated<br>• Day 3: 0 all floating<br>• Day 6: 5-6 colonies mixture undifferentiated and differentiated |

Fig. 8

| Surface:<br>Vita + 2D6C8<br>Source:<br>iPS NM23 on Matrigel<br>Media Post – 8nM NM23-MM<br><br>• Day 1: Plated<br>• Day 2: 2 undifferentiated colonies<br>• Day 4: 3-4 colonies undifferentiated or partially differentiated | Surface:<br>Vita + 2D6C3<br>Source:<br>iPS NM23 on Matrigel<br>Media Post – 8nM NM23-MM<br><br>• Day 1: Plated<br>• Day 2: 2 undifferentiated colonies<br>• Day 4: 3-4 colonies undifferentiated or partially differentiated | Surface:<br>Vita + ROC<br>Source:<br>iPS NM23 on Matrigel<br>Media Post – 8nM NM23-MM<br><br>• Day 1: Plated<br>• Day 2: 3 differentiated colonies<br>• Day 4: 3-4 colonies all partially or fully differentiated, slightly more differentiated than Vita + Ab No ROC |
|---|---|---|
| Surface:<br>Vita + 2D6C8<br>Source: H9s NM23 feeders<br>Media Post – 8nM NM23-MM<br><br>• Day 1: Plated<br>• Day 2: 3-4 small colonies, undifferentiated & partially differentiated<br>• Day 4: 8-10 colonies comparable or slightly more differentiated than Vita + ROC | Surface:<br>Vita + 2D6C3<br>Source: H9s NM23 feeders<br>Media Post – 8nM NM23-MM<br><br>• Day 1: Plated<br>• Day 2: 4-5 small colonies, undifferentiated & partially differentiated<br>• Day 4: 8-10 colonies comparable or slightly more differentiated than Vita + ROC | Surface:<br>Vita + ROC<br>Source: H9s NM23 feeders<br>Media Post – 8nM NM23-MM<br><br>• Day 1: Plated<br>• Day 2: 5-6 small undifferentiated colonies<br>• Day 4: 10-12 colonies mix of un and diff – only 3-4 still undifferentiated |

Fig. 10

2D6C3 Kappa Chain Variable Region

```
         FWR1                          CDR1
DIVITQTPLSLPVSLGDQASISCRSSQTIVHSNGNTYLE
         FWR2          CDR2
WYLQKPGQSPKLLIYKVSNRFSGVPDRFSGSGSG
         FWR3              CDR3
TDFTLKINRVEAEDLGVYYCFQGSHVPFT          (SEQ ID NO:59)
```

Fig. 13

2D6C3 Heavy Chain Variable Region

```
    -------- FWR1 --------------->  <--CDR1-->  <--
    EVMVVESGGGLVKPGGSLKLSCAASGFTFSGYAMSWVRQTPE
    FWR2 ------->  <------- CDR2 ------->  <---
    KRLEWVATISSGGTYIYYPDSVKGRFTISRDNAKNTLYLQMSSL
    FWR3 ------------->  <--- CDR3 --->
    RSEDTAMYYCARLGGDNYYEY        (SEQ ID NO:60)
```

Fig. 14

2D6C8 Kappa Chain Variable Region

```
         |————— FWR1 —————|————— CDR1 —————|
         DIVITQTPASLAVSLGQRATISYRASKSVSTSGYSYMHWN
         |——— FWR2 ———|— CDR2 —|————— FWR3 —————
         QQKPGQPPRLLIYLVSNLESGVPARFSGSGSGTDFTLNIH
         ————————|— CDR4 —|
         PVEEEDAATYYCQHIRELTRSE      (SEQ ID NO:61)
```

Fig. 15

2D6C8 Heavy Chain Variable Region

```
←———— FWR1 ————————→←— CDR1 —→←——
EVMVVESGGGLVKPGGSLKLSCAASGFTFSGYAMSWVRQTPE
— FWR2 —→←———— CDR2 ————→←—————————
KRLEWVATISSGGTYIYYPDSVKGRFTISRDNAKNTLYLQMSSL
——— FWR3 ————→←— CDR3 —→
RSEDTAMYYCARLGGDNYYEY     (SEQ ID NO:62)
```

Fig. 16

3C2B1 Kappa Chain Variable Region

```
      ←———— FWR1 ————→ ←———— CDR1 ————→ ←
      DIVLTQSPASLAVSLGQRATISCRASKSISTSDYNYIHWYQQK
      —— FWR2 ——→ ←— CDR2 —→ ←———————— FWR3 ————————
      PGQPPKLLIYLASNLESGVPARFSGSGSGTDFTLNIHPVEEED
      ————→ ←—— CDR3 ——→
      AATYYCQHSRELPLTF      (SEQ ID NO:63)
```

Fig. 17

3C2B1 Heavy Chain Variable Region

```
        ←――――――――― FWR1 ―――――――――→ ← CDR1 →←
        EVMLVESGGGLVKPGGSLKLSCAASGITFSTYTMSWVR
        ――― FWR2 ―――→ ←――――― CDR2 ―――――→ ←
        QTPEKRLEWVATISTGGDKTYYSDSVKGRFTISRDNAK
        ―――――― FWR3 ――――――→ ←――― CDR3 ―――→
        NNLYLQMSSLRSEDTALYYCARGTTAMYYYAM            (SEQ ID NO:64)
```

Fig. 18

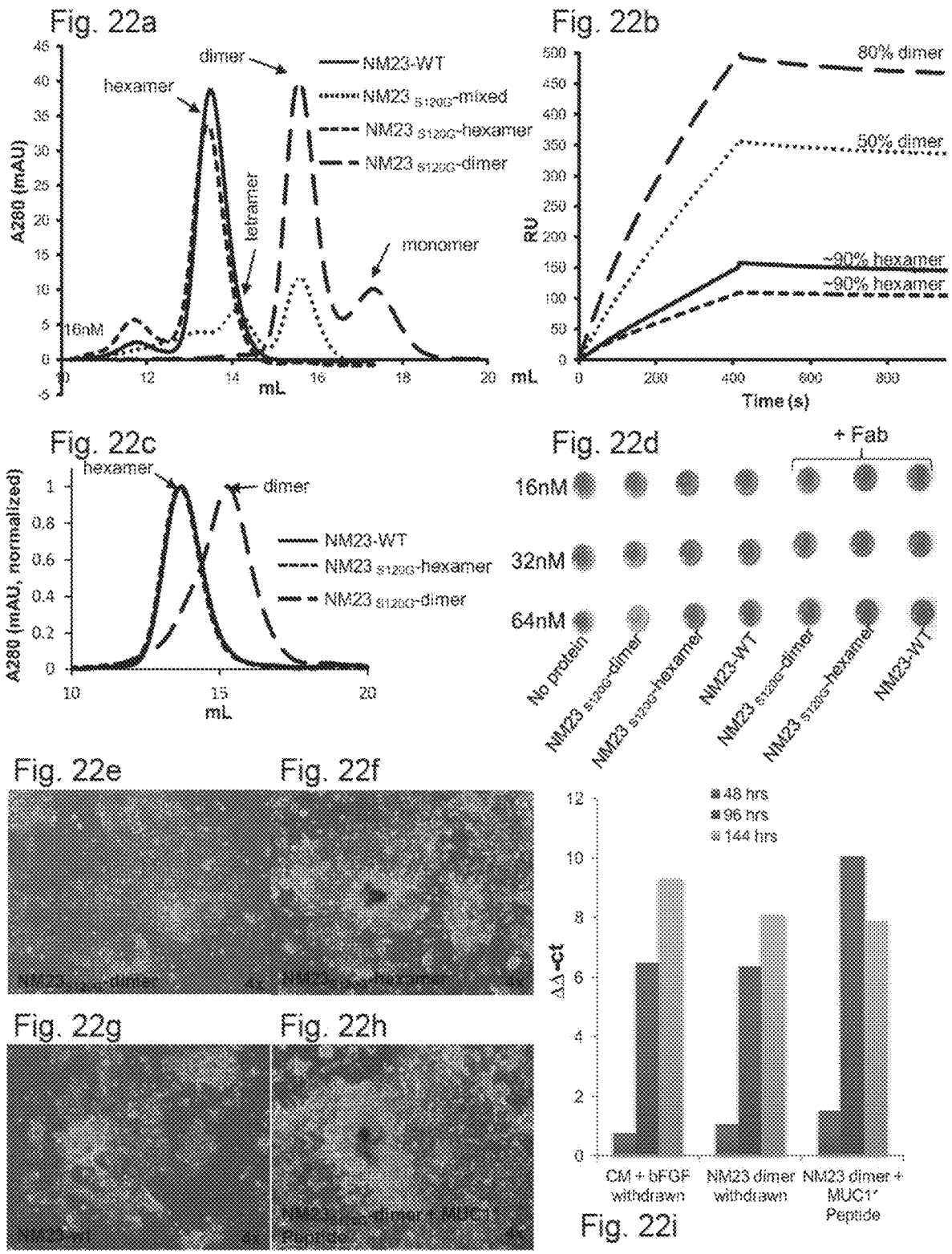

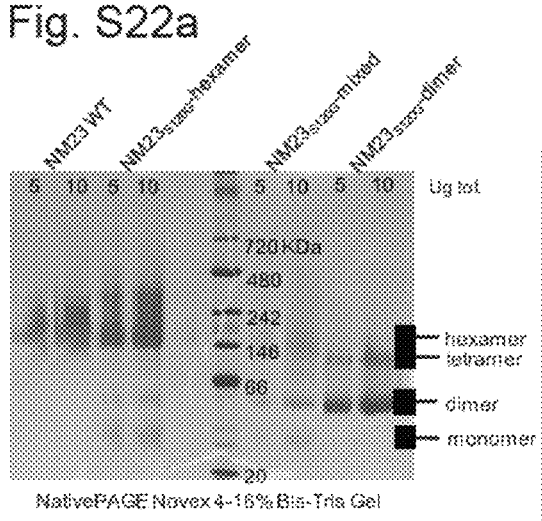
Fig. S22a
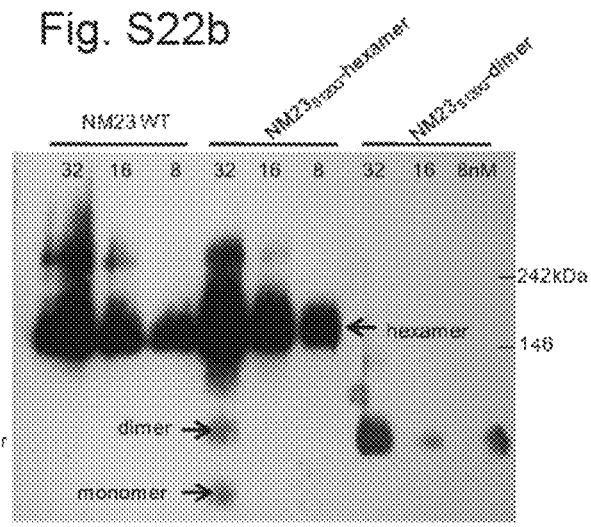
Fig. S22b
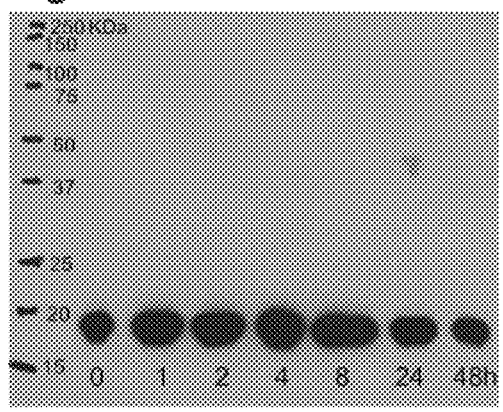
Fig. S22c

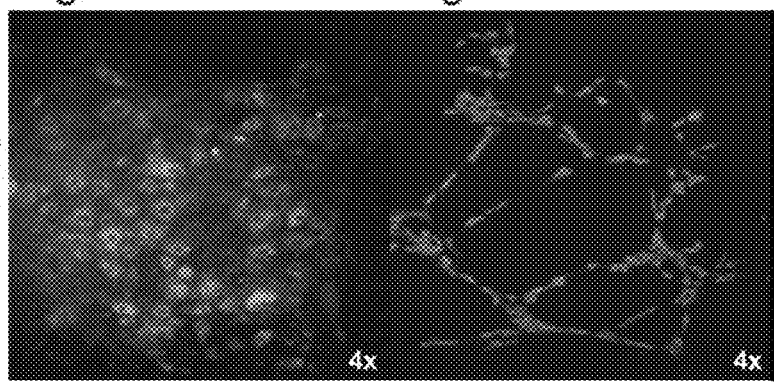
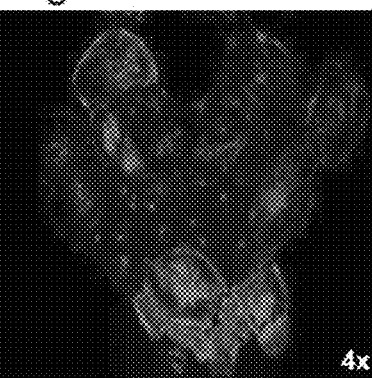
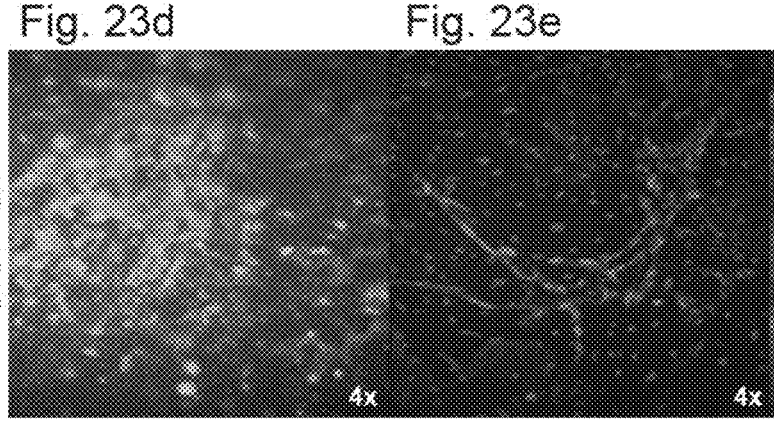
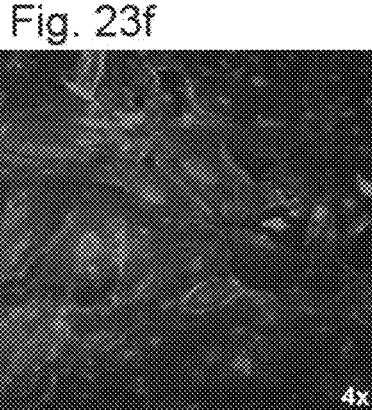
Fig. 23a Fig. 23b Fig. 23c
Alpha Feto Protein — Nestin — Smooth Muscle Actin
Fig. 23d Fig. 23e Fig. 23f

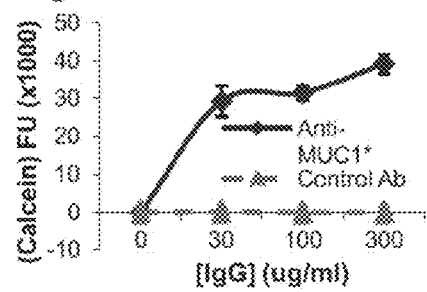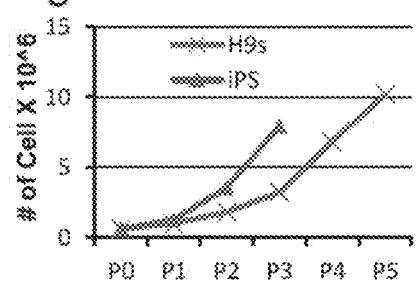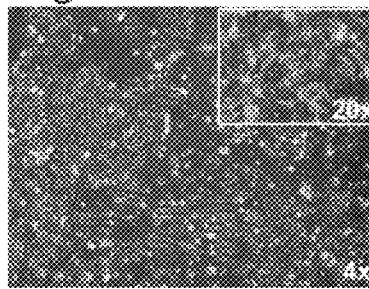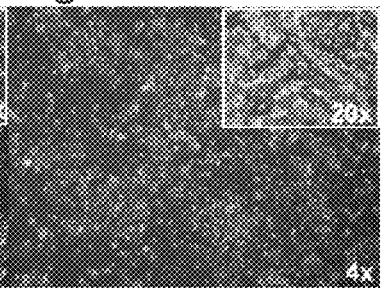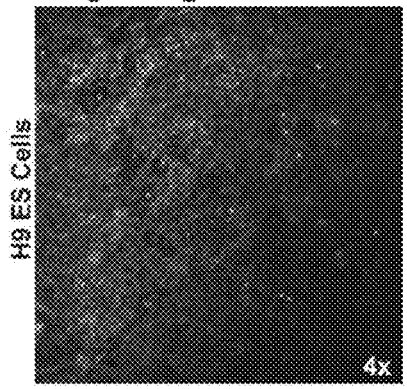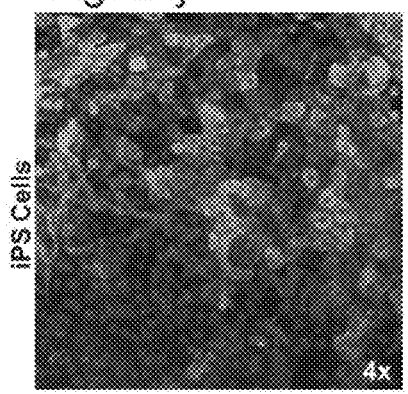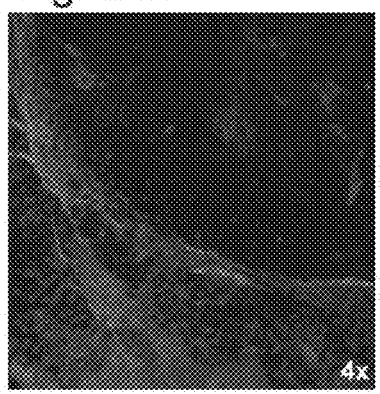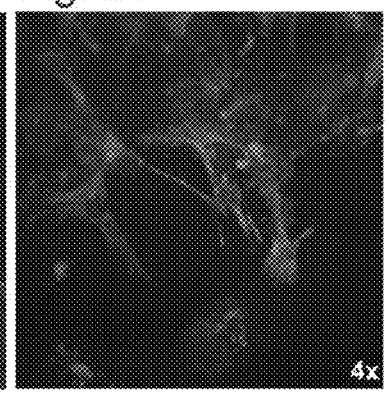

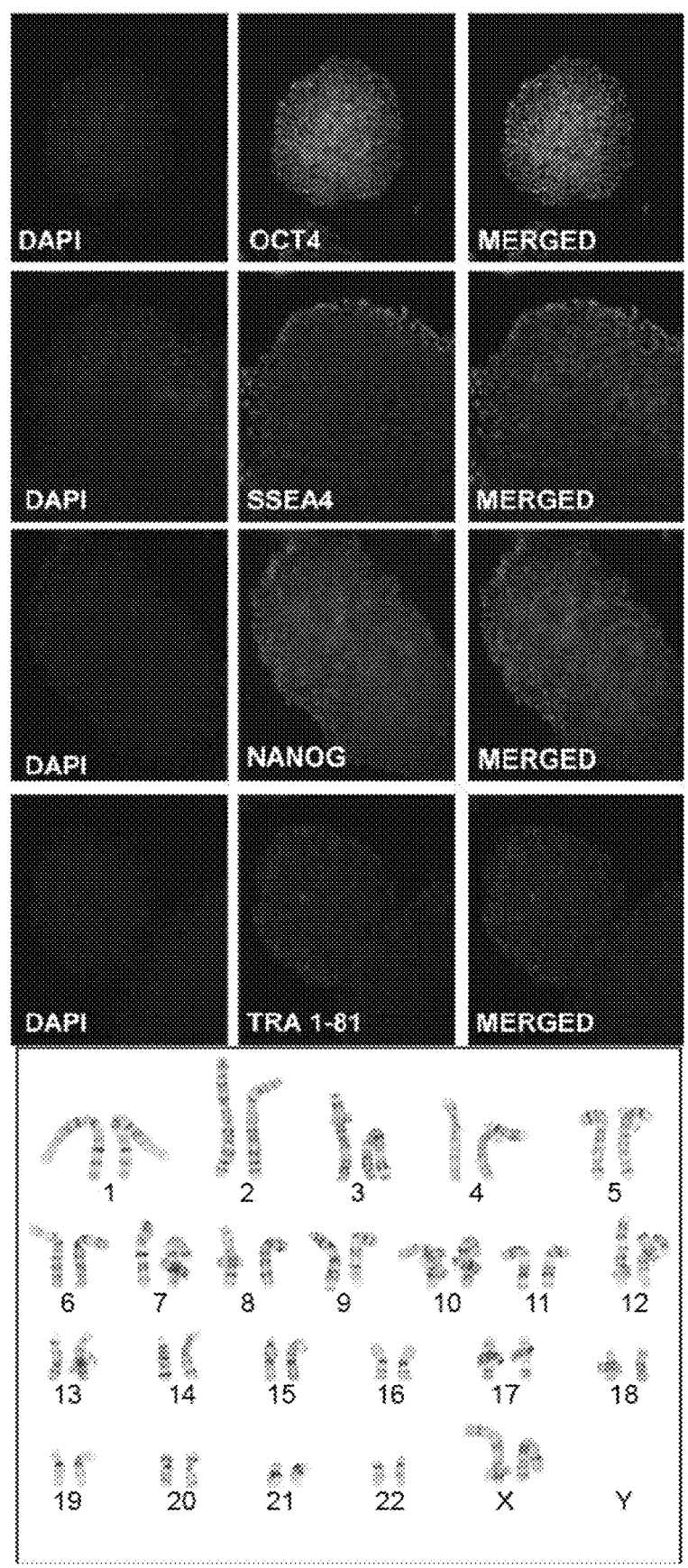
Fig. S24a

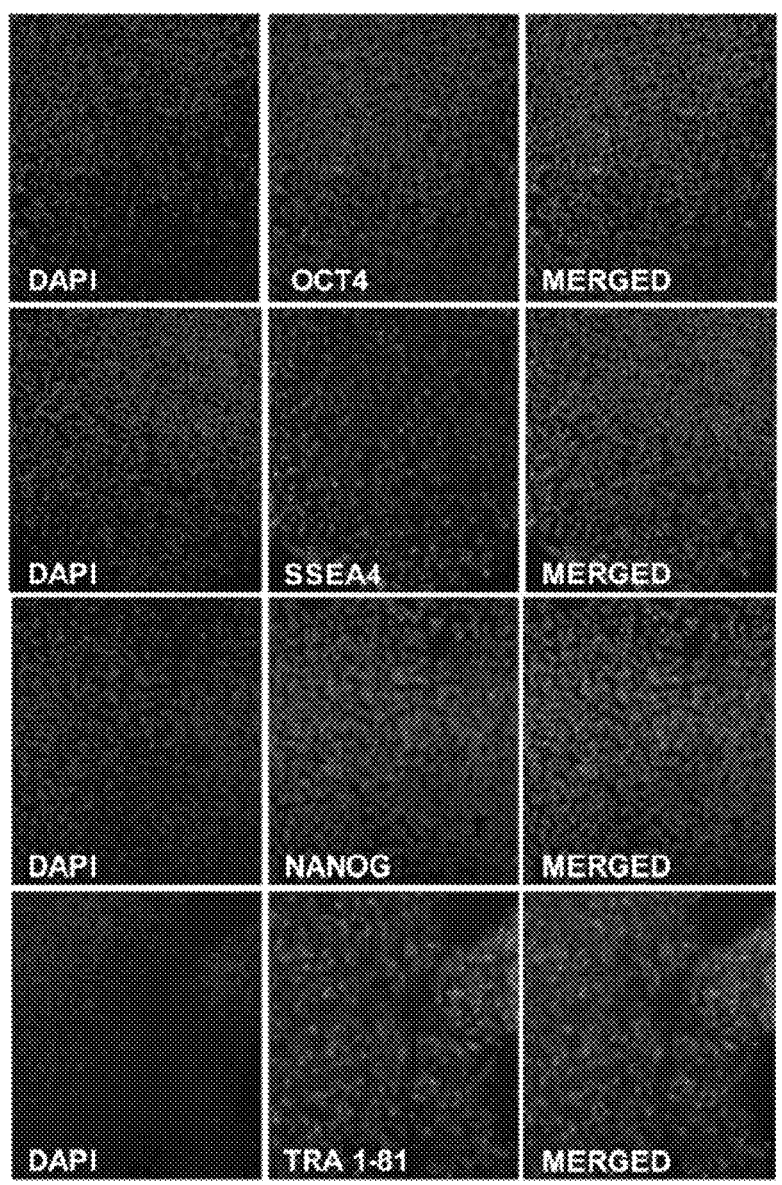
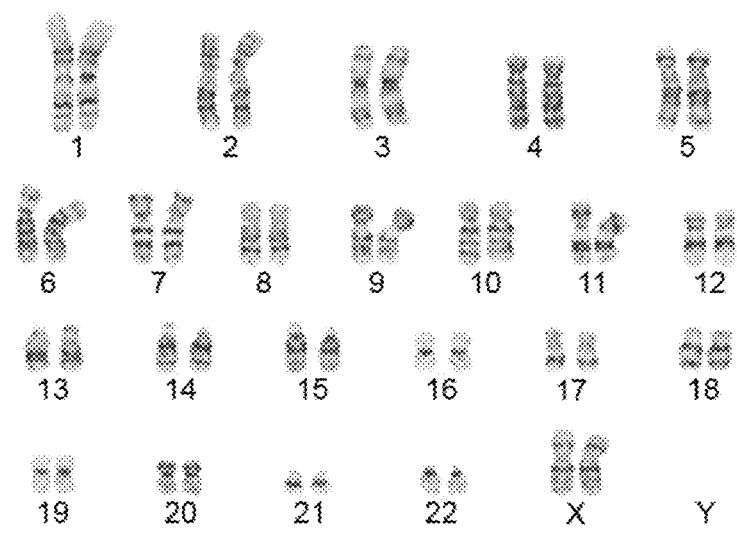
Fig. S24b

**MUC1* antibody surface**

Vitronectin Surface

METHOD FOR MAKING PLURIPOTENT STEM CELLS

CROSS-REFERENCE TO RELATED APPLICATIONS

The present application is a continuation of U.S. patent application Ser. No. 16/912,135, filed Jun. 25, 2020, now U.S. Pat. No. 12,049,618, which is a division of U.S. patent application Ser. No. 14/029,651, filed Mar. 19, 2012, now U.S. Pat. No. 10,724,027, which is a continuation of International Patent Application No. PCT/US12/29706, filed Mar. 19, 2012, which claims the benefit of U.S. Provisional Patent Application No. 61/474,236, filed Apr. 11, 2011, and claims the benefit of U.S. Provisional Patent Application No. 61/472,516, filed Apr. 6, 2011, and claims the benefit of U.S. Provisional Patent Application No. 61/453,917, filed Mar. 17, 2011, the contents of which are incorporated by reference in their entirety.

BACKGROUND OF THE INVENTION

Description of the XML File Submitted Electronically

The instant application contains a Sequence Listing which has been submitted electronically in XML format and is hereby incorporated by reference in its entirety. Said XML copy, created on Jun. 7, 2024, is named 56699-722.302.xml and is 92,451 bytes in size.

Field of the Invention

Human stem cells have traditionally been grown over layers of feeder cells because fibroblast feeder cells secrete as yet unknown factors that increase growth and inhibit spontaneous differentiation of stem cells. Later, in an effort to develop defined surfaces that enable stem cell growth, Matrigel was identified as a surface coating that supported stem cell growth if used in conjunction with bFGF and conditioned media (cell secretions) from fibroblast feeder cells. In an improvement, the present inventor previously determined that conditioned media from feeder cells was not required for stem cell growth, on Matrigel, if the stem cell growth media contained a MUC1* activator such as bivalent anti-MUC1* antibody or NM23 in dimeric form, preferably a mutant, such as NM23-S120G that preferentially forms dimers, while resisting the characteristic formation of tetramers and hexamers.

However, although stem cell growth over a layer of Matrigel is an improvement over a cell-based surface, it is not a defined or xeno-free surface, which is the end goal for the growth of human stem cells destined for therapeutic use. Matrigel is a mixture of components that are not desirable for cells destined for human transplant. Matrigel contains among other things mouse sarcoma cells. Therefore, those in the field appreciate that what is needed is a surface for stem cell growth that is defined and preferably xeno-free (free of animal material).

Several surfaces that are defined and xeno-free have been reported and some are commercially available. Vita™ surface (ThermoFisher, USA), hydrogel coated surfaces, and recombinant Vitronectin have been reported to facilitate stem cell attachment and growth. However they still require the use of feeder cell conditioned media. In addition, the degree of stem cell attachment has in general been less than what Matrigel supports. Another problem that plagues this field is that whenever stem cell growth media or surfaces are changed, the stem cells must adapt gradually. This period of adaptation can take weeks to months to change stem cell media or growth surface.

Recent research indicates that the mechanical nature of a surface impacts a stem cell's ability to remain pluripotent. For example, rigid surfaces have been shown to induce differentiation whereas more flexible surfaces inhibit spontaneous differentiation. Pressure is another factor that affects stem cell differentiation or resistance to differentiation. In addition to the mechanical characteristics of surfaces, the chemical nature of a surface has been shown to affect differentiation. Further, it has been reported that stem cells of different stages of differentiation have different binding preferences. That is, stem cells at one stage may attach and grow on a surface having certain chemical characteristics while stem cells at another stage do not bind to the first surface but attach and grow on a second surface having different chemical makeup than the first surface.

Therefore it would be an improvement over existing methods to develop defined surfaces for human stem cell growth and maintenance that enable stem cell attachment, and also promote pluripotent stem cell growth. A further improvement to the state of the art would be if these defined growth surfaces bound to ligands known to promote pluripotency. An even further improvement would be if a surface and growth media were developed to make an entirely defined system for pluripotent stem cell growth, even more preferred if the system could be free of animal products. It would be a vast improvement over the state of the art if methods could be identified that streamline stem cell adaptation so that growth media or growth surfaces can be changed without the typical 4-8 week acclimation period.

Recently researchers (J. Nichols and A. Smith, *Cell Stem Cell* 4 (6), 487 (2009), J. Hanna, A. W. Cheng, K. Saha et al., *Proc Natl Acad Sci USA* 107 (20), 9222 (2010).) reported that human stem cells grown by conventional methods are not truly pluripotent stem cells, but have already undergone differentiation to a more mature state called "primed." Primed stem cells grow via the bFGF/TGF-beta pathway and closely resemble mouse stem cells derived from the epiblast rather than the "naïve" or "ground state" mouse stem cells that are derived from the inner cell mass. The consensus from the early research in the area of naïve versus primed human stem cells is that: 1) human naïve stem cells are not stable in the presence of bFGF; and 2) the growth factors or pathway by which human naïve stem cells growis as yet unknown.

Research has now shown that human stem cells cultured in bFGF containing media are no longer truly pluripotent (J. Hanna, A. W. Cheng, K. Saha et al., *Proc Nal Acad Sci USA* 107 (20), 9222 (2010)). In a watershed research article, Jaenisch and colleagues describe human embryonic stem (ES) cells as being "primed" rather than being true pluripotent stem cells, which they term "Naïve". Research has now shown that human stem cells in the naïve state cannot be maintained in standard stem cell growth media wherein the major growth factor is bFGF.

By comparing human ES cells to mouse ES cells wherein both were derived from the blastocyst-stage embryos, the researchers discovered that the human ES cells were morphologically and molecularly different from the mouse stem cells. They further disclosed that the human ES cells that have been isolated thus far are not truly pluripotent and more closely resemble mouse stem cells that have been derived from the epiblast stage which is a later stage of development. These findings and others indicate that what we think of as human pluripotent ES cells are actually more mature than true pluripotent stem cells. Jaenisch and colleagues discovered molecular markers that identify naïve stem cells and markers that identify primed stem cells.

Researchers were able to temporarily make human primed stem cells revert to the naïve state by ectopic induction of Oct4, Klf4, and Klf2 factors combined with LIF and inhibitors of glycogen synthase kinase 33 (GSK30) and mitogen-activated protein kinase (ERK1/2) pathway. Forskolin, a protein kinase A pathway agonist which can induce Forskolin, a protein kinase A pathway agonist which can induce Klf4 and Klf2 expression, transiently replaced the need for ectopic expression of those two genes. Once the human ES cells had been reverted to the naïve state, they needed to be cultured in PD/CH/LIF/FK but could only remain naïve for a few passages before they matured to primed cells. This is strong evidence that the researchers were not able to identify the growth factors that promote and maintain human ES cells in the pluripotent naïve state. In contrast to conventional human ESCs, these epigenetically converted naïve stem cells gained expression of Oct4, Nanog, Klf4, Klf2, Tbx3, Gbx2, Lin28 and SOCS3 (Naïve markers), and lost or had greatly reduced expression of Otx2, Sox17, Cer1, Foxa2, Zic1, Lhx2 and XIST (Primed markers). In addition, primed cells that were transiently reverted to the naïve state grew in sheets rather than in colonies.

However, Nichols and Smith report that the Naïve markers are Oct4, Nanog, Klf4, Klf2, Rex1 and NrOb1 and that naïve cells had lost or had greatly reduced expression of FGF5 and markers of X-inactivation such as XIST. The discrepancy between the lists of naïve markers and primed markers generated by these two research teams may be due differences in the naïve stem cells they were analyzing; Hanna et al analyzed primed human stem cells that they had transiently reverted to the naïve state, determined by their similarity to mouse naïve stem cells. Alternatively, genes identified by the earlier research may cause activation of the genes identified in the later, more extensive studies described in Hanna et al. Both studies agree that the naïve markers consist at least of Oct4, Nanog, Klf4 and Klf2, and the primed markers consist at least of FOXa2 and XIST.

Previous research has not been able to identify the growth pathway or the growth factor(s) that made human stem cells propagate as naïve stem cells. Further, even with ectopic expression of genes and growth in a concoction of factors, the reverted-naïve cells remained naïve for a short period of time and then progressed to the more differentiated primed stage.

It would be a significant improvement if one could identify methods for cultivating naïve stem cells. Such methods would include identification of the growth pathways that stimulate growth and maintenance of the naïve state, development of media that enables their proliferation, or identification of surfaces that naïve stem cells bind to for growth or isolation of naïve stem cells.

Therefore what is needed is a method for propagating human stem cells as naïve stem cells directly after harvest from either an embryo or from an induced pluripotent state, or a method to revert primed stem cells to the naïve state and then maintain them in that state for prolonged periods of time. What is needed is a method for stably converting primed stem cells to the naïve state, whereas current methods can only transiently hold the cells in the naïve state. Ideally, the method for maintaining human stem cells in the naïve state or converting them from the primed state to the naïve state would not involve ectopic expression of genes.

SUMMARY OF THE INVENTION

In one aspect, the present invention is directed to a method for inducing cells to gain characteristics of naïve stem cell state comprising culturing the cells in the presence of a MUC1* activator. The cells may be human cells, stem cells, human stem cells, progenitor cells, embryonic in origin or are induced to become more stem-like. The cells may be human cells derived from a blastocyst.

In this method, the MUC1* activator may be a dimeric or bivalent molecule, such as NM23 or an NM23 mutant or variant, or a bivalent antibody or antibody variant.

The cells may be cultured in the presence of human feeder cells or their secretions. The feeder cells may be fibroblasts or cancer cells, or the feeder cells are growth inactivated.

The present invention is also directed to a method for maintaining naïve stem cells in naïve stem cell state comprising culturing the cells in the presence of a MUC1* activator.

In another aspect, the present invention is directed to a method for establishing human stem cell lines comprising withdrawing cells from a blastocyst and culturing the cells in the presence of NM23 or dimeric NM23.

In yet another aspect, the present invention is directed to a method for inducing cells to gain characteristics of naïve stem cell state or maintaining the naïve stem cells in the naïve stem cell state comprising attaching the cells to be induced or cells possessing the naïve stem cell state to a stem proliferation surface lacking a feeder layer. The surface may include from at least about 0.5% Nitrogen (N), at least about a sum of Oxygen (O) and Nitrogen (N) of greater than or equal to 17.2%, and a contact angle of at least about 13.9 degrees. The surface may include 1.7-2.1% Nitrogen, 26.4-28.7% Oxygen and 28.2-30.7% Nitrogen and Oxygen combined, and wherein the surface has a contact angle of 14.3-18.8 degrees. The surface may be Vita™ surface (ThermoFisher, USA).

In yet another aspect, the invention is directed to a method for selecting for cells that have increased expression of naïve cell markers, comprising exposing a population of cells suspected of containing cells with increased expression of naïve markers to a stem proliferation surface lacking a feeder layer, and culturing the selected cells in the presence of the surface. The surface may include from at least about 0.5% Nitrogen (N), at least about a sum of Oxygen (O) and Nitrogen (N) of greater than or equal to 17.2%, and a contact angle of at least about 13.9 degrees. The surface may include 1.7-2.1% Nitrogen, 26.4-28.7% Oxygen and 28.2-30.7% Nitrogen and Oxygen combined, and wherein the surface has a contact angle of 14.3-18.8 degrees. The surface may be Vita™ surface (ThermoFisher, USA).

In any of method described above, the surface additionally may include an agent that binds to a cell surface molecule that is present on stem cells or progenitor cells. The cell surface molecule may be MUC1 or MUC1*. The cell surface molecule may be PSMGFR sequence. The agent may be an antibody. The antibody may be a polyclonal or monoclonal antibody that binds to PSMGFR. In particular, the monoclonal antibody may have the following Kappa Chain Variable Region CDR sequences:

```
CDR1:
                               (SEQ ID NO: 20)
RSSQTIVHSNGNTYLE;

CDR2:
                               (SEQ ID NO: 21)
KVSNRFS; and

CDR3:
                               (SEQ ID NO: 22)
FQGSHVPFT, or

CDR1:
                               (SEQ ID NO: 26)
RASKSVSTSGYSYMH;

CDR2:
                               (SEQ ID NO: 27)
LVSNLES ; and

CDR3:
                               (SEQ ID NO: 28)
QHIRELTRSE.
```

According to the method above, the agent may be a polyclonal or monoclonal antibody that binds to SSEA1, SSEA4, Tra 1-60, Tra 1-81 or CD34. The mentioned agent may be NM23 or NM23 mutant or variant and is dimeric or bivalent.

In any of the above described methods, the methods may be carried out in the absence of a Rho kinase inhibitor. The methods may include trypsinizing the cells to single cells prior to plating on the surface. And the cells may be plated on the surface at a low density, such as between about 1×10³ cells per cm² and 1×10⁴ cells per cm² of a defined structure. In particular, the cells may be plated at about 5263 cells per cm² of a defined structure.

In another aspect, the methods may include plating the cells on the surface at a low volume of media, preferably a volume of media to just coat the surface, which volume of media may be between 0.1 and 0.2 mLs per cm² of a defined structure. The cells may be plated on the cells on the surface in the presence of EDTA. Further the method may include bringing the plated cells into close contact with the surface by application of force. The force may be centrifugal force.

In another aspect, the invention is directed to an article comprising a stem cell proliferation surface without feeder layer, to which is bound an agent that binds to a cell surface molecule that is present on stem cells or progenitor cells.

The surface may include from at least about 0.5% Nitrogen (N), at least about a sum of Oxygen (O) and Nitrogen (N) of greater than or equal to 17.2%, and a contact angle of at least about 13.9 degrees. The surface may be Vita or Vita-like surface. The cell surface molecule may be MUC1 or MUC1*. The cell surface molecule may be PSMGFR sequence. The agent may be an antibody. The antibody may be a polyclonal or monoclonal antibody that binds to PSMGFR. In particular, the monoclonal antibody may have the following Kappa Chain Variable Region CDR sequences:

```
CDR1:
                               (SEQ ID NO: 20)
RSSQTIVHSNGNTYLE;

CDR2:
                               (SEQ ID NO: 21)
KVSNRFS; and
```

```
                   -continued
CDR3:
                               (SEQ ID NO: 22)
FQGSHVPFT, or

CDR1:
                               (SEQ ID NO: 26)
RASKSVSTSGYSYMH;

CDR2:
                               (SEQ ID NO: 27)
LVSNLES ; and

CDR3:
                               (SEQ ID NO: 28)
QHIRELTRSE.
```

The agent may be a polyclonal or monoclonal antibody that binds to SSEA1, SSEA4, Tra 1-60, Tra 1-81 or CD34. The mentioned agent may be NM23 or NM23 mutant or variant and is dimeric or bivalent.

In another aspect, the invention include a method for identifying microRNAs signatures that are characteristic of the naïve stem cell state or the primed stem cell state comprising:
  (i) culturing human embryonic stem cells or induced pluripotent stem cells in the presence of NM23 dimer or bivalent variants;
  (ii) attaching the cells to a stem cell proliferation surface coated with a MUC1* antibody and allowing the cells to grow;
  (iii) harvesting the cells and identifying microRNAs expressed from the stem cells of step (ii);
  (iv) separately culturing human embryonic stem cells or induced pluripotent stem cells in bFGF-based media over a layer of murine feeder cells;
  (v) harvesting the cells and identifying microRNAs expressed from the cells of step (iv);
  (vi) comparing the microRNAs identified in step (iii) with the microRNAs identified in step (v);
  (vii) identifying microRNAs unique to the naïve cell state by identifying those present or that have increased expression in step (iii) that are absent or have reduced expression in step (v); and
  (viii) identifying microRNAs unique to the primed cell state by identifying those present in step (v) that are absent or have reduced expression in step (iii).

The stem cell proliferation surface may be Vita or Vita-like surface.

In yet another aspect, the invention is directed to a method for identifying microRNAs signatures that are characteristic of the naïve stem cell state or the primed cell state comprising:
  (i) culturing a first set and second set of human embryonic stem cells or induced pluripotent stem cells in the presence of NM23 dimer or bivalent variants;
  (ii) attaching the cells to a first stem cell proliferation surface coated with a MUC1* antibody;
  (iii) measuring the levels of microRNAs in the first set of cells;
  (iv) harvesting the cells of the second identical set of cells, and plating the second set of cells onto second stem cell proliferation surface;
  (v) allowing a period of growth over the second stem cell proliferation surface;
  (vi) measuring the levels of microRNAs in the second set of cells;
  (vii) identifying microRNAs unique to the naïve stem cell state comprising identifying those present or that have increased expression in the first set of cells and absent from or that have decreased expression in the second set of cells; and (viii) identifying microRNAs unique to the primed cell state by identifying those present or that have increased expression in the second set of cells and absent from or that have decreased expression in the first set of cells.

The first stem cell proliferation surface may be Vita or Vita-like surface, and the second stem cell proliferation surface may be Vitronectin.

In yet another aspect, the invention is directed to a method for inducing cells to gain characteristics of naïve stem cell state comprising introducing microRNAs that are characteristic of the naïve state to cells.

In yet another aspect, the invention is directed to a method for treating or preventing cancer in a patient, comprising administering to the patient, a protein or nucleic acid, which is upregulated when cells transition from the naïve state to a more differentiated state. The nucleic acid may be microRNA. The differentiated state of a cell may be the primed state.

In yet another aspect, the invention is directed to a method for culturing stem cells or progenitor cells on a stem cell proliferation surface comprising:
 (a) obtaining a sample of the stem cells or progenitor cells;
 (b) contacting the stem cells or progenitor cells to the surface; and
 (c) culturing the stem cells or progenitor cells in a media that contains a first agent that dimerizes MUC1*.

In yet another aspect, the invention is directed to a method for adapting stem cells or progenitor cells to bind to a surface comprising:
 (a) pre-incubating the stem cells or progenitor cells in media that contains a first agent that dimerizes MUC1*; and
 (b) contacting the stem cells or progenitor cells to the surface.

The surface may include a second agent that dimerizes MUC1*.

The above method may further include the following steps after step (a), and before step (b),
 (a)(i) pelleting the stem cells or progenitor cells after incubation in the media that contains the first agent that dimerizes MUC1*;
 (a)(ii) resuspending the stem cells or progenitor cells in media lacking the first agent;
 (a)(iii) plating the stem cells or progenitor cells on the surface; and
 (a)(iv) waiting for a period of up to 48 hrs.

In yet another aspect, the invention is directed to a method for adapting stem cells to bind to a stem cell proliferation surface lacking a feeder layer, comprising pre-incubating the cells in media that contains an agent that dimerizes MUC1*, and then introducing the stem cells to the surface. The surface may include from at least about 0.5% Nitrogen (N), at least about a sum of Oxygen (O) and Nitrogen (N) of greater than or equal to 17.2%, and a contact angle of at least about 13.9 degrees.

The method above may include additional steps of
 (i) incubating the stem cells in media that contains an agent that dimerizes MUC1*;
 (ii) subjecting the stem cells to a force that causes the cells to contact the surface before attaching to other cells;
 (iii) resuspending the cells in media lacking the agent;
 (iv) plating onto the surface;
 (v) waiting period of up to 48 hrs; and
 (vi) adding an agent that dimerizes MUC1*.

The surface may be Vita™ surface (ThermoFisher, USA). The force may be centrifugal force, pressure, or vacuum.

In yet another aspect, the invention is directed a kit comprising:
 (i) an article comprising a stem cell proliferation surface without feeder layer, to which is bound an agent that binds to a cell surface molecule that is present on stem cells or progenitor cells; and
 (ii) stem cell growth media comprising minimal media with NM23.

The surface comprises from at least about 0.5% Nitrogen (N), at least about a sum of Oxygen (O) and Nitrogen (N) of greater than or equal to 17.2%, and a contact angle of at least about 13.9 degrees. The surface may be Vita™ surface (ThermoFisher, USA). The cell surface molecule may be MUC1 or MUC1*. The cell surface molecule may be PSMGFR sequence. The agent may be an antibody. The antibody may be a polyclonal or monoclonal antibody that binds to PSMGFR. In particular, the monoclonal antibody may have the following Kappa Chain Variable Region CDR sequences:

```
CDR1:
                                    (SEQ ID NO: 20)
      RSSQTIVHSNGNTYLE;

CDR2:
                                    (SEQ ID NO: 21)
      KVSNRFS; and

CDR3:
                                    (SEQ ID NO: 22)
      FQGSHVPFT, or

CDR1:
                                    (SEQ ID NO: 26)
      RASKSVSTSGYSYMH;

CDR2:
                                    (SEQ ID NO: 27)
      LVSNLES ; and

CDR3:
                                    (SEQ ID NO: 28)
      QHIRELTRSE.
```

According to the method above, the agent may be a polyclonal or monoclonal antibody that binds to SSEA1, SSEA4, Tra 1-60, Tra 1-81 or CD34. The mentioned agent may be NM23 or NM23 mutant or variant and is dimeric or bivalent. The antibody may be humanized. And the minimal media may be xeno-free.

These and other objects of the invention will be more fully understood from the following description of the invention, the referenced drawings attached hereto and the claims appended hereto.

DESCRIPTION OF THE DRAWINGS

The present invention will become more fully understood from the detailed description given herein below, and the accompanying drawings which are given by way of illustration only, and thus are not limitative of the present invention, and wherein;

FIG. 1 is the experimental setup and noted results, shown in 6-well plate format, for the experiment described in Example 3 and for which images of the 6 wells are shown in FIGS. 2-4.

FIG. 5 is the experimental setup and noted results, shown in 6-well plate format, for another experiment described in Example 3 and for which images of the 6 wells are shown in FIGS. 6 and 7. The point of this experiment is to test if reducing media volume aids in the attachment of stem cells to surfaces and further if withholding MUC1* ligands from the media also aids in attachment of cells to the MUC1* antibodies on the surface.

FIG. 8 is the experimental setup and noted results, shown in 6-well plate format, for another experiment described in Example 3 and for which images of the 6 wells are shown in FIG. 9. In this experiment, 2 monoclonal anti-MUC1* antibodies are compared to a Vita surface alone. Human iPS cells from 2 different sources are tested: iPS cells that had previously been cultured in NM23-MM and iPS cells that had previously been cultured in bFGF plus MEF conditioned media, both over Matrigel.

FIG. 10 is the experimental setup and noted results, shown in 6-well plate format, for the experiment described in Example 4 and for which images of the 6 wells are shown in FIG. 11.

FIG. 13 shows amino acid sequence for the 2D6C3 Kappa Chain Variable Region. CDR1: RSSQTIVHSNGNTYLE (SEQ ID NO:20); CDR2: KVSNRFS (SEQ ID NO:21); and CDR3: FQGSHVPFT (SEQ ID NO:22).

FIG. 14 shows amino acid sequence for the 2D6C3 Heavy Chain Variable Region. CDR1: GYAMS (SEQ ID NO:23); CDR2: TISSGGTYIYYPDSVKG (SEQ ID NO:24); and CDR3: LGGDNYYEY (SEQ ID NO:25).

FIG. 15 shows amino acid sequence for the 2D6C8 Kappa Chain Variable Region. CDR1: RASKSVSTSGYSYMH (SEQ ID NO:26); CDR2: LVSNLES (SEQ ID NO:27); and CDR3: QHIRELTRSE (SEQ ID NO:28).

FIG. 16 shows amino acid sequence for the 2D6C8 Heavy Chain Variable Region. CDR1: GYAMS (SEQ ID NO:29); CDR2: TISSGGTYIYYPDSVKG (SEQ ID NO:30); and CDR3: LGGDNYYEY (SEQ ID NO:31).

FIG. 17 shows amino acid sequence for the 3C2B1 Kappa Chain Variable Region.
CDR1: RASKSISTSDYNYIH (SEQ ID NO:32); CDR2: LASNLES (SEQ ID NO:33); and CDR3: QHSRELPLTF (SEQ ID NO:34).

FIG. 18 shows amino acid sequence for the 3C2B1 Heavy Chain Variable Region. CDR1: TYTMS (SEQ ID NO:35); CDR2: TISTGGDKTYYSDSVKG (SEQ ID NO:36); and CDR3: GTTAMYYYAM (SEQ ID NO:37).

FIGS. 22a-22i show the results of the experiments described in Example 7. a) is an overlay of FPLC traces showing the multimerization state of recombinant NM23 wild type (wt), NM23-S120G-hexamer which was the soluble fraction of the expressed protein, the NM23-S120G-dimer that was denatured and refolded according to Example 7 to produce mostly dimers, and NM23-S120G-mixed which was a mixture of the hexamers, tetramers and dimers was generated such that it contained ~50% dimer. b) is an overlay of Surface Plasmon Resonance (SPR) traces from experiments that tested the ability of the NM23 preparations shown in part (a) to determine their ability to bind to a synthetic MUC1* extra cellular domain (ecd) peptide (PSMGFR). The amount of NM23 binding to the MUC1* peptide corresponds to the concentration of dimer present in each sample. c) is an overlay of FPLC traces characterizing recombinant NM23-wt, $NM23_{S120G}$-hexamer and $NM23_{S120G}$-dimer containing the Strep-tag II. d) is a photograph of a nanoparticles experiment testing the ability of the various NM23 multimers to bind to the MUC1*ecd peptide (PSMGFR-His tagged) that was immobilized onto gold NTA-Ni-SAM-coated nanoparticles. A nanoparticle color change from pink to blue/gray indicates binding. (e-h) shows the functional effect of the various NM23 multimers on stem cell pluripotency. Loss of pluripotency is seen as dark or thickened areas of cells. i) is a graph of the measured amounts of microRNA-145 in response to withholding bFGF, NM23-dimers or competitively inhibiting the NM23-dimer-MUC1* interaction. An increase in miR-145 signals the cell's exit from pluripotency and onset of differentiation.

FIGS. S22a-S22c show gels and Western blots showing the multimerization state (a,b) of the various NM23 preparations and the stability of NM23-dimers (c).

FIGS. 23a-23f show photos of experiment of Example 8 where human H9 ES cells that have been grown over Matrigel and cultured in either NM23-MM (top) or bFGF-MEF conditioned media (bottom) for 5 or more passages then allowed to differentiate by the embryoid body method, then stained for presence of the three germline markers plus the nuclear stain DAPI (blue). The figure shows that NM23 causes the stem cells to grow in such a way that they differentiate better than cells grown in bFGF as evidenced by cell morphology and their coordinated differentiation.

FIGS. 24a-24l show graphs and photos of the experiments described in Example 9 showing that human ES and iPS cells undergo exponential growth on Vita-type surfaces that have been coated with an anti-MUC1* antibody and wherein the cells are cultured in a NM23-based media. Photos further show that after serial passaging, these cells differentiate down all three germlines.

FIGS. S24a-S24b show photos of immunocytocellular (ICC) staining for the presence of the pluripotency markers for the human ES (a) and iPS (b) cells shown in FIG. 24 and described in Example 9 and karyotyping analysis showing unchanged karyotype.

FIGS. 25a-25d show graphs of RT-PCR experiments to measure the expression levels of naïve and primed markers for human ES cells grown under a variety of conditions which are described in Example 10.

FIGS. 26a-26l show photos of human ES cells cultured in the presence or absence of a Rho kinase inhibitor (ROCi) wherein the stem cells were cultured in NM23-MN6. FIGS. 26m-26t show images of human ES cells cultured in either NM23-MM or NM23-MN6 plus or minus the ROCi over a layer of Vitronectin.

Figure 27:
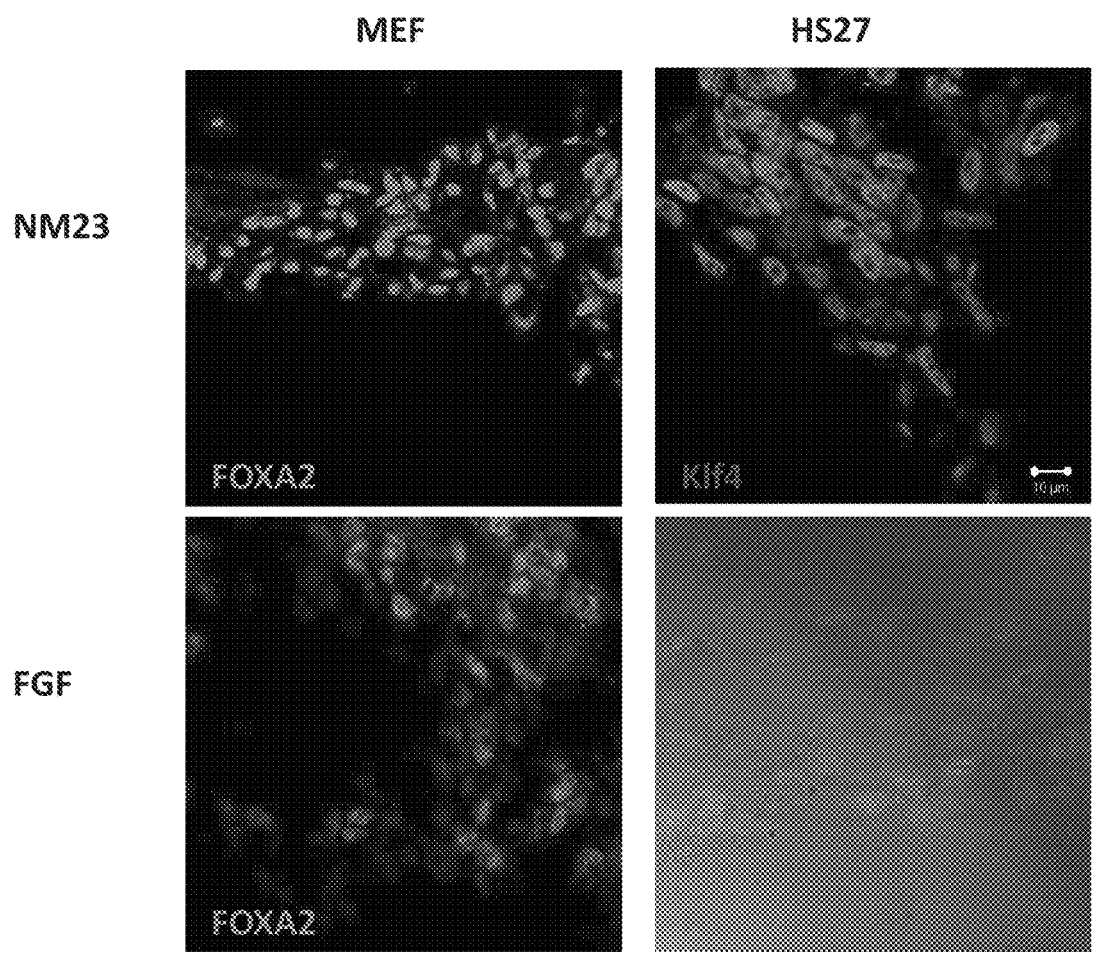

FIG. 27 shows images from a confocal microscope of H9 stem cells that have been grown in NM23-S120G over either human HS27 feeder cells or over mouse MEF feeder cells; also shows H9 stem cells that have been grown in bFGF over either human HS27 feeder cells or over mouse MEF feeder cells. Only NM23-S120G cultured cells grown over human feeders stained positive for Klf4 showing they are naïve. All other conditions produced primed stem cells and stained positive for Foxa2, a marker for primed cells.

Figure 28:
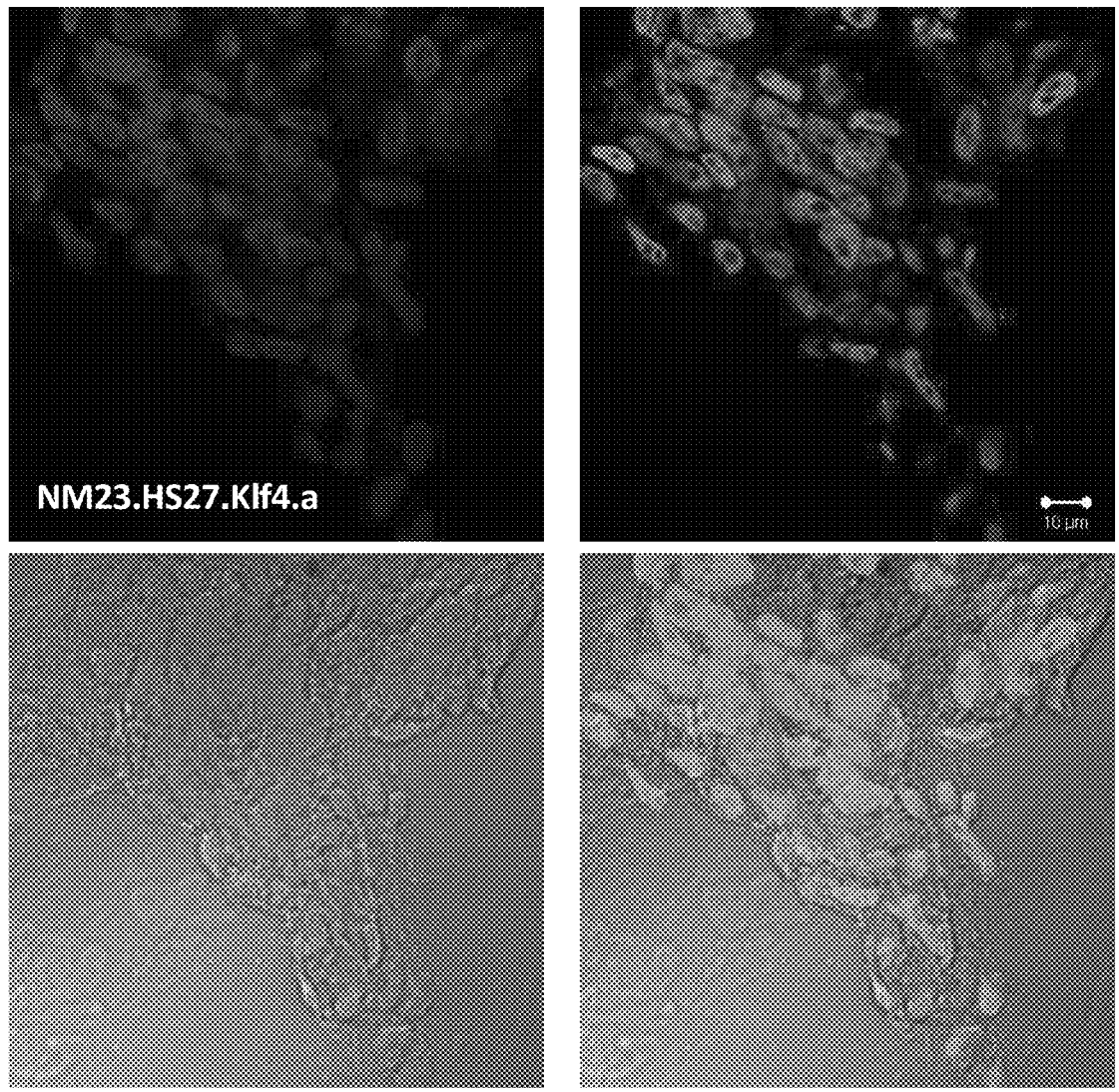

FIG. 28 is an image from a confocal microscope of H9 stem cells that have been grown in NM23-S120G over human feeder cells and stain positive for Klf4 which is a marker for naïve stem cells.

Figure 29:
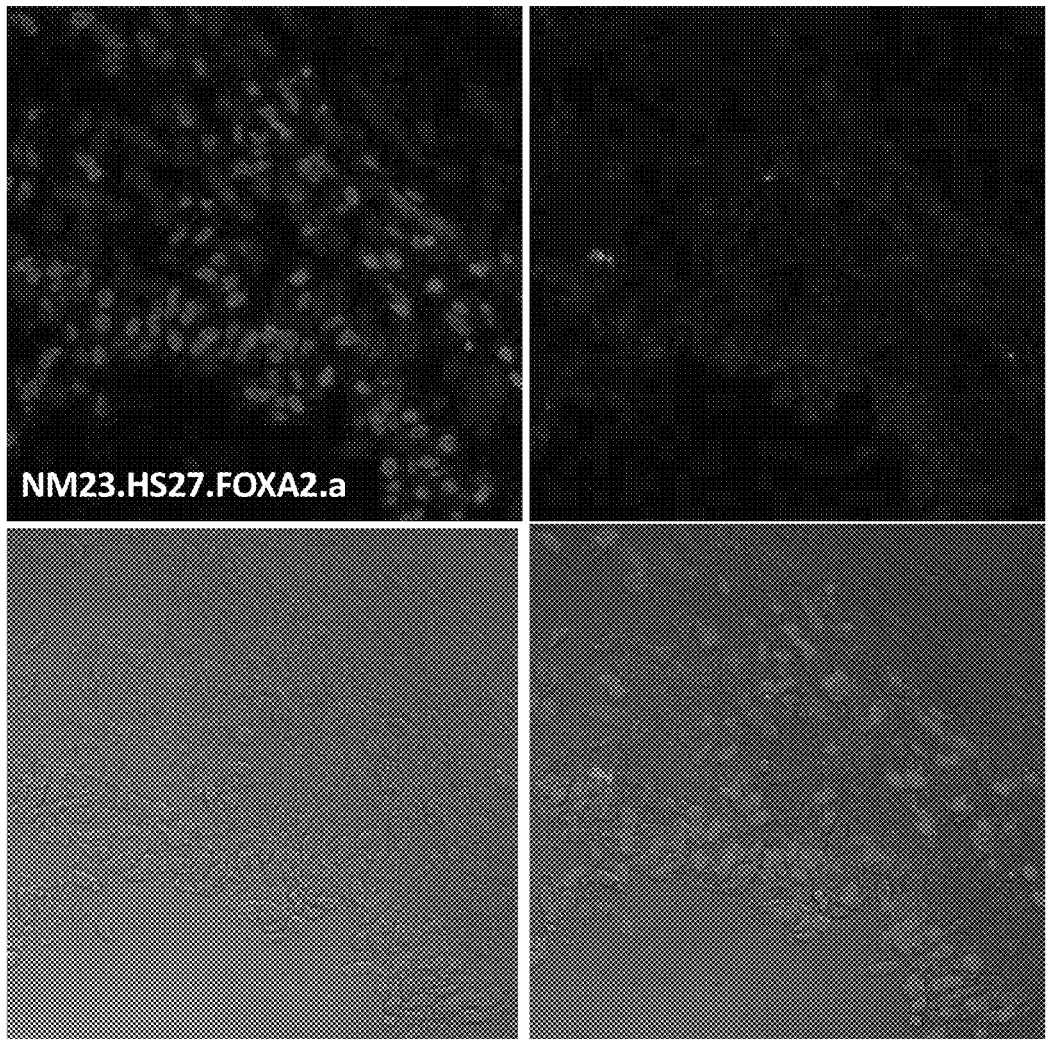

FIG. 29 is an image from a confocal microscope of H9 stem cells that have been grown in NM23-S120G over human feeder cells and shows they are negative for Foxa2 a marker for primed stem cells.

Figure 30:
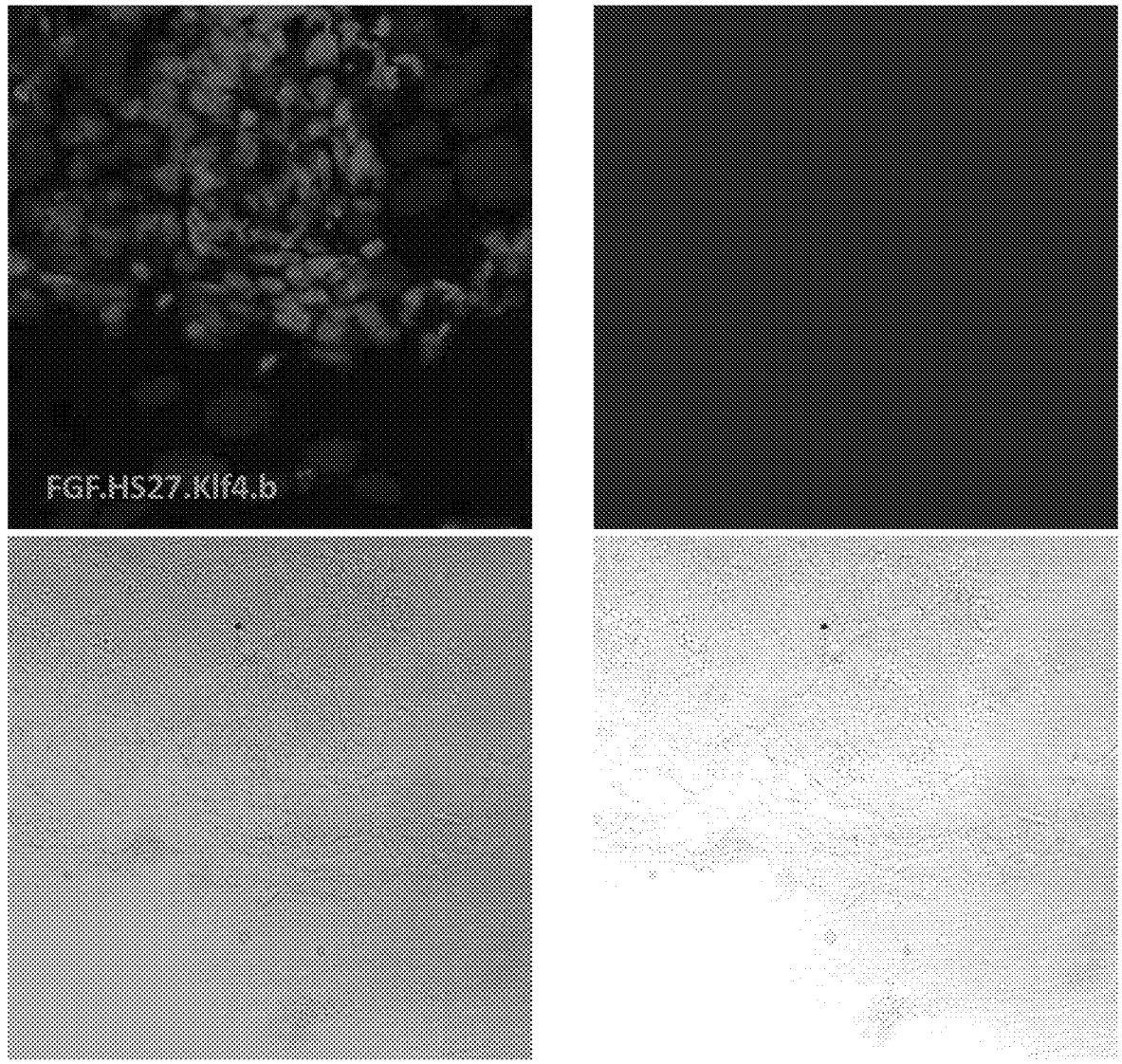

FIG. 30 is an image from a confocal microscope of H9 stem cells that have been grown in bFGF over human feeder cells and shows they are negative for Klf4 which is a marker for naïve stem cells.

Figure 31:
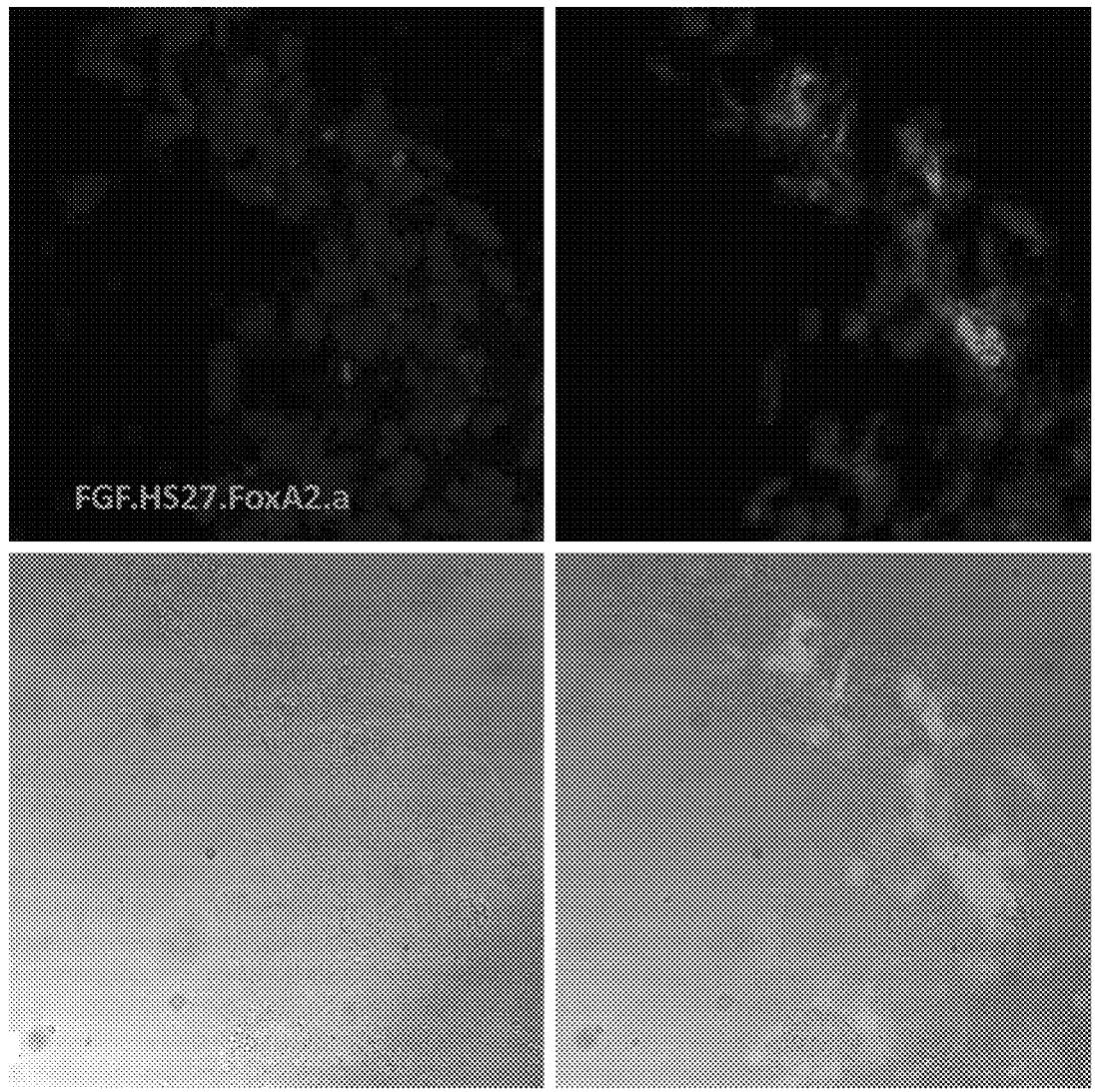

FIG. 31 is an image from a confocal microscope of H9 stem cells that have been grown in bFGF over human feeder cells and shows they are positive for Foxa2 a marker for primed stem cells.

Figure 32:
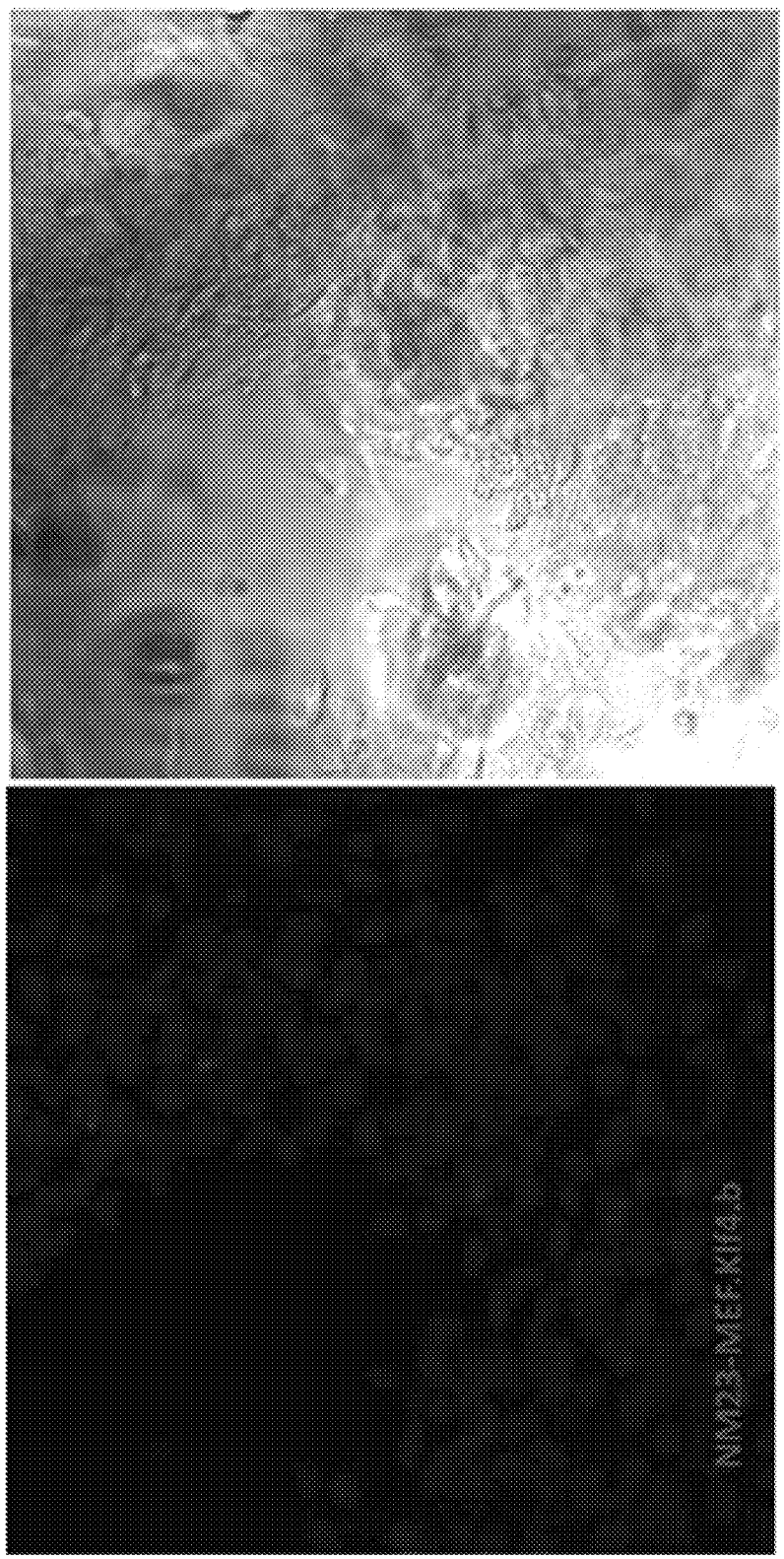

FIG. 32 is an image from a confocal microscope of H9 stem cells that have been grown in NM23-S120G over mouse feeder cells and shows they are negative for Klf4 which is a marker for naïve stem cells.

Figure 33:
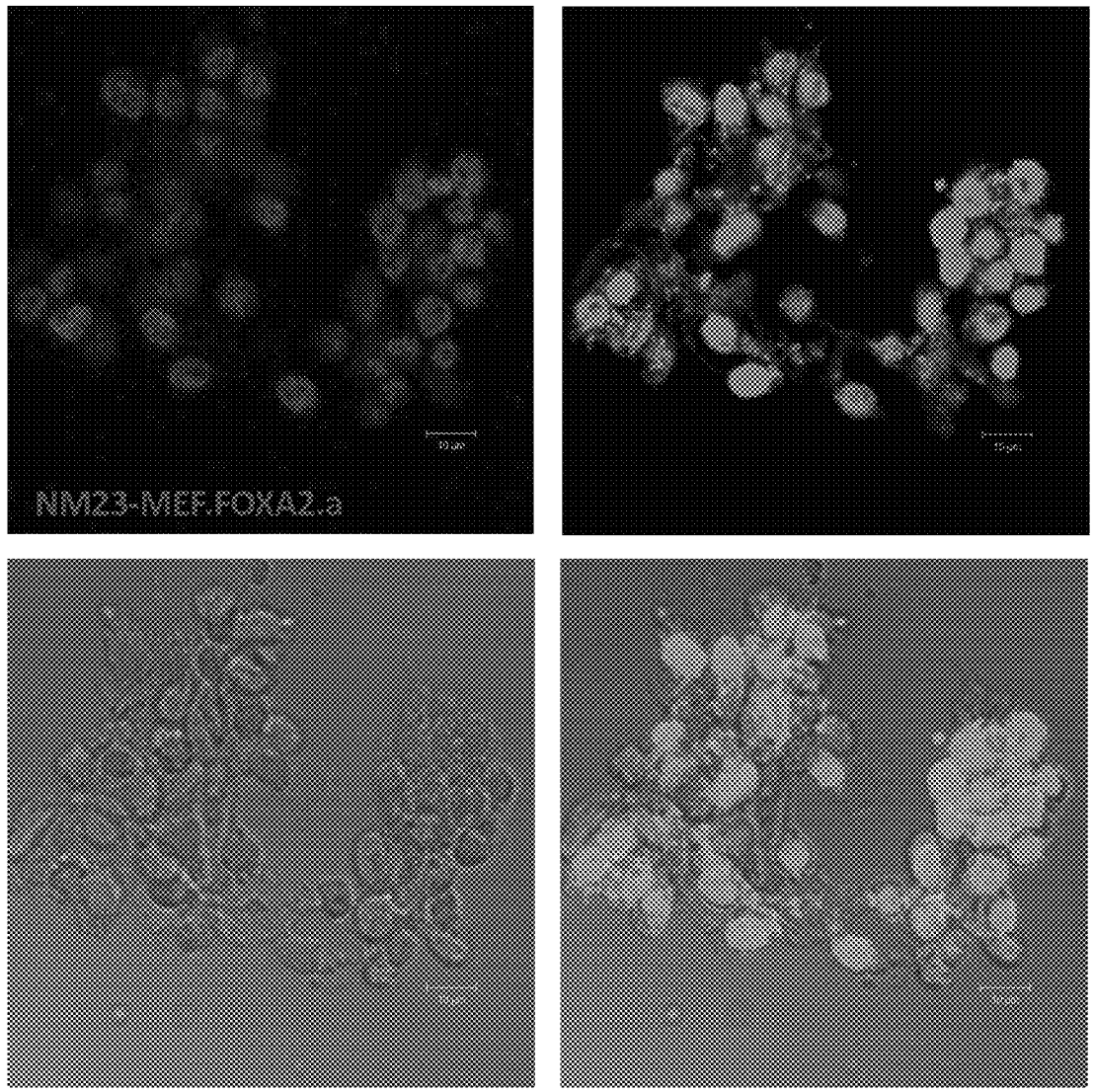

FIG. 33 is an image from a confocal microscope of H9 stem cells that have been grown in NM23-S120G over mouse feeder cells and shows they are positive for Foxa2 a marker for primed stem cells.

Figure 34:
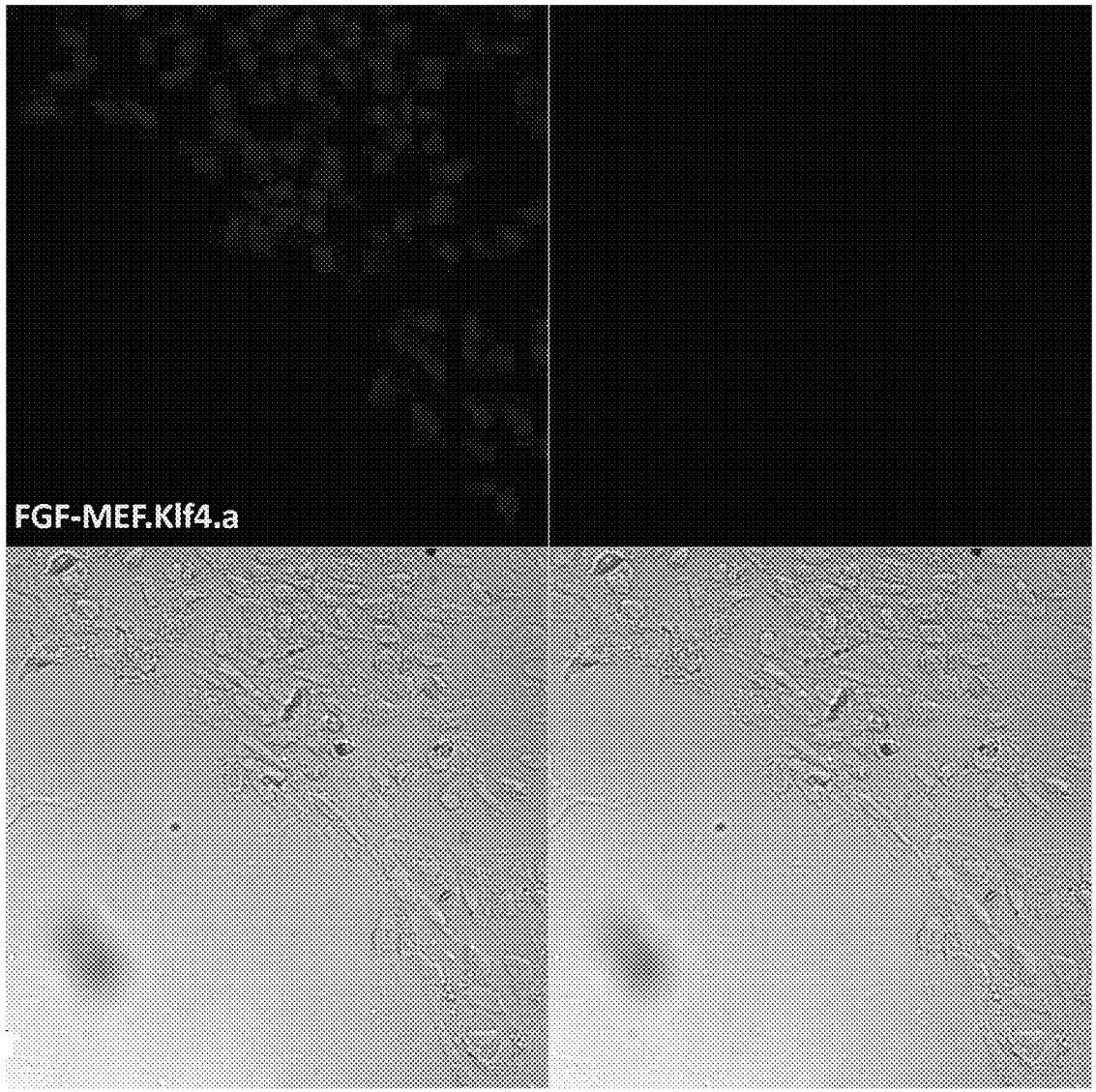

FIG. 34 is an image from a confocal microscope of H9 stem cells that have been grown in bFGF over mouse feeder cells and shows they are negative for Klf4 which is a marker for naïve stem cells.

Figure 35:
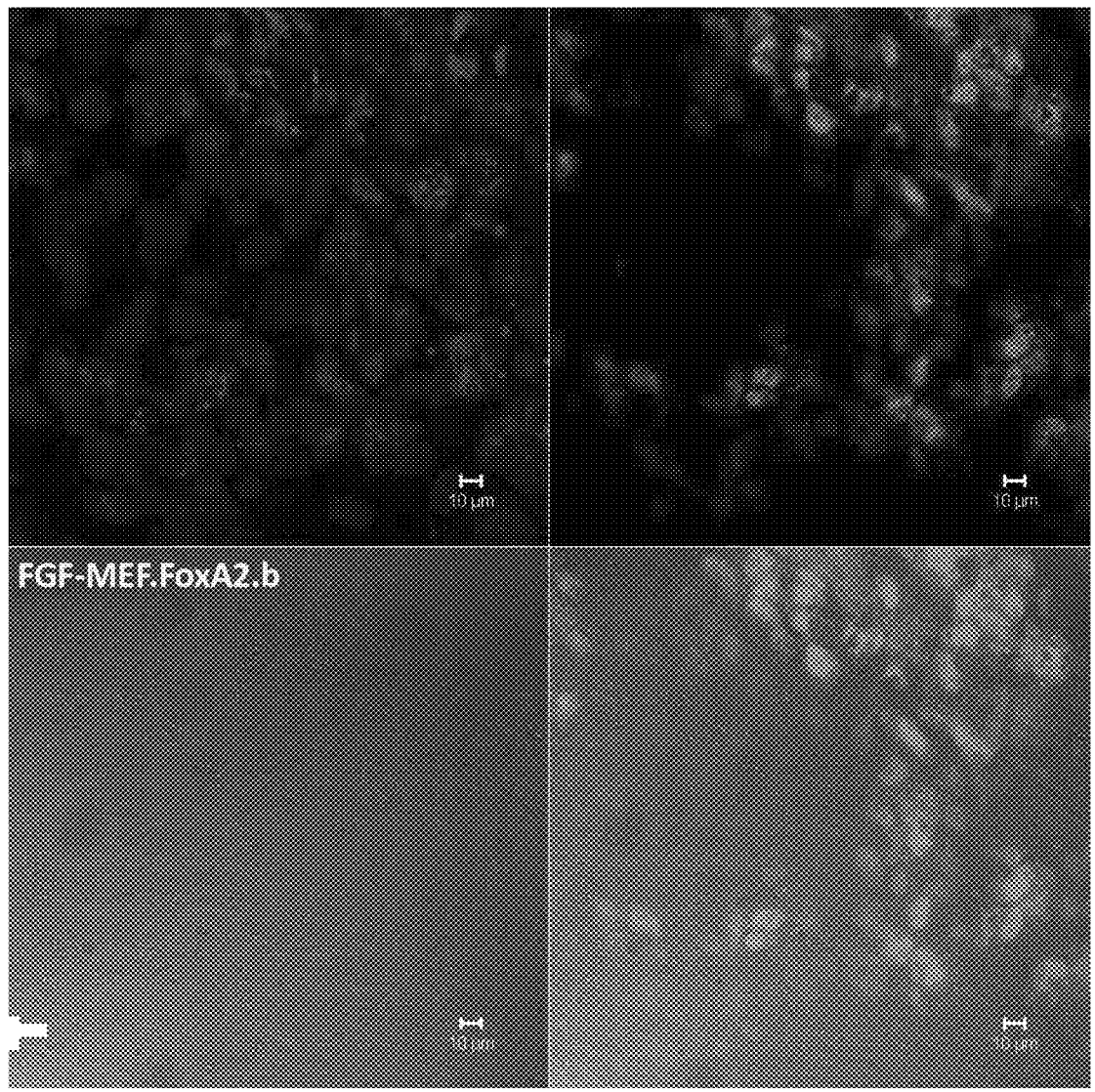

FIG. 35 is an image from a confocal microscope of H9 stem cells that have been grown in bFGF over mouse feeder cells and shows they are positive for Foxa2 a marker for primed stem cells.

Figure 36:
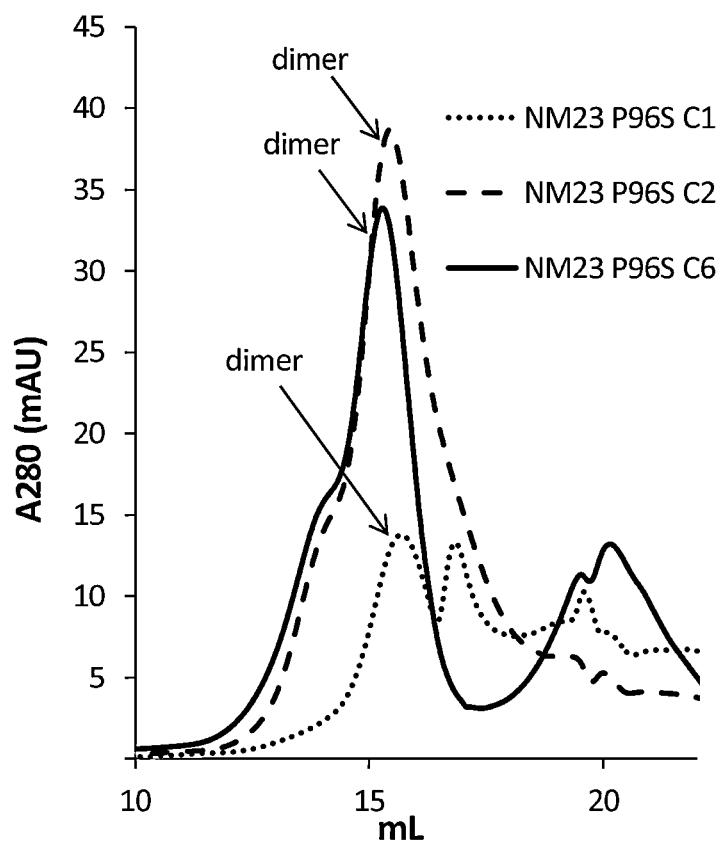

FIG. 36 is an overlay of FPLC traces of the soluble fractions of NM23-P96S mutants having 1, 2 or 6 deletions at the C-terminus, wherein the dimer peaks are indicated.

Figure 37:
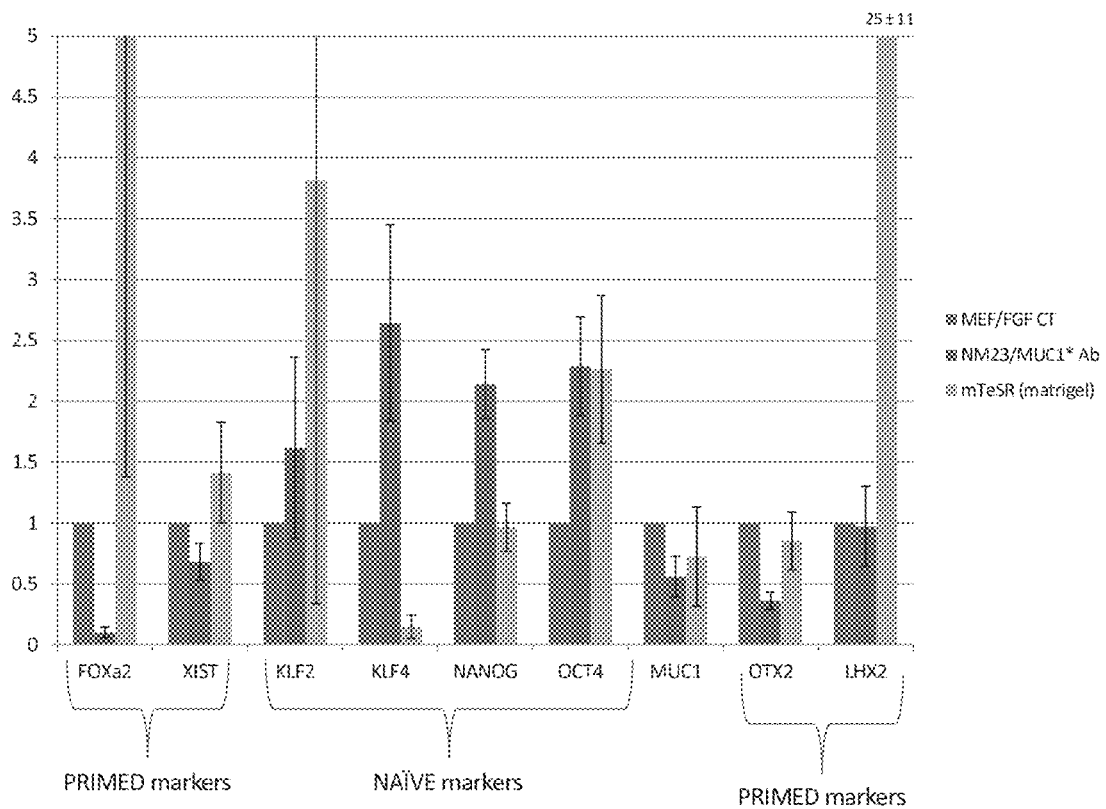

FIG. 37 shows graph of RT-PCR experiments to measure the expression levels of naïve and primed markers for human ES cells grown under a variety of conditions which are described in Example 10.

DETAILED DESCRIPTION OF THE PREFERRED EMBODIMENTS

In the present application, "a" and "an" are used to refer to both single and a plurality of objects.

The present invention relates to the field of mammalian cell culture, and particularly to the culture of immature cells such as stem cells, and provides methods and compositions for cell attachment to, cultivation on and detachment from a substrate containing from at least about 0.5% N, a sum of O and N greater than or equal to 17.2% and a contact angle of about 13.9 degrees and lacking a feeder layer. In one embodiment, the substrate also has attached thereto an antibody that binds to a cell surface receptor. In another embodiment, the cells are cultured in a media that contains a MUC1* activator. In yet another embodiment, the media also contains a Rho Kinase or a Rho inhibitor (ROCi). In yet another embodiment, the invention relates to methods for eliminating the need for a Rho kinase inhibitor. In still another embodiment, the invention relates to methods, growth factors and surfaces for the selection of, maintenance of or induction of naïve state stem cells.

Stem Cell Proliferative Surface

As used herein, a stem cell proliferation surface is any surface that may be chemically or biologically modified to enable the attachment of human stem cells, which further allows the stem cells to proliferate and from which the stem cells can be harvested. WO2009/105570 describes plasma modification of plasticware for cell culture such that the resultant surface is better for cell attachment and in particular enables the attachment of human stem cells, which are non-adherent cells. One of the surfaces described in WO2009/105570 is marketed as Vita™ surface (ThermoFisher, USA). In particular, surface #4 in WO '570 has been promoted for the growth of stem cells. Unfortunately, the methods required to prepare, also known as "acclimate", these cells to be able to bind to and then grow on those surfaces is very long and involved. WO '570 discloses that stem cells that are manually dissected and lifted off of another surface do not bind to their surfaces. In addition, the stem cells need to be enzymatically passaged to single cells several times, e. g., 38 times and 48 times before they will bind or grow on the disclosed surfaces. Instructions for use of the Vita™ surfaces further describe that stem cells must be cultured in the presence of a Rho kinase inhibitor, without which the stem cells will not bind to or stay bound to the surface. Another shortcoming of WO '570 is that although the disclosed surfaces are defined substrates intended to replace the use of Matrigel and feeders cells, stem cells do not grow on the surfaces unless conditioned media from mouse feeder cells is added to the standard bFGF stem cell culture media, thus defeating the purpose of a defined, animal-free surface.

In the present invention, we have shown that surfaces described in WO2009/105570, more particularly surfaces that are comprised of 1.7-2.1% Nitrogen, 26.4-28.7% Oxygen and 28.2-30.7% Nitrogen and Oxygen combined, wherein the surface has a contact angle of 14.3-18.8 degrees, can be used for the culture of stem cells in the absence of conditioned media if they are grown in the presence of a ligand that dimerizes the MUC1* receptor. Ligands that dimerize and activate the MUC1* receptor include bivalent antibodies raised against the PSMGFR peptide whose sequence corresponds to the first 45 amino acids of the MUC1 receptor that are proximal to the cell surface. Preferred are antibodies raised against peptides whose sequence corresponds to the PSMGFR peptide except lacking the 10 amino acids that are immediately adjacent to the cell surface. NM23 is a ligand of MUC1* and more particularly dimeric NM23 or mutants such as NM23-S120G, NM23-P96S which may or may not be combined with C-terminal deletions of 1-6 amino acids that prefer dimer formation over formation of teteramers and hexamers are especially preferred.

In addition to eliminating the need for conditioned media, the present invention discloses a method for minimizing the acclimation time required to adapt stem cells to growth on these and other defined surfaces. As is more fully detailed elsewhere in the present application, stem cells that have been grown in NM23 do not need a lengthy adaptation period. Further, stem cells previously cultured in FGF and conditioned media can be adapted to bind to the surfaces described in application WO2009/105570 by briefly incubating the cells in NM23 containing media before introduction to the defined surface. The contents of WO2009/105570 are incorporated by reference herein in its entirety, in particular regarding its disclosure of the material and composition of the stem cell growth surface.

In another improvement, the present invention is directed to coating the surfaces described in WO2009/105570 with ligands or antibodies that bind to the MUC1* receptor, which results in improved cell attachment, and inhibits spontaneous differentiation better than using the surfaces absent the MUC1* ligands. See FIG. 12e. The invention also contemplates the use of ligands to other stem cell surface proteins.

Naïve Cells

Recent research articles conclude that human stem cells cultured in FGF and fibroblast feeder cell conditioned media are no longer truly pluripotent (naïve or ground state) stem cells. Rather, growth in bFGF has brought the human stem cells to a more mature state called "primed." The results of work in the area of primed versus naïve human stem cells imply that primed stem cells are not able to differentiate into fully functional adult cells the way true pluripotent stem cells should. Researchers have developed methods to temporarily revert primed stem cells back to the true pluripotent state which they call "naïve". Because naïve stem cells grow via a different pathway than primed stem cells, it follows that they will bear cell surface receptors that are either different from or expressed to different levels than those expressed on the surface of primed stem cells. Therefore, primed stem cells and naïve stem cells will differ in their affinities for chemically or biochemically defined surfaces.

One of the characteristics of primed stem cells is that they cannot survive serial harvesting using enzymatic cleavage, but naïve stem cells can. Because WO2009/105570 discloses that only stem cells that are serially harvested by enzymatic cleavage will bind to their surfaces, we conclude that naïve stem cells bind to the WO '570 surfaces, in particular the surface marketed as Nunclon™ Vita™ surface (ThermoFisher, USA). Therefore, surfaces described in WO2009/105570, herein are referred to as Vita surfaces or Vita-like surfaces, can be used to select for naïve stem cells and more generally for the growth and/or maintenance of human stem cells that are in the naïve state or in a more naïve state than those cultured in the conventional bFGF media on feeder cell surfaces.

Figure 12A:
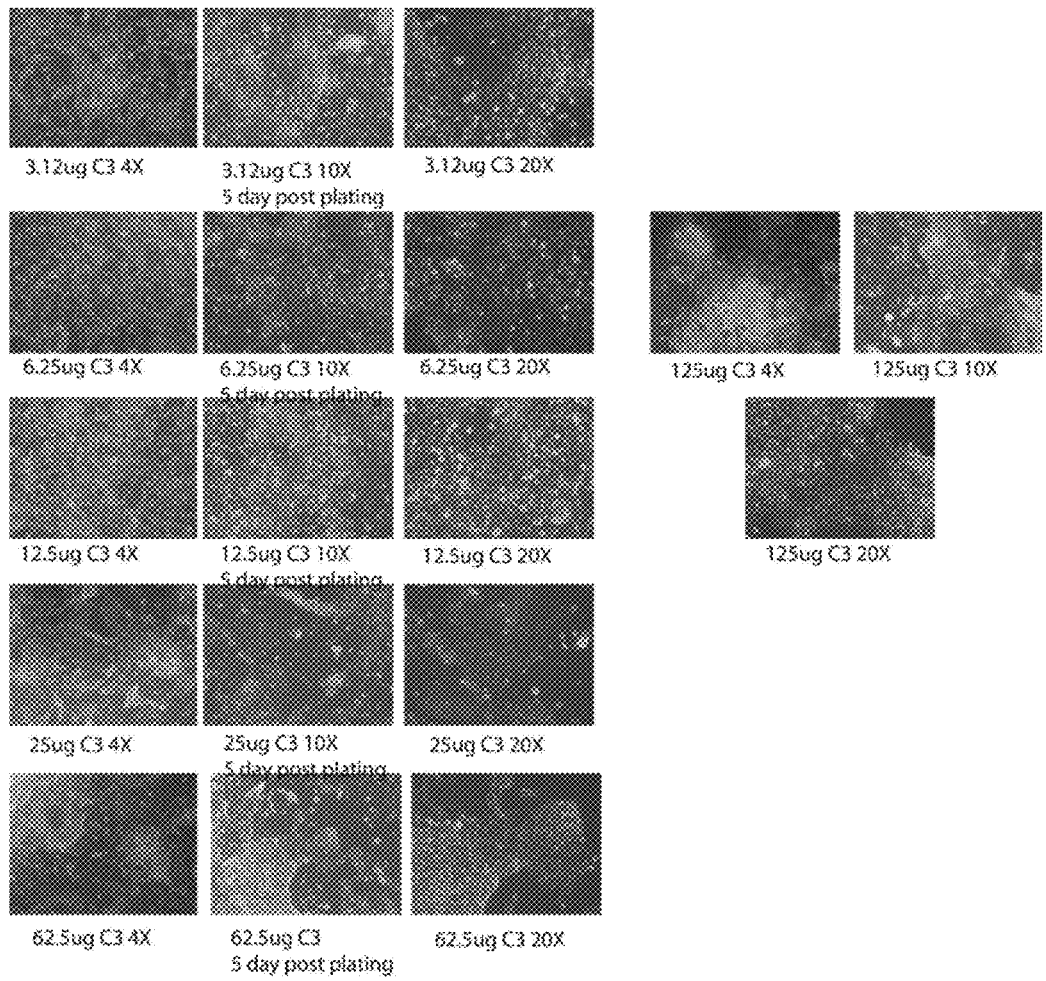
FIG. 12a-12d shows photos from 4× magnification to 20× of human ES cells that have been trypsinized to single cells then plated onto Vita-type surfaces that were coated with varying amounts of monoclonal antibody 2D6C3 as indicated and cultured in NM23-MM wherein a Rho kinase inhibitor was present during the first 48 hours to aid in attachment.
Figure 12B:
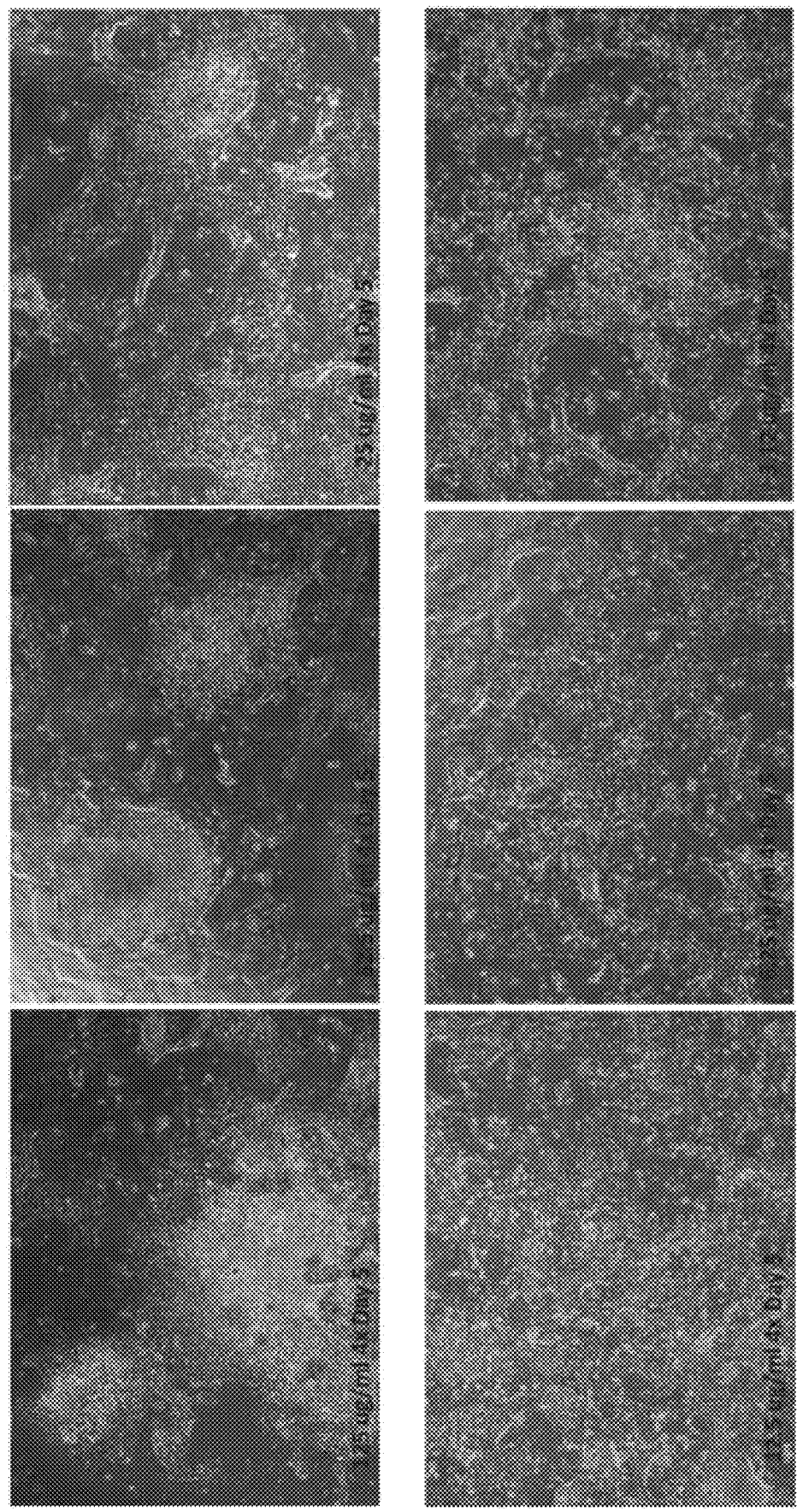

Another reported characteristic of naïve stem cells is that they have the ability to grow in sheets and not just in colony formation. We have observed that stem cells cultured with a MUC1* activator, including anti-MUC1* antibodies and NM23, also grow in sheets when grown on non-feeder cell surfaces and non-Matrigel surfaces. More particularly, human stem cells cultured with a bivalent MUC1* activator, including anti-MUC1* antibodies and dimeric NM23 or NM23 variants, and growing over a surface that has been coated with anti-MUC1* or NM23 dimers, grow in sheets rather than colonies which is characteristic of naïve human stem cells. In a preferred embodiment, anti-MUC1* antibodies are adsorbed onto a Vita or Vita-like surface and attached human stem cells are cultured in a minimal stem cell media containing NM23 or an NM23 variant wherein it is in the dimeric state. FIG. 12e showing results of Example 5 demonstrates that human stem cells grow in sheets rather than colonies when cultured in a media containing a MUC1* activator and on a Vita-like surface, optionally presenting anti-MUC1* antibodies. In an especially preferred embodiment, the MUC1* activator media does not contain bFGF or TGF-beta. FIG. 25 and the experiment of Example 10 show that human stem cells cultured in bFGF-containing media are in the primed state, whereas stem cells cultured in a MUC1* activating ligand, such as dimeric NM23, and optionally on a Vita or Vita-like surface also optionally presenting MUC1* ligands such as anti-MUC1* antibodies, are in the naïve state or in a more naïve state. In FIG. 12, RT-PCR is used to measure expression levels of naïve versus primed genes in human H9 ES (embryonic stem) cells. These cells cultured according to the standard method of 4 ng/ml bFGF added to minimal stem cell media and growing over a surface of mouse fibroblast feeder cells (MEFs), "MEF/FGF CT", have been defined as "1" and all other growth methods have been normalized to this value. In these figures "NM23/MUC1* Ab" refers to 8 nM of NM23-S120G in dimeric form in minimal stem cell media in the absence of any other growth factor, and cultured over a Vita plate coated with a MUC1* antibody (C3). FIG. 12 shows that compared to stem cells cultured by conventional methods, growth in NM23 dimers over a surface of a MUC1* antibody on a Vita plate resulted in lower expression of the primed markers and higher expression of the naïve markers.

mTeSR is a commercially available semi-defined media containing high concentrations of bFGF and TGF-beta. FIG. 12b shows the same type of stem cells cultured in mTeSR and over a layer of Matrigel, resulted in higher expression of the primed markers Foxa2 and XIST, but lower expression of the naïve markers Klf2, Klf4, and Nanog. Oct4, a pluripotency marker was on average expressed higher than the control. As can be seen from the passage number (p1-14), consecutive passaging in mTeSR over Matrigel did not improve the expression pattern of the "bad" markers.

Figure 12C:
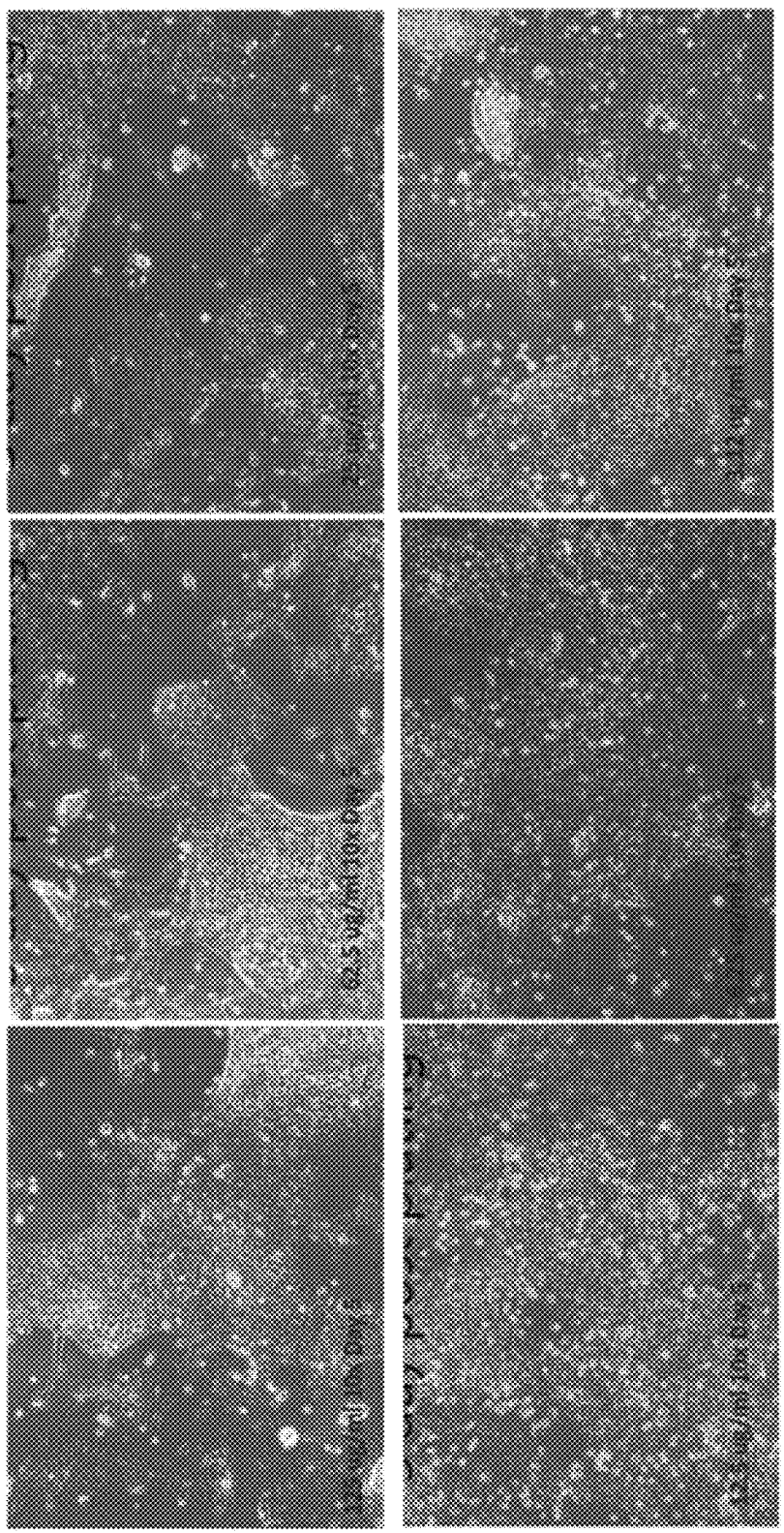

Conversely, FIG. 12c shows that culturing the stem cells in NM23 media over an anti-MUC1* antibody surface increased the expression of the naïve (good) markers and decreased the expression of the primed markers and that the pattern of naïve versus primed expression did improve with each successive passage number. Although the human integrin Vitronectin is defined and xeno-free when made as the recombinant protein, the results shown in FIG. 12d strongly argues that the interaction of Vitronectin with some antigen on the surface of stem cells signals a pathway that is not naïve. Stem cells of the same parent source were taken from growth on feeders in bFGF and for a single passage were cultured in either bFGF plus feeder cell conditioned media, mTeSR or NM23 in minimal media and all were grown over a layer of Vitronectin. The RT-PCR measurements show that although the NM23 media gave the gene expression profile that was more naïve than the others, in general, growth over Vitronectin caused an increase in expression of the primed markers and a decrease of the naïve markers.

FIG. 37 shows RT-PCR measurements of human stem cells cultured in bFGF over MEF feeders (n=3), mTeSR over Matrigel (n=5) or NM23-S120G dimers in minimal stem cell media over a Vita surface coated with 12.5 ug/ml of 2D6C3 the monoclonal anti-MUC1* antibody (n=6). In this experiment, two additional primed markers, OTX2 and LHX2, were also measured. The graph of FIG. 37 shows that consistent with other experiments, growth in NM23 over a surface presenting ligands for MUC1* increases expression of naïve markers and decreases expression of primed markers.

In a companion experiment, ICC staining was used to assess the expression of only two markers: FOXa2 (primed) and KLF4 (naïve) in response to growing human ES cells in either bFGF or NM23 (dimers in minimal stem cell media) over either mouse feeder cells or human feeder cells. FIGS. 27-35 show that only human stem cells cultured in an NM23 media over a surface of human fibroblasts expressed the naïve marker KLF4, but not the primed marker FOXa2. Conversely, the same source cells plated over a layer of mouse fibroblasts and cultured in media containing NM23 or bFGF did not express the naïve marker KLF4 but did express the primed marker FOXa2.

Taken together, these data indicate growing human stem cells over a layer of mouse cells or over a layer of Vitronectin maintains or induces the primed state and culturing human stem cells in bFGF-containing media also maintains or induces the primed state. We therefore conclude that human naïve stem cells grow by the MUC1* pathway and can be maintained or induced in media that activates this pathway. For example, in a media that contains an agent that dimerizes MUC1* and in solution or on a surface that does not activate a primed pathway and optionally activates a pluripotency pathway such as ligands that dimerize MUC1*. In a preferred embodiment, stem cells are maintained or induced to revert to a more naïve state by culturing them in a media that contains the dimeric form of NM23 and cells are attached to a Vita-like surface or a surface that is coated with an anti-MUC1* antibody. In a still more preferred embodiment, the stem cells are cultured in an NM23 dimer containing media wherein the concentration of NM23 is between 8-32 nM and the surface is a Vita surface coated with anti-MUC1* antibody 2D6C3 or 2D6C8 at a concentration of 3-125 ug/mL. In addition, antibodies that bind to MUC1*, optionally plated onto a Vita-like surface, can be used to identify and isolate naïve stem cells.

In addition, primed stem cells can be made to revert to a naïve or more naïve state by growing them under conditions in which the MUC1* pathway is activated. For example, by the introduction of nucleic acids that cause or increase expression of MUC1* or its ligands, including NM23 or NM23 variants, or agents that result in increased cleavage of MUC1 are introduced into cells, which may be adult, progenitors or primed stem cells, to make them revert to a more naïve or naïve state.

Applicant has discovered that stem cells grow better on a surface in a minimal stem cell media (MM or MN6) that contains a MUC1* activator such as bivalent anti-MUC1* or NM23, particularly dimeric NM23 or mutant that prefer dimerization such as NM23-S120G, NM23-P96S, C-terminal deletions of NM23 wherein one to six amino acid deletions may be made or NM23-S120G or NM23-P96S also with one to six amino acid deletions at the N-terminus, wherein NM23-P96S with six deletions from the C-terminus is preferred because it produces a majority of dimers in the soluble fraction. In addition, when a thin layer of anti-MUC1* antibody is applied to a surface such as plasticware, tissue culture treated plate, Vita-like surfaces or the Vita™ surface, stem cell proliferation was enhanced and spontaneous differentiation was inhibited. Further, stem cells cultured in FGF and mouse embryonic fibroblast (MEF) conditioned media (CM) showed poor attachment to the Vita surface if plated in FGF-CM. In contrast, the cells attached and grew if they were plated in and subsequently cultured in NM23-MM media rather than FGF-CM. Attachment and subsequent growth was improved when FGF-CM (conditioned media)-grown cells were harvested then briefly incubated in NM23-MM, before plating.

The performance of defined surfaces such as those described in WO2009/105570, more particularly surfaces that are comprised of 1.7-2.1% Nitrogen, 26.4-28.7% Oxygen and 28.2-30.7% Nitrogen and Oxygen combined, wherein the surface has a contact angle of 14.3-18.8 degrees, was greatly improved by adding a layer of an agent that dimerizes MUC1* receptor, including anti-MUC1* antibodies and NM23, especially mutant NM23-S120G that prefers dimer formation. The present invention is directed to attaching an agent that dimerizes MUC1* to onto the surfaces described in WO '570. In a preferred embodiment, the agent is a bivalent anti-MUC1* antibody. Especially preferred are monoclonal antibodies 2D6C3 and 2D6C8. The invention also includes coating or attaching the antibodies to a layer of protein or polymer that is in contact with a surface described in WO '570.

The present invention is also directed to generation of polymers on a surface that result in their chemical composition being the percentages of N, O and N plus O essentially the same as the planar solid substrates described in WO2009/105570, more particularly surfaces that are comprised of 1.7-2.1% Nitrogen, 26.4-28.7% Oxygen and 28.2-30.7% Nitrogen and Oxygen combined, wherein the surface has a contact angle of 14.3-18.8 degrees. Agents that dimerize MUC1* may optionally be attached to these substrates to improve growth and inhibition of differentiation of human stem cells as well as for the isolation and enhancement of populations of naïve stem cells.

A kit of the invention may consist of a vessel for cell culture in which the chemical composition of the surface is approximately comprised of 1.7-2.1% Nitrogen, 26.4-28.7% Oxygen and 28.2-30.7% Nitrogen and Oxygen combined, wherein the surface has a contact angle of 14.3-18.8 degrees and instructions to culture cells in a media containing an agent that dimerizes MUC1*, such as bi-valent anti-MUC1* or NM23 or dimer form of NM23, NM23-S120G, NM23-P96S, or those mutations and those that have one to six C-terminal amino acid deletions.

We have discovered that human naïve stem cells grow via the MUC1* pathway and not by the FGF (fibroblast growth factor receptor) pathway.

Further we discovered that primed stem cells, ES and iPS (induced pluripotent stem), can be stably converted to the naïve state by activating the MUC1* growth factor receptor pathway.

We further discovered that human stem cells progress to the primed state or cannot be reverted to the naïve state even with activation of the MUC1* pathway if they are cultured in the presence of secretions from mouse cells, such as mouse embryonic fibroblast (MEF) feeder cells. On the contrary, human stem cells cultured in minimal media plus NM23 (optionally NM23-S120G mutant) over human feeder cells such as HS27 foreskin fibroblast feeder cells, do grow as more naïve stem cells and can be maintained in that state indefinitely and through serial passaging.

In addition to activating the MUC1* growth factor receptor, it is necessary not to activate certain pathways that make mouse stem cells grow. FGF should not be added to media for culturing human stem cells in the naïve state. Similarly, human stem cells will progress to the primed state if cultured over mouse feeder cells.

In contrast, human naïve stem cells will be stably maintained and propagated in the naïve state or at least a more naïve state if they are cultured with a MUC1* activator such as NM23-S120G and grown over human (and not mouse) feeder cells, such as HS27 foreskin fibroblast cells, or over a xeno-free surface. Xeno-free surfaces that do not secrete factors that would influence the cells to mature to the primed state include standard plasticware, cell culture treated plates, substrates with a high binding capacity such as Vita or Synthemax, all of which can optionally be derivatized with an antibody to a stem cell surface antigen such as anti-MUC1*, anti-Tra 1-81/1-60 or anti-SSEA3/4.

The MUC1* growth factor receptor pathway is activated by NM23 and in particular NM23 dimers. We typically activated naïve stem cell growth by culturing cells in a minimal stem cell media plus NM23-S120G mutant which is a mutant that prefers dimerization and does not form the higher order multimers that do not activate the MUC1* receptor. Other MUC1* activators include bivalent antibodies that bind to portions of MUC1* that dimerize it. For example, an antibody raised against the 45 amino acids of the MUC1* extra cellular domain dimerize and activate the MUC1* growth factor receptor and support stem cell growth.

The discoveries disclosed herein have far-reaching implications. First, most human stem cells today are grown in FGF over mouse feeder layers or over Matrigel and fed with FGF plus conditioned media from the mouse feeder cells. The findings presented herein show that both FGF and mouse feeder cells corrupt human stem cells and induce their progression into the primed state which may be a non-productive state from which they are not able to mature into functional adult cells. Therefore, in order to obtain adult functional cells from human stem cells, the starting cells must be in the naïve state. A major problem in the stem cell field is that many cells cannot be made to mature into functional adult cells and when they are coerced into doing so, it is a rare event. These studies are evidence that a major problem is that human stem cells that are in use today have been corrupted by exposure to pathways that are not human. Therefore, to obtain stem cells that are able to mature into functional adult cells, they must be cultured in a MUC1* activator, e. g. NM23 in dimeric form and if feeder cells are used at any time, they must be human.

Implications of previous characterization of human stem cells that were all "Primed"

The discoveries disclosed herein show that many of the current "discoveries" based on work with corrupted stem cells are also corrupted. Data obtained from studies of stem cells grown by FGF pathway and/or on mouse feeder cells or their conditioned media is a mixture of pertinent and irrelevant data with no way of determining which findings apply to humans and which do not. For example, an emerging approach to the treatment of cancer is to suppress the cancer cell's ability to self-renew by inducing differentiation. Studies were done in which microRNAs of cancer cells were compared to the microRNAs of stem cells, especially newly differentiating stem cells, to determine which regulatory factors were missing in the cancer cells. The theory was that the missing microRNAs that induce differentiation could be introduced to the cancer cells to "reprogram" them so that they would behave more like healthy cells. The problem with this previous body of work is that the micro RNAs that were analyzed were from stem cells grown with FGF and over mouse feeder cells. Mounting evidence supports the theory that bFGF is the growth factor that makes mouse stem cells grow, but not human pluripotent stem cells. We now know that both bFGF and mouse feeder cells secrete factors that make human stem cells leave their natural naïve state and become "primed" or "mouse-human chimeras." The primed state is characterized by gene expression patterns, and consequently microRNA expression patterns, that are very different from those expressed in naïve stem cells. Therefore, many if not the vast majority of the microRNAs that were identified as signaling the onset of differentiation, and therefore useful in potential cancer treatments, may only signal the onset of mouse stem cell differentiation or may not be related at all to the natural state in which human naïve stem cells propagate via the MUC1* pathway and can only differentiate normally from the naïve state. Therefore, microRNAs previously identified as being those that signal human stem cell's exit from pluripotency may only be microRNAs that signal departure from an unnatural state of pseudo pluripotency and therefore would be of no use for the treatment of human cancers. Therefore, to accurately identify microRNA profiles that induce differentiation, which could be used to treat cancers, one would need to use naïve stem cells, which is the natural pluripotent state for human stem cells, cultured in growth factors that stimulate the human and not the mouse stem cell pathway. An accurate way to identify microRNAs that regulate differentiation of human stem cells or progenitors is to perform the differential analyses on human naïve stem cells that are allowed to differentiate from the naïve state. MicroRNAs that are upregulated when the naïve stem cells initiate differentiation are then identified and can be used for the treatment of cancers. In a preferred embodiment, the naïve cells are obtained by culturing human stem cells in NM23, dimeric form, on surfaces coated with anti-MUC1* antibodies. In a more preferred embodiment the surfaces coated with anti-MUC1* antibodies are Vita-like surfaces. In other embodiments, naïve-like stem cells may be cultured in NM23 dimers over a layer of inactivated human feeder cells or over a layer of human cancer cells or in the presence of their secretions. microRNAs present in newly differentiating naïve stem cells but missing from the cancer cells are identified and used as anti-cancer therapeutic agents.

In a previous patent application WO 2011/159960, the inventors put forward evidence that cancer cells are cells that have become trapped in a stem cell proliferation plateau. We noted that some kinds of cancer cells can be co-cultured while others cannot. We stated that the cancer cells that can be co-cultured are trapped in the same stem cell proliferation plateau and their growth is being regulated by the same signature of microRNAs. Cancer cells that can be co-cultured belong to the same type of cancer which is independent of organ of origin. The identity of the individual microRNAs in each signature that regulates each cancer type can be determined using techniques such as Deep Sequencing and total transcriptome analysis. Once the microRNA signatures of the different sub-types of cancer have been identified, cancers can be treated or prevented by mixing together one or more microRNA signatures of a different cancer type than the one that has affected the patient. In an alternative approach, the microRNA signature that maintains human naïve stem cells in various proliferation plateaus could be determined, then these different microRNA signatures could be mixed to create a cancer vaccine.

MUC1

MUC1 comprises several regions termed herein as follows, recited in an order starting from the C-terminus and extending through the cell membrane and out into the extracellular domain. The basic structure of the MUC1 receptor comprises: 1) cytoplasmic tail; 2) transmembrane section; 3) MGFR; 4) IBR, 5) Unique Region, 6) repeats, and N-terminus region comprising a signal peptide. For a detailed description of MUC1 and its function in normal and tumor cells, see PCT/US2005/032821, which is incorporated by reference herein, in its entirety for its description of the function and activity of cleaved MUC1 on the cell surface.

The term "MUC1 Growth Factor Receptor" (MGFR) is a functional definition meaning that portion of the MUC1 receptor that interacts with an activating ligand, such as a growth factor or a modifying enzyme such as a cleavage enzyme, to promote cell proliferation. The MGFR region of MUC1 is that extracellular portion that is closest to the cell surface and is defined by most or all of the PSMGFR, as defined below. The exact cleavage site of MUC1 is not known and further, enzymes that cleave the protein can cleave at one or more locations. It also appears that the MUC1* growth factor receptor form, which is a cleavage product, may be cleaved at varying locations based on the cell type. The MGFR is inclusive of both unmodified peptides and peptides that have undergone enzyme modifications, such as, for example, phosphorylation, glycosylation, etc. Results of the invention are consistent with a mechanism in which this portion is made accessible to the ligand upon MUC1 cleavage at a site associated with tumorigenesis that causes release of the some or all of the IBR from the cell. MGFR is also known as MUC1*.

As used herein, "anti-PSMGFR" refers to any antibody that recognizes a region of the MGFR and optionally any portion of PSMGFR. Antibody to nat-PSMGFR is exemplified and preferred in the application, but is not meant to be limited to an antibody made against this specific sequence, as other fragments of MGFR and PSMGFR are also contemplated.

An anti-MUC1* antibody refers to any antibody that recognizes a MUC1 protein, present on stem cells, progenitor cells or cancer cells, wherein the MUC1 protein is devoid of the tandem repeat domain. The term "Primary Sequence of the MUC1 Growth Factor Receptor" (PSMGFR) is a peptide sequence that defines most or all of the MGFR in some cases, and functional variants and fragments of the peptide sequence, as defined below. The PSMGFR is defined as SEQ ID NO:10 listed below in Table 1, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus. A "functional variant or fragment" in the above context refers to such variant or fragment having the ability to specifically bind to, or otherwise specifically interact with, ligands that specifically bind to, or otherwise specifically interact with, the peptide of SEQ ID NO: 10. One example of a PSMGFR that is a functional variant of the PSMGFR peptide of SEQ NO: 10 (referred to as nat-PSMGFR—for "native") is SEQ NO: 12 (referred to as var-PSMGFR), which differs from nat-PSMGFR by including an —SPY— sequence instead of the native —SRY— (see bold text in sequence listings). Var-PSMGFR may have enhanced conformational stability, when compared to the native form, which may be important for certain applications such as for antibody production. The PSMGFR is inclusive of both unmodified peptides and peptides that have undergone enzyme modifications, such as, for example, phosphorylation, glycosylation, etc.

TABLE 1

Peptide sequences (listed from N-terminus to C-terminus):
Full-length MUC1 Receptor (Mucin 1 precursor, Genbank
Accession number: P15941)

```
MTPGTQSPFF LLLLLTVLTV VTGSGHASST PGGEKETSAT QRSSVPSSTE
KNAVSMTSSV LSSHSPGSGS STTQGQDVTL APATEPASGS AATWGQDVTS
VPVTRPALGS TTPPAHDVTS APDNKPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
```

TABLE 1-continued

Peptide sequences (listed from N-terminus to C-terminus):
Full-length MUC1 Receptor (Mucin 1 precursor, Genbank
Accession number: P15941)

```
APDTRPAPGS TAPPAHGVTS APDTRPAPGS TAPPAHGVTS APDNRPALGS
TAPPVHNVTS ASGSASGSAS TLVHNGTSAR ATTTPASKST PFSIPSHHSD
TPTTLASHST KTDASSTHHS SVPPLTSSNH STSPQLSTGV SFFFLSFHIS
NLQFNSSLED PSTDYYQELQ RDISEMFLQI YKQGGFLGLS NIKFRPGSVV
VQLTLAFREG TINVHDVETQ FNQYKTEAAS RYNLTISDVS VSDVPFPFSA
QSGAGVPGWG IALLVLVCVL VALAIVYLIA LAVCQCRRKN YGQLDIFPAR
DTYHPMSEYP TYHTHGRYVP PSSTDRSPYE KVSAGNGGSS LSYTNPAVAA ASANL
(SEQ ID NO: 1)
```

N-terminal MUC-1 signaling sequence for directing MUC1 receptor and truncated isoforms to cell membrane surface. Up to 3 amino acid residues may be absent at C-terminal end as indicated by variants in SEQ ID NOS:2, 3 and 4.

```
                                    (SEQ ID NO: 2)
            MTPGTQSPFFLLLLLTVLT.

(SEQ ID NO: 3)
            MTPGTQSPFFLLLLLTVLT VVTA (SEQ ID NO: 4)
            MTPGTQSPFFLLLLLTVLT VVTG
```

A truncated MUC1 receptor isoform having nat-PSMGFR at its N-terminus and including the transmembrane and cytoplasmic sequences of a full-length MUC1 receptor ("nat-PSMGFRTC isoform"—An example of "PSMG-FRTC"—shown excluding optional N-terminus signal sequence, which may be cleaved after translation and prior to expression of the receptor on the cell surface):

```
                                    (SEQ ID NO: 5)
G TINVHDVETQ FNQYKTEAAS RYNLTISDVS VSDVPFPFSA

QSGAGVPGWG IALLVLVCVL VALAIVYLIA LAVCQCRRKN

YGQLDIFPAR DTYHPMSEYP TYHTHGRYVP PSSTDRSPYE

KVSAGNGGSS LSYTNPAVAA ASANL
```

A truncated MUC1 receptor isoform having nat-PSMGFR and PSIBR at its N-terminus and including the transmembrane and cytoplasmic sequences of a full-length MUC1 receptor ("CM isoform"—shown excluding optional N-terminus signal sequence, which may be cleaved after translation and prior to expression of the receptor on the cell surface):

```
                                    (SEQ ID NO: 6)
    GFLGLS NIKIRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE

KVSAGNGGSS LSYTNPAVAA ASANL
```

A truncated MUC1 receptor isoform having nat-PSMGFR+PSIBR+Unique Region at its N-terminus and including the transmembrane and cytoplasmic sequences of a full-length MUC1 receptor ("UR isoform"—shown excluding optional N-terminus signal sequences):

```
                                    (SEQ ID NO: 7)
ATTTPASKST PFSIPSHHSD TPTTLASHST KTDASSTHHS

TVPPLTSSNH STSPQLSTGV SFFFLSFHIS NLQFNSSLED

PSTDYYQELQ RDISEMFLQI YKQGGFLGLS NIKFRPGSVV

VQLTLAFREG TINVHDVETQ FNQYKTEAAS RYNLTISDVS

VSDVPFPFSA QSGAGVPGWG IALLVLVCVL VALAIVYLIA

LAVCQCRRKN YGQLDIFPAR DTYHPMSEYP TYHTHGRYVP

PSSTDRSPYE KVSAGNGGSS LSYTNPAVAA ASANL
```

A truncated MUC1 receptor isoform including the transmembrane and cytoplasmic sequences of a full-length MUC1 receptor ("Y isoform"—shown excluding optional N-terminus signal sequence, which may be cleaved after translation and prior to expression of the receptor on the cell surface):

```
                                    (SEQ ID NO: 8)
GSGHASSTPG GEKETSATQR SSVPSSTEKN

AFNSSLEDPS TDYYQELQRD ISEMFLQIYK QGGFLGLSNI

KFRPGSVVVQ LTLAFREGTI NVHDMETQFN QYKTEAASRY

NLTISDVSVS DVPFPFSAQS GAGVPGWGIA LLVLVCVLVA

LAIVYLIALA VCQCRRKNYG QLDIFPARDT YHPMSEYPTY

HTHGRYVPPS STDRSPYEKV SAGNGGSSLS YTNPAVAATS ANL
```

A truncated MUC1 receptor isoform having nat-PSMGFR+PSIBR+Unique Region+Repeats at its N-terminus and including the transmembrane and cytoplasmic sequences of a full-length MUC1 receptor ("Rep isoform"—shown excluding optional N-terminus signal sequence, which may be cleaved after translation and prior to expression of the receptor on the cell surface):

(SEQ ID NO: 9)
```
LDPRVRTSAP DTRPAPGSTA PQAHGVTSAP DTRPAPGSTA
PPAHGVTSAP DTRPAPGSTA PPAHGVTSAP DTRPAPGSTA PPAHGVTSAP
DTRPAPGSTA PPAHGVTSAP DTRPAPGSTA PPAHGVTSAP DTRPAPGSTA
PPAHGVTSAP DTRPAPGSTA PPAHGVTSAP DTRPAPGSTA PPAHGVTSAP
DTRPAPGSTA PPAHGVTSAP DTRPAPGSTA PPAHGVTSAP DTRPAPGSTA
PPAHGVTSAP DTRPAPGSTA PPAHGVTSAP DTRPAPGSTA PPAHGVTSAP
DTRPAPGSTA PPAHGVTSAP DTRPAPGSTA PPAHGVTSAP DTRPAPGSTA
PPAHGVTSAP DTRPAPGSTA PPAHGVTSAP DTRPAPGSTA PPAHGVTSAP
DTRPAPGSTA PPAHGVTSAP DTRPAPGSTA PPAHGVTSAP DTRPAPGSTA
PPAHGVTSAP DTRPAPGSTA PPAHGVTSAP DTRPAPGSTA PPAHGVTSAP
DTRPAPGSTA PPAHGVTSAP DTRPAPGSTA PPAHGVTSAP DTRPAPGSTA
PPAHGVTSAP DNRPALGSTA PPVHNVTSAS GSASGSASTL VHNGTSARAT
TTPASKSTPF SIPSHHSDTP TTLASHSTKT DASSTHHSSV PPLTSSNHST
SPQLSTGVSF FFLSFHISNL QFNSSLEDPS TDYYQELQRD ISEMFLQIYK
QGGFLGLSNI KIRPGSVVVQ LTLAFREGTI NVHDVETQFN QYKTEAASRY
NLTISDVSVS DVPFPFSAQS GAGVPGWGIA LLVLVCVLVA LAIVYLIALA
VCQCRRKNYG QLDIFPARDT YHPMSEYPTY HTHGRYVPPS STDRSPYEKV
SAGNGGSSLS YTNPAVAAAS ANL
```

Native Primary Sequence of the MUC1 Growth Factor Receptor (nat-PSMGFR—an example of "PSMGFR"):

(SEQ ID NO: 10)
GTINVHDVETQFNQYKTEAASRYNLTISDVSVSDVPFPFSAQSGA

Native Primary Sequence of the MUC1 Growth Factor Receptor (nat-PSMGFR—An example of "PSMGFR"), having a single amino acid deletion at the N-terminus of SEQ ID NO: 10):

(SEQ ID NO: 11)
TINVHDVETQFNQYKTEAASRYNLTISDVSVSDVPFPFSAQSGA

"SPY" functional variant of the native Primary Sequence of the MUC1 Growth Factor Receptor having enhanced stability (var-PSMGFR—An example of "PSMGFR"):

(SEQ ID NO: 12)
GTINVHDVETQFNQYKTEAASPYNLTISDVSVSDVPFPFSAQSGA

"SPY" functional variant of the native Primary Sequence of the MUC1 Growth Factor Receptor having enhanced stability (var-PSMGFR—An example of "PSMGFR"), having a single amino acid deletion at the C-terminus of SEQ ID NO: 12):

(SEQ ID NO: 13)
TINVHDVETQFNQYKTEAASPYNLTISDVSVSDVPFPFSAQSGA

Truncated PSMGFR receptor (TR) (having "SPY" sequence of var-PSMGFR):

(SEQ ID NO: 14)
GTINVHDVETQFNQYKTEAASPYNLTISDVSVS

Extended Sequence of MUC1 Growth Factor Receptor (ESMGFR) (having "SPY" sequence of var-PSMGFR):

(SEQ ID NO: 15)
VQLTLAFREGTINVHDVETQFNQYKTEAASPYNLTISDVSVSDVPFPF

Tumor-Specific Extended Sequence of MUC1 Growth Factor Receptor (TSESMGFR) (having "SPY" sequence of var-PSMGFR):

(SEQ ID NO: 16)
SVVVQLTLAFREGTINVHDVETQFNQYKTEAASPYNLTISDVSVS
DVPFPFSAQSGA

Primary Sequence of the Interchain Binding Region) (PSIBR):
GFLGLSNIKFRPGSVVVQL (SEQ ID NO:17)
Truncated Interchain Binding Region) (TPSIBR):

(SEQ ID NO: 18)
SVVVQLTLAFREG

Repeat Motif 2 (RM2):

(SEQ ID NO: 19)
PDTRPAPGSTAPPAHGVTSAPDTRPAPGSTAPPAHGVTSA

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1.1—Stem Cell Minimal Media "MM"

Minimal Medium ("MM") 500 mL includes the following: 400 ml DME/F12/GlutaMAX I (Invitrogen #10565-018), 100 ml Knockout Serum Replacement (Invitrogen #10828-028), 5 ml 100×MEM Non-essential Amino Acid Solution (Invitrogen #11140-050), 0.9 ml (0.1 mM) beta-mercaptoethanol (55 mM stock, Invitrogen #21985-023), and optionally may contain 2.5 ml PSA (penicillin, streptomycin, amphotericin) MP *Biochem* (#1674049) for minimizing contamination risk.

Example 1.2—Stem Cell Defined Media—"MN6"

The 6-component minimal media, "MN6" consists of DMEM/F12/GlutaMAX or similar base media suitable for cell culture, supplemented with 1% non-essential amino acids, 64 mg/L ascorbic acid (Sigma), 14 ug/L sodium selenium (Sigma), 19.4 mg/L insulin (Sigma), 543 mg/L sodium bicarbonate (Sigma) and 10.7 mg/L transferrin (Sigma).

Example 1.3—Polyclonal Anti-MUC1* Antibodies that Facilitate Stem Cell Attachment to Surfaces Coated with the Antibody Rabbit polyclonal antibodies were generated by immunizing animals with the Primary Sequence of the MUC1 Growth Factor Receptor (PSMGFR) peptide. Sera was collected according to standard methods and then purified over an affinity column to which was bound either the PSMGFR peptide or a PSMGFR peptide missing the last ten (10) C-terminal amino acids, "C-10 peptide". The purified antibodies (SDIX-anti-FLR and SDIX-anti-C-10, respectively) were then coated directly onto plastic cell culture plates (Vita plates, ThermoFisher; or BD Falcon #353046) and shown to facilitate stem cell attachment. To coat surfaces with the antibody, concentrations between 1 ug/mL and 300 ug/mL in a volume of PBS that allowed for complete surface coverage was incubated at 4 degrees C. overnight or at room temperature for approximately 3 hours. Human stem cells bound to these anti-PSMGFR surfaces and the amount of attachment corresponded to the concentration of antibody coated onto the surface; a control antibody did not cause any stem cell attachment, see FIGS. 24a-c. Human stem cells H9s (WiCell) and BGO1V/hOG cells (Life Technologies) attached and proliferated as undifferentiated stem cells when cultured in minimal stem cell media, "MM", alone, in the presence of low nanomolar concentrations of NM23-H1 in the dimeric form, or in MM plus 4 ng/mL of bFGF supplemented with 50% conditioned media from either human or mouse fibroblast feeder cells. We concluded that the bivalent anti-PSMGFR antibody attached to the plate surface caused dimerization of the MUC1* receptor and thus acted as the growth factor. However, cells proliferated faster when NM23 (dimers) were added into the media.

Example 2—Development of Monoclonal Antibodies, 2D6C8 and 2D6C3 (Also Referred to Here as C3 and C8) that Facilitate Human Stem Cell Attachment to Surfaces MUC1* monoclonal antibodies were identified that preferentially bound to the portion of the MUC1* extra cellular domain that is more distal from the cell surface and these monoclonals were shown to better facilitate the attachment of human ES and iPS cells to surfaces. Mice were immunized with a peptide that is defined by the PSMGFR sequence. Supernatants of hybridoma clones were tested by ELISA for their ability to bind to the PSMGFR peptide and by FACS to determine which bound to live, MUC1* positive cells. Hybridomas were further selected if they preferentially bound to the PSMGFR peptide lacking 10 C-terminal amino acids, but did not bind if the peptide lacked the 10 N-terminal peptides. In addition, hybridomas were screened for their ability to facilitate stem cell attachment to a surface such as a plastic cell culture plate. Of these clones two, 2D6C8 and 2D6C3 were selected that when coated onto a surface captured stem cells and facilitated their growth.

FIG. 13 shows amino acid sequence for the 2D6C3 Kappa Chain Variable Region. CDR1: RSSQTIVHSNGNTYLE (SEQ ID NO:20); CDR2: KVSNRFS (SEQ ID NO:21); and CDR3: FQGSHVPFT (SEQ ID NO:22).

FIG. 14 shows amino acid sequence for the 2D6C3 Heavy Chain Variable Region. CDR1: GYAMS (SEQ ID NO:23); CDR2: TISSGGTYIYYPDSVKG (SEQ ID NO:24); and CDR3: LGGDNYYEY (SEQ ID NO:25).

FIG. 15 shows amino acid sequence for the 2D6C8 Kappa Chain Variable Region. CDR1: RASKSVSTSGYSYMH (SEQ ID NO:26); CDR2: LVSNLES (SEQ ID NO:27); and CDR3: QHIRELTRSE (SEQ ID NO:28).

FIG. 16 shows amino acid sequence for the 2D6C8 Heavy Chain Variable Region. CDR1: GYAMS (SEQ ID NO:29); CDR2: TISSGGTYIYYPDSVKG (SEQ ID NO:30); and CDR3: LGGDNYYEY (SEQ ID NO:31).

FIG. 17 shows amino acid sequence for the 3C2B1 Kappa Chain Variable Region.

```
CDR1:
                                 (SEQ ID NO: 32)
RASKSISTSDYNYIH;

CDR2:
                                 (SEQ ID NO: 33)
LASNLES; and

CDR3:
                                 (SEQ ID NO: 34)
QHSRELPLTF.
```

FIG. 18 shows amino acid sequence for the 3C2B1 Heavy Chain Variable Region. CDR1: TYTMS (SEQ ID NO:35); CDR2: TISTGGDKTYYSDSVKG (SEQ ID NO:36); and CDR3: GTTAMYYYAM (SEQ ID NO:37).

Example 2.1 Monoclonal Antibodies 2D6C8 or 2D6C3 Coated onto Plasticware Facilitate Attachment of Human ES and iPS Cells Monoclonal antibodies 2D6C8 or 2D6C3 were coated onto a variety of plastic cell culture plates and tested for their ability to capture human stem cells from a variety of sources. Approximately 1 mL of antibody at concentrations ranging from 3 ug/mL to 125 ug/mL was coated onto regular plasticware or tissue culture treated plasticware from a variety of vendors. It was observed that tissue culture treated plates were marginally better than untreated polystyrene for the purpose of attaching antibody and subsequently stem cells to the surface. As in the previous examples, it was observed that growth in minimal stem cell media, MM, alone gave rise to proliferating stem cells, but that proliferation was vastly improved if low nanomolar concentrations of NM23-H1 (dimers) or a bivalent anti-PSMGFR antibody were present in the media.

Figure 2:
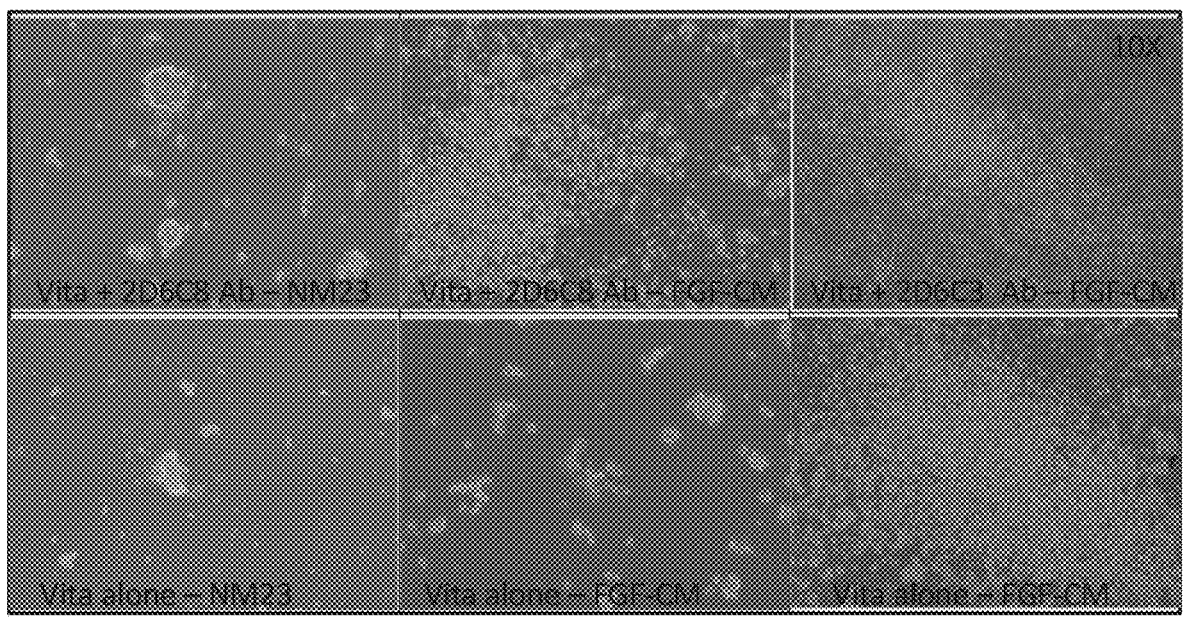
FIG. 2 shows photos of the experiments shown in FIG. 1 of human ES H9 cells plated onto various surfaces and cultured in either NM23 based media or bFGF-media. Images were taken on Day 2 prior to media change and show that only human stem cells plated over the Vita surface or Vita surface coated with an anti-MUC1* antibody and cultured in NM23-based media supported stem cell attachment.
Figure 3:
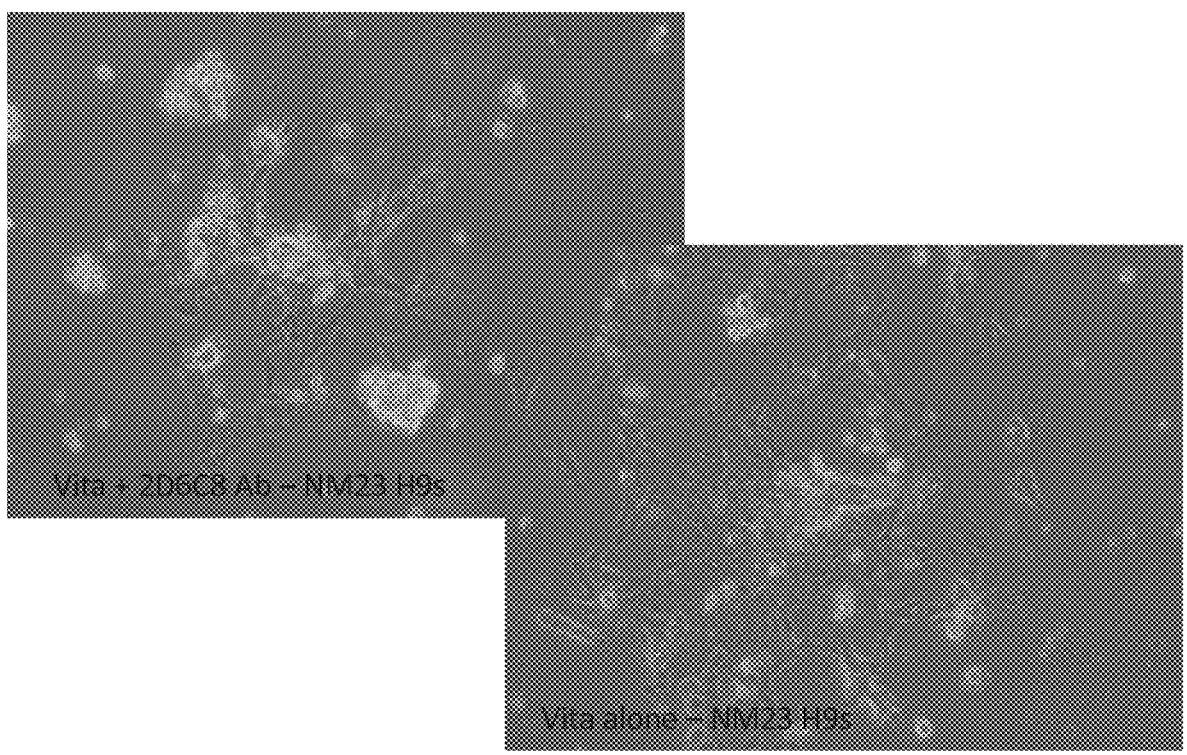
FIG. 3 shows 20× magnification of wells with Vita surface or Vita surface coated with an anti-MUC1* antibody and cultured in NM23-based media on Day 3, and showing pluripotent stem cell growth.
Figure 4:
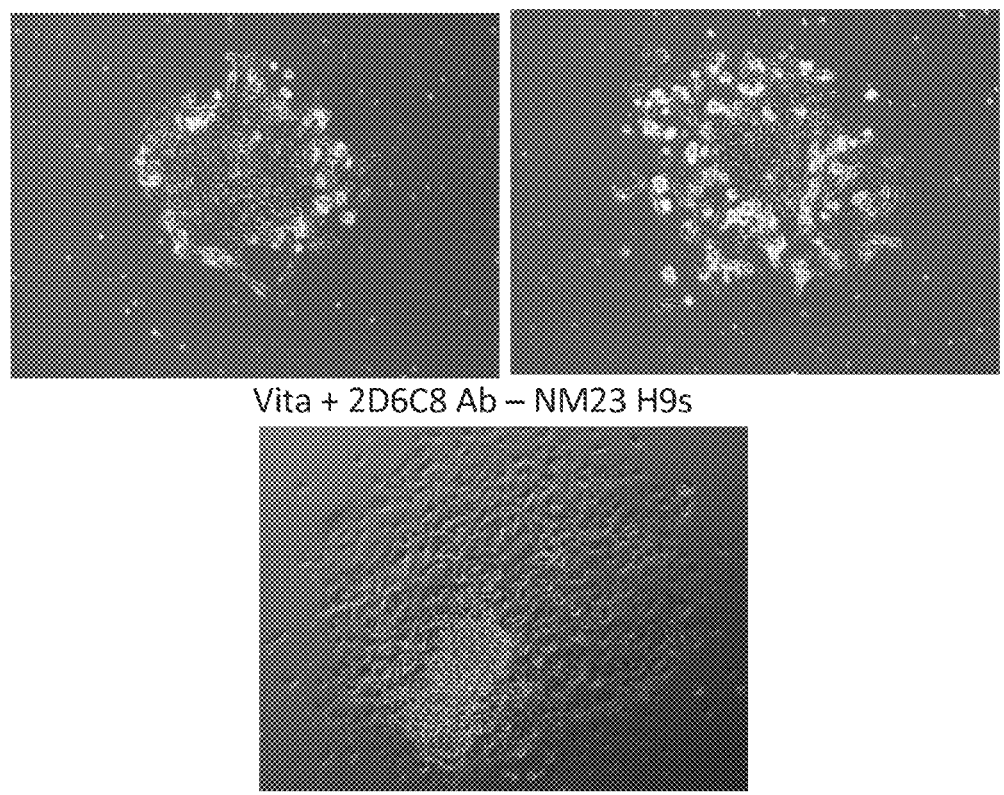
FIG. 4 shows photos of the only 3 colonies that survived as pluripotent stem cells by Day 5, which occurred in well that had a Vita surface coated with monoclonal anti-MUC1* antibody and cultured in NM23-Minimal Media (MM).
Figure 6:
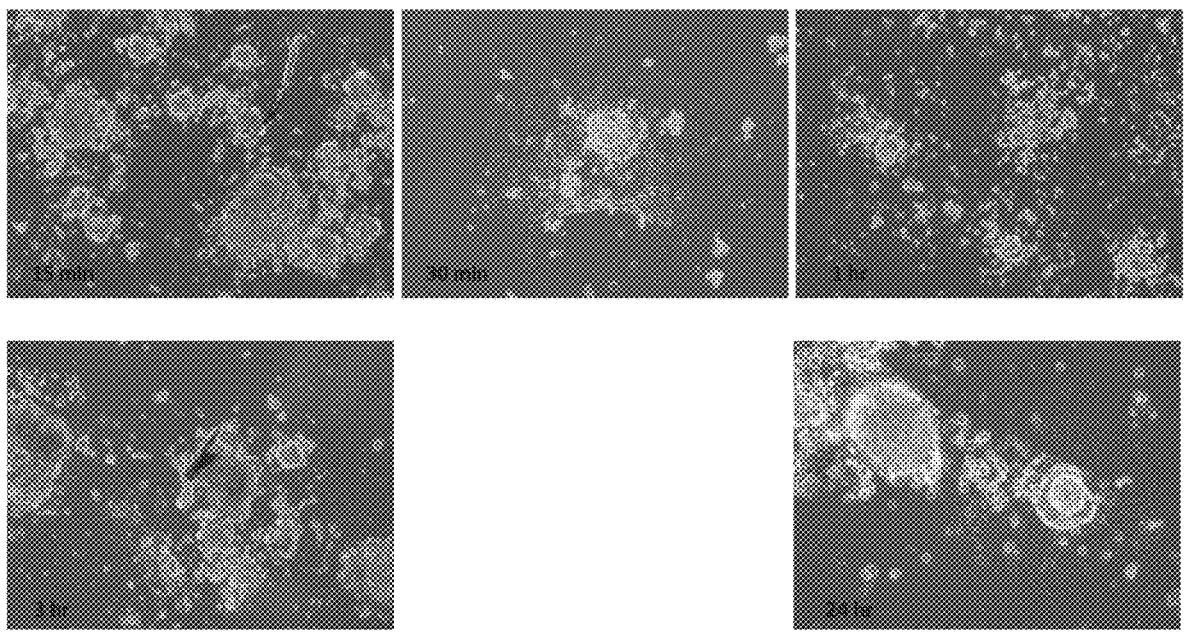
FIG. 6 is a photo showing that human stem cell colony pieces attach better to surfaces if the volume containing the cells is minimized. Times noted in the figure refers to the amount of time that elapsed before NM23 was added to the minimal media (MM).
Figure 7:
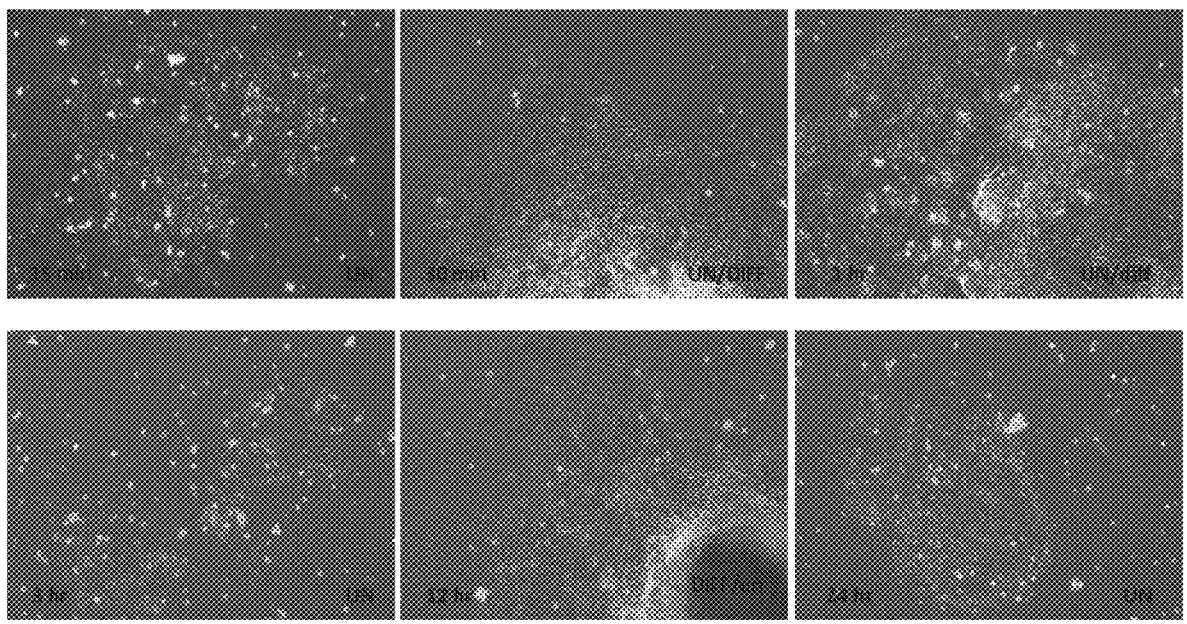
FIG. 7 shows Day 7 photos of the experiment described in FIG. 5 and documents enhanced cellular attachment due to reduced plating volume.

Example 3—Vita Plates Coated with 2D6C8 or 2D6C3 Facilitate Attachment of Both ES and iPS Cell Growth Vita plates (ThermoFisher), bare or coated with 125 μg of either 2D6C8 or 2D6C3 monoclonal anti-MUC1* antibody, were tested for their ability to facilitate stem cell attachment and subsequent growth. Embryonic stem (ES) cells (H9s) that had been grown on MEF feeder cells and cultured in Minimal stem cell Media (MM) plus 8 nM NM23-S120G were manually harvested and colony pieces were plated onto either Vita alone or Vita coated with 2D6C8 mab or Vita+2D6C3 mab. A second source of stem cells was plated over identical surfaces. These were H9 ES cells grown on Matrigel and cultured in 4 ng/ml bFGF+50% conditioned media from mouse embryonic fibroblast (MEF) feeder cells. Undifferentiated colonies were manually dissected and harvested, then plated onto Vita alone or Vita plus an anti-MUC1* antibody. After plating, the stem cells were cultured in whichever media the cells had previously been grown in: 8 nM NM23 in dimeric form or 4 ng/mL bFGF plus 50% conditioned media from mouse feeder cells. Stem cells cultured in NM23-MM attached to both Vita alone and Vita+2D6C8 but, surprisingly, stem cells cultured in bFGF-MEF-CM showed poor attachment and the few cells that did attach differentiated after 1-2 days into fibroblast-like cells or died. The NM23-MM stem cells that bound to the Vita alone surface differentiated more quickly than those on the Vita+2D6C8 antibody surface. By Day 8 post-plating, undifferentiated colonies remained where the source cells had been cultured in NM23 and wherein the surface was a Vita plate coated with an anti-PSMGFR antibody (2D6C8). These colonies were harvested and passaged onto fresh Vita+2D6C8 surfaces, where they continued to grow without reduction in growth rate and as undifferentiated colonies for an additional 5 days. The experimental setup and results are shown in FIG. 1. FIG. 2 shows photographs of the wells as in the experimental setup of FIG. 1, but at Day 2, prior to media change. The cells in the wells cultured in bFGF and conditioned media have not attached and were lost with the first media change. The cells in wells in the left-most column that were cultured in NM23-MM both formed undifferentiated stem cell colonies (FIGS. 2, 3). However, only the surface coated with 2D6C8 antibody produced colonies that remained undifferentiated until Day 5 (FIG. 4), so could be serially passaged. In conclusion, the Vita surface alone did not support human stem cell growth as well as the Vita surface coated with an anti-PSMGFR antibody such as 2D6C8 or 2D6C3. Further, stem cells plated onto a Vita surface, with or without the antibody coating, did not facilitate stem cell growth if cultured in bFGF plus feeder cell conditioned media. The experimental setup of FIG. 5 and images of FIGS. 6 (Day 2) and 7 (Day 7) show that if the volume that the stem cells are in is reduced when cells are plated onto antibody coated surfaces, cell attachment and colony formation is more than tripled. Plating cells in 1 mL, rather than in 4 mL, resulted in up to 14 colonies formed compared to 3 colonies attaching from the larger volume. The times noted in FIGS. 6 and 7 correspond to time between plating cells in MM alone and the time when NM23 in the dimer form was added, which appears to be optimal between 0 minutes and 3 hours post plating.

Figure 9:
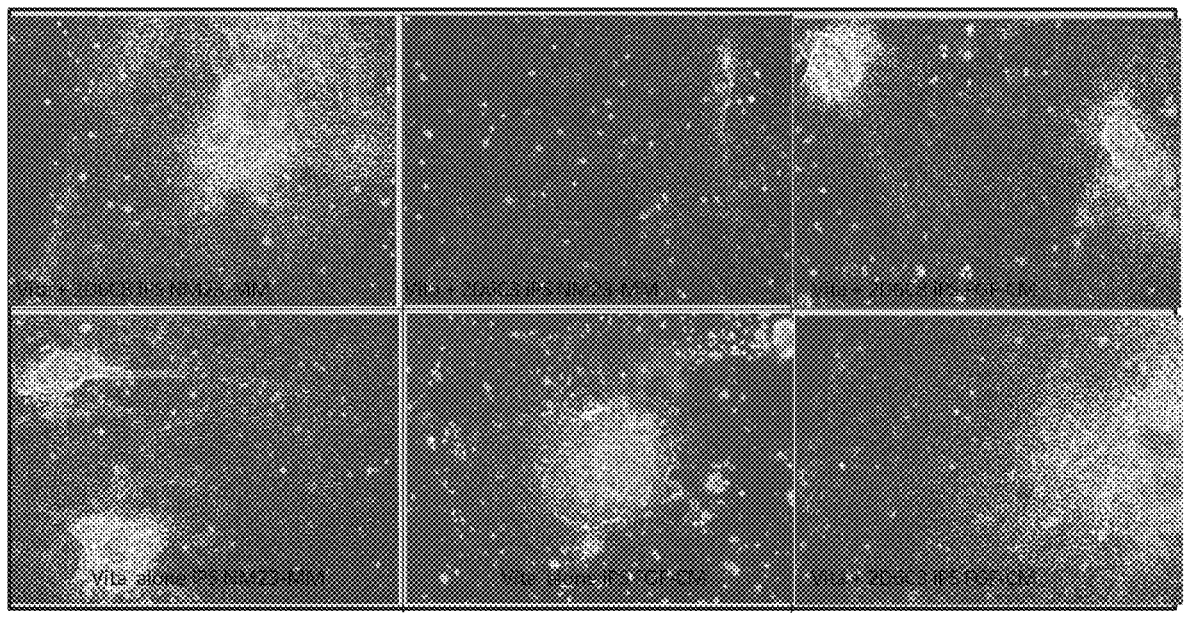
FIG. 9 shows Day 7 photos of human iPS colony pieces from source cells that had previously been grown in either NM23-MM or in bFGF plus MEF conditioned media. In addition, monoclonal antibodies 2D6C3 and 2D6C8 are compared to a Vita surface alone. These iPS cells were first pre-incubated with NM23-MM for 30 minutes prior to plating and were plated in 1 mL MM for 3 hours before volume was increased to 4 mLs in NM23-MM.

Induced pluripotent human stem cells (iPS) cells were assayed according to the experimental setup of FIG. 8 and results shown in FIG. 9. iPS cells from two sources were tested: a) previously cultured in 8 nM NM23-dimers over Matrigel; or b) previously cultured in 4 ng/mL bFGF over mouse fibroblast feeder cells. After plating the stem cell colony pieces in 1 mL of 8 nM NM23 (dimers) in minimal media (MM) and waiting 3 hours, the volume was increased to 4 mLs per well of a 6-well plate. Media was changed every 48 hours. Cells were allowed to grow until Day 7, when cells were becoming overgrown and beginning to differentiate, which allowed for assessing which conditions were best for overall attachment, proliferation and for inhibition of differentiation. In conclusion, both MUC1* antibodies make Vita surfaces better at inhibiting differentiation for longer periods of time. The Vita plus antibody surfaces had colonies that 100% undifferentiated at Day 5 and by Day 7 were showed the most cells and the least differentiation.

Example 4—Optimization of Protocol for Stem Cell Growth on Anti-PSMGFR Antibody Coated Surfaces and in NM23 (Dimer) Containing Media Several factors were identified that improved the efficiency of human ES and iPS cell attachment and proliferation: 1) trypsinized (or otherwise single) stem cells work better than colony pieces when using anti-PSMGFR antibody coated surfaces, especially if the base surface is a surface with atomic composition similar to the Vita surface; 2) cells that were previously cultured in low nanomolar concentrations of dimeric NM23 on other surfaces such as feeder cells or Matrigel, fared better than cells cultured in bFGF, however, this effect could be minimized by a 30 minute incubation in low nanomolar dimer NM23 just prior to plating; and 3) the use of a Rho kinase inhibitor for the first 24 hours after plating improved stem cell attachment, but did not affect stem cell survival. Further, it was noted that decreasing the volume of stem cell growth media from 4 mLs per well of a 6-well plate to 2 mLs or 1 mL enhanced stem cell attachment. Additionally, changing the cell growth media every 24 hours rather than every 48 hours, but using 2 mLs of media rather than 4 mLs was an improvement for the maintenance of some cell types.

Example 4.1—the Effect of Rho Kinase Inhibitor on Stem Cell Culture

In the previous experiments, there was significant loss of stem cells during passaging due to poor attachment or due to cells attaching in clumps. In this experiment we compared attachment, growth and differentiation for both iPS cells and ES H9 cells on either Vita surface plus Rho Kinase inhibitor (ROCi: Y-27632, Calbiochem) or Vita plus anti-MUC1* antibody without ROCi or a Vita surface plus anti-MUC1* antibody plus ROCi. To minimize the cell clumping, undifferentiated stem cell colony pieces were first trypsinized to yield single cells. (Trypsin used at 0.05%, which is 0.5 g/L or 21.45 μM, supplied as 50 ml of a 1× solution, Mediatech, Inc. Cat. No: 25-052.)

Figure 11:
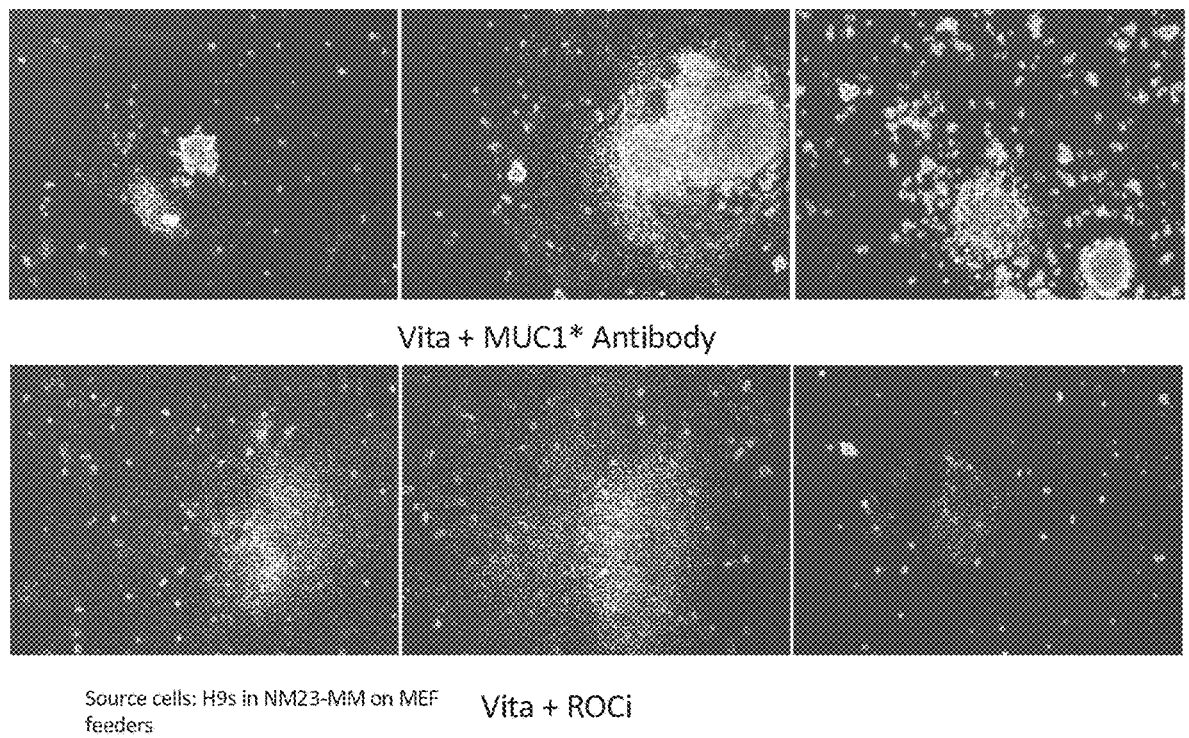
FIG. 11 shows photos of stem cells in an experiment that compared the Vita surfaces alone but with a Rho kinase inhibitor (ROCi) to Vita surface coated with an anti-MUC1* antibody but in the absence of a ROCi.
Figure 12D:
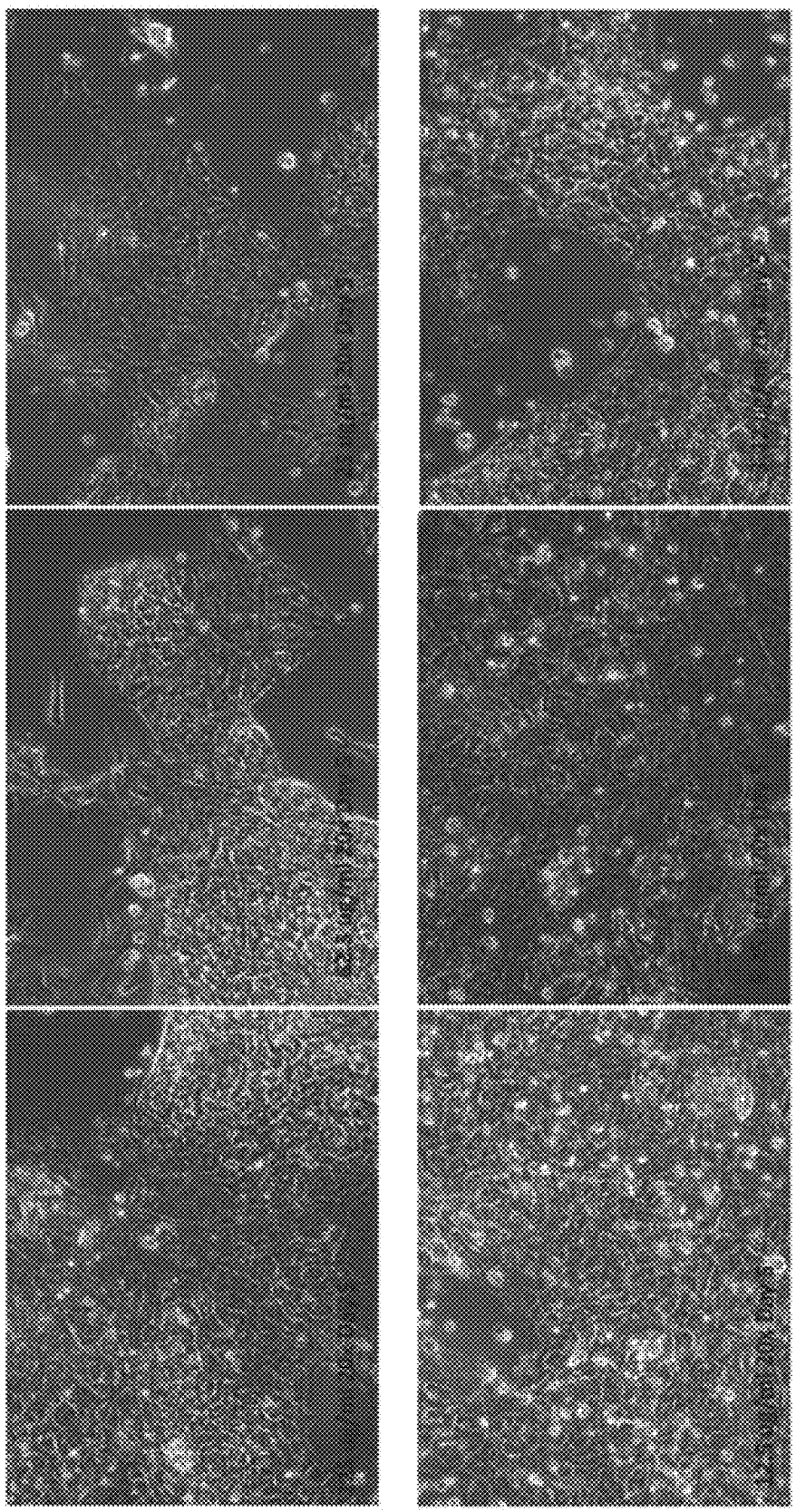
Figure 12E:
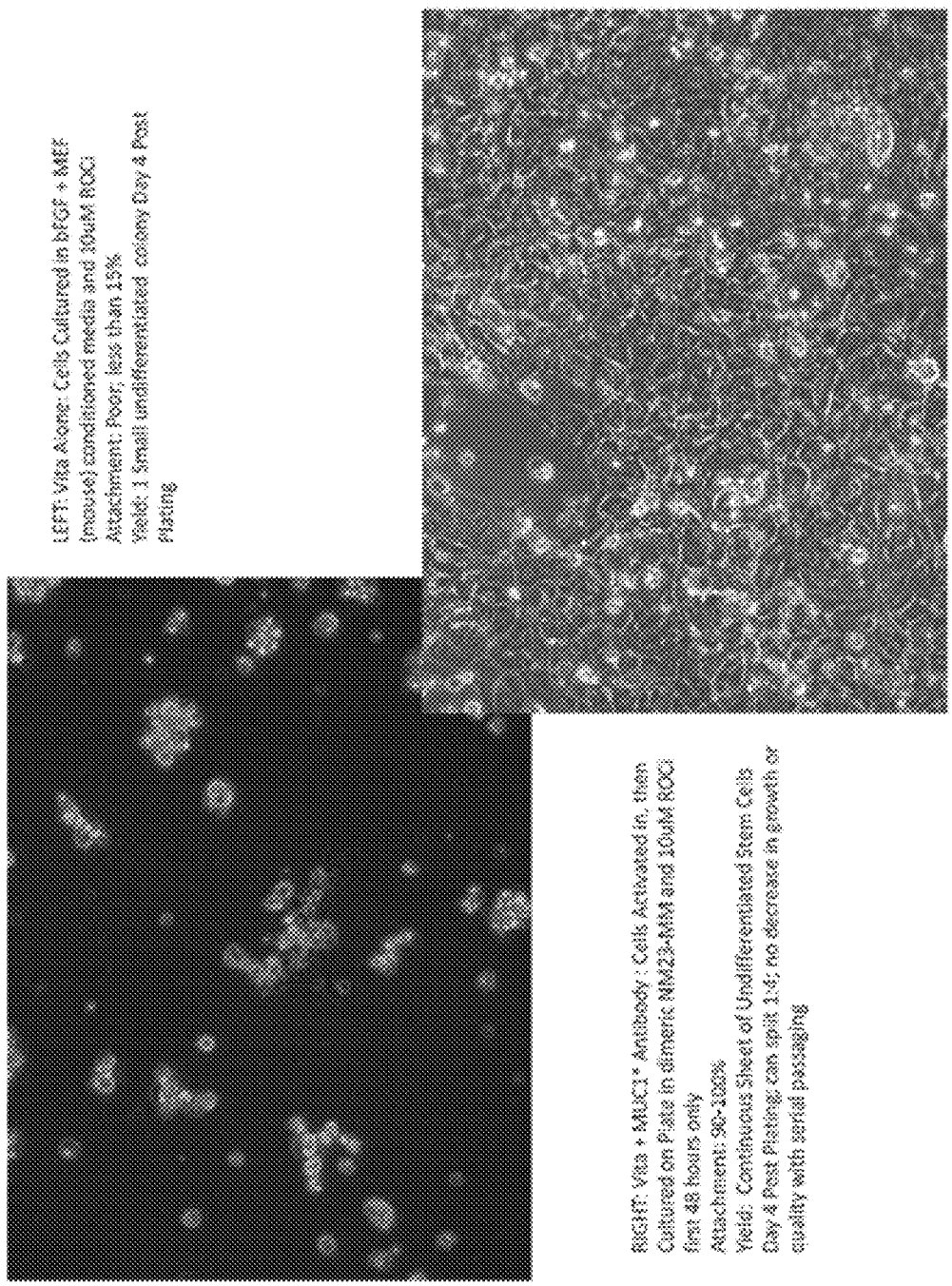
FIG. 12e shows images of human ES cells that were plated onto a Vita surface (no antibody coating) and cultured in standard bFGF plus MEF conditioned media and in the presence of ROCi (upper) compared to the same source cells plated onto a Vita plate coated with an anti-MUC1* antibody and cultured in 8 nM NM23-MM in the presence of ROCi for the first 48 hours only. Images taken Day 4 post plating, see Example 5.

The first part of the experimental setup is shown in FIG. 10. The harvested cells were first pre-incubated in NM23-MM for 15 minutes then rinsed and plated in 1 mL MM per well. 8 nM NM23-S120G was added to a final volume of 4 mLs per well after only 15 minutes. As can be seen in FIG. 11, the Rho kinase inhibitor (ROCi) prevents the clustering of stem cells in solution before they attach to the surface. Although at the end of the experiment, there were comparable numbers of colonies of comparable quality, these results indicate that more colonies would have arisen from a Vita plus antibody surface with ROCi added to NM23-MM at least for the first 24-48 hrs. In fact when ES or iPS cells from any source are trypsinized to single cell suspensions, pre-incubated in low nanomolar concentrations of NM23 in dimer form for at least 15 minutes if previously cultured in bFGF, and plated onto a surface coated with an anti-PSMGFR antibody then cultured in low nanomolar NM23dimers plus a ROCi for the first 24-48 hours, stem cell attachment and proliferation in the undifferentiated state was increased by at least 10-100 times. FIG. 12a shows human ES H9 cells that were harvested from culture in 8 nM NM23dimers-MM over mouse embryonic fibroblast (MEF) feeders, plated onto a Vita surface coated with D26C3 anti-PSMGFR antibody at varying concentrations and in 10 uM ROCi for the first 48 hours only and imaged at Day5 post plating. FIGS. 12b-d are magnified photos of these cells.

Example 5—Improvement to Vita Surface Technology

In this experiment, we compared human stem cell attachment, growth and resistance to spontaneous differentiation for human ES cells, previously cultured in bFGF on MEF feeder cells, then plated as single cells onto: a) a Vita surface, then cultured in 4 ng/mL bFGF, 50% MEF conditioned media and 10 uM ROCi (Y-27632, Calbiochem); or b) Vita plate coated with 12.5 ug/mL D26C3 anti-PSMGFR antibody then cultured in 8 nM NM23dimers-MM with 10 uM ROCi present for the first 48 hours only. The comparison, shown in FIG. 12e shows improvement over the state of the art, which did not include coating the surface with anti-PSMGFR antibody or culturing cells in NM23dimers-MM.

Example 6—the Need for Rho Kinase Inhibitor can be Eliminated

In a direct comparison of stem cell attachment in the presence or absence of the ROCi, we observed that in the absence of ROCi, the stem cells clumped up before they attached to the surface. Some colonies formed beneath the clumps of cells, but more often the cell clumping was inhibitory to the process of stem cell attachment to the surface. It appeared that the improvement we observed for stem cell attachment in the presence of a ROCi was that it kept the cells separate as single cells until they attached to the surface. Alternatively, good stem cell attachment was achieved by trypsinizing the stem cells prior to plating. The addition of EDTA (we used 0.1 to 1.0 mM EDTA) also increased stem cell adhesion to the surfaces. In another method, centrifuging the plates with the stem cells in solution brought the cells in contact with the surface and resulted in stem cell attachment and subsequent growth that was indistinguishable from cases in which 10 uM ROCi was present for the first 24-48 hrs after plating.

Figure 19:
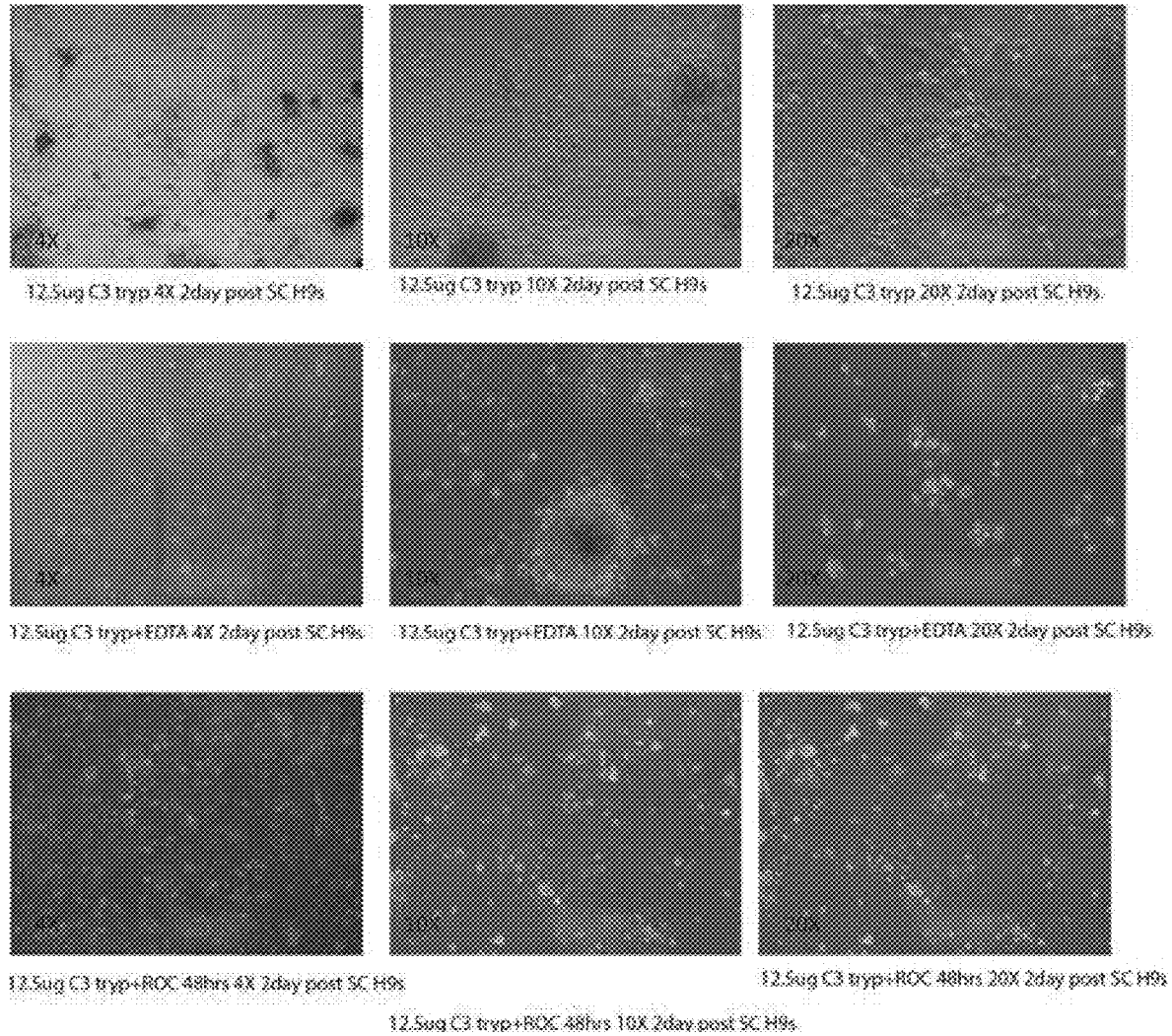
FIG. 19 shows photos of the experiment described in Example 6 comparing attachment of stem cells to surfaces when stem cells were trypsinized prior to plating and in the presence or absence of EDTA or ROCi.
Figure 20:
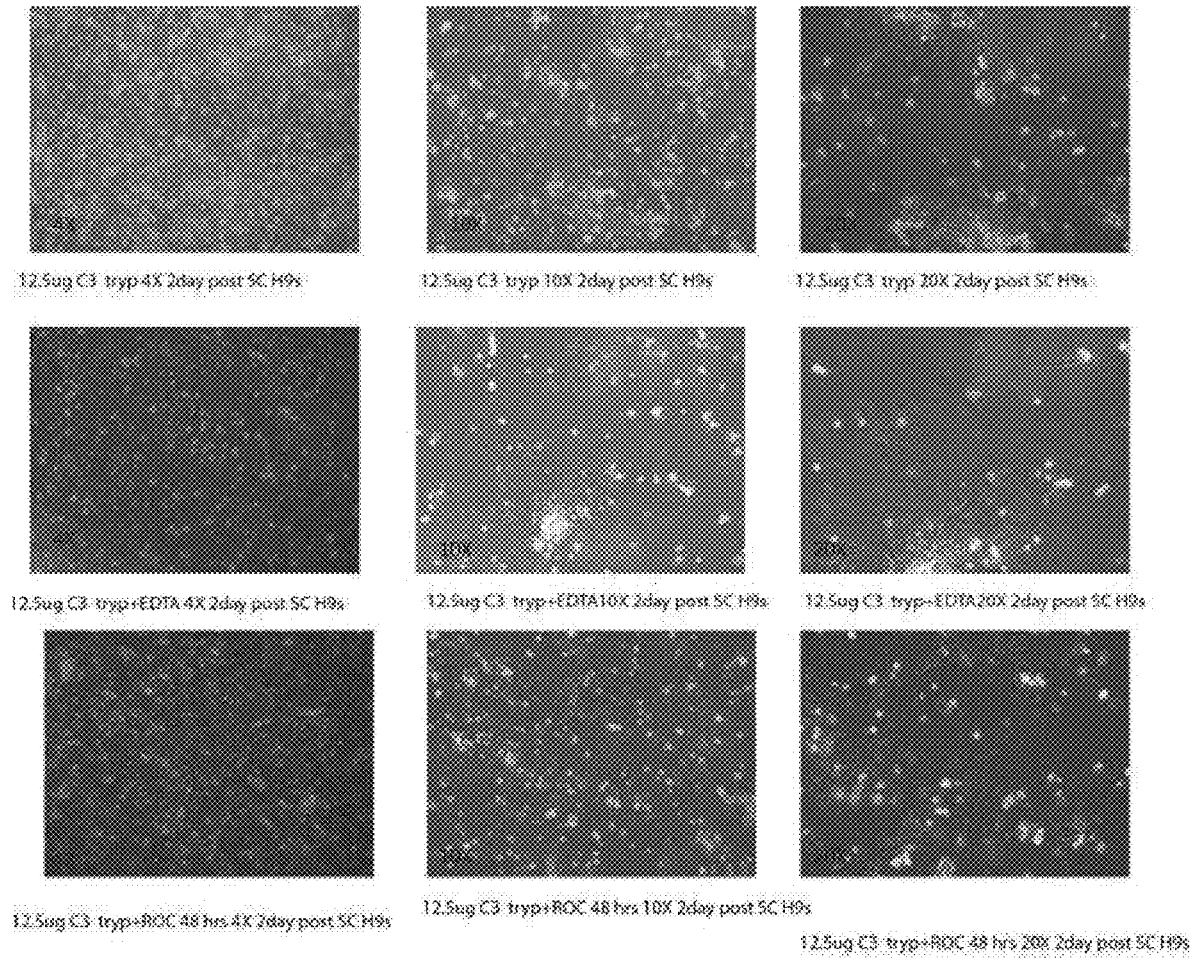
FIG. 20 shows photos of the same experiment described in Example 6 and shown in FIG. 19 with the exception that force was used to bring cells into contact with the surface by centrifuging the plate after cells were plated. Images show that trypsinization plus application of force eliminated need for a Rho kinase inhibitor.

In a model experiment, human ES H9 cells were plated onto a Vita surface coated with an anti-PSMGFR antibody (2D6C3) and the cells were in NM23-MM; the cells were either trypsinized (top row), trypsinized and in 1 mM EDTA (middle), or trypsinized and in presence of 10 uM ROCi (bottom row). As can be seen in FIG. 19, trypsin alone still results in clumping of cells and poor attachment to the surface, trypsin plus EDTA improved cellular attachment but caused the cells to differentiate into neuronal-like phenotype. FIG. 20 shows that under the same conditions, centrifuging the plates greatly improved the attachment of stem cells to the surface. After cells were plated, the plates were centrifuged using a swinging bucket centrifuge at 1200 RPMs for 3-5 minutes. As FIG. 20 shows, physically bringing the cells to the surface eliminated cell clumping and eliminated the need for Rho kinase inhibitor. Similar results can be attained by applying pressure to the cell containing media or any or method that results in an increased probability that the cells will physically meet the surface rather than with a neighboring cell.

Figure 21:
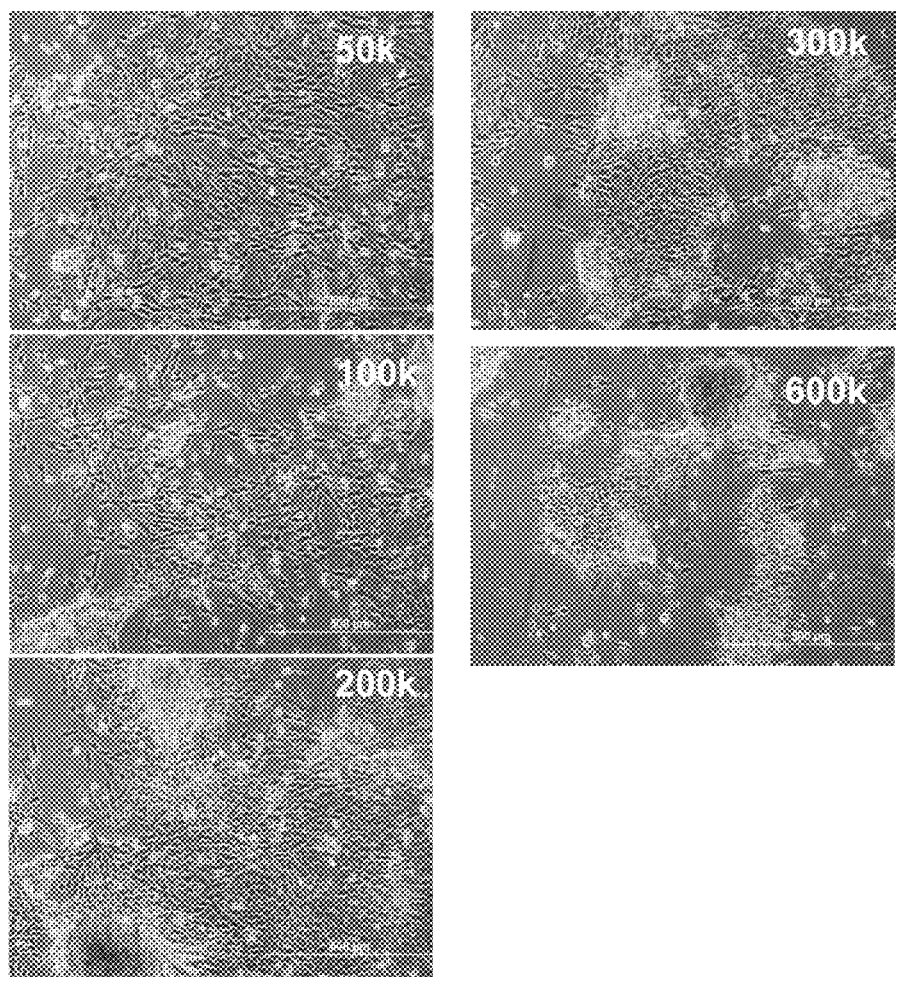
FIG. 21 shows photos of human ES cells plated in the presence or absence of a ROCi and shows that plating trypsinized cells at very low density eliminates the need for a Rho kinase inhibitor to facilitate cellular attachment.

In an alternative method, we found that the use of a Rho Kinase inhibitor could also be eliminated by simply decreasing the plating density of the cells. Cells plated at 25,000 or 50,000 cells per well of a 6-well plate in NM23-MM alone (no ROCi) attached to the surface are proliferated normally and as well as if ROCi had been present. In the experiment shown in FIG. 21, BGO1V/hOG cells were trypsinized, counted and plated at either 25,000 or 50,000 cells per well of a 6-well plate and cultured for 7 days in NM23-MM. No ROCi was used and the cells attached and proliferated indistinguishably from those in which ROCi had been present.

In yet another method, the need for a rho kinase inhibitor is eliminated by simplifying the composition of the base media. Media that contained low nanomolar concentrations of dimeric NM23 but did not contain serum albumin or beta mercaptoethanol eliminated the need for ROCi. For example, human H9 cells cultured in NM23-MN6 (DMEM/F12/GlutaMAX or similar base media suitable for cell culture, supplemented with 1% non-essential amino acids, 64 mg/L ascorbic acid (Sigma), 14 ug/L sodium selenium (Sigma), 19.4 mg/L insulin (Sigma), 543 mg/L sodium bicarbonate (Sigma) and 10.7 mg/L transferrin (Sigma)) did not require the use of a ROCi for 70-90% attachment of stem cells and optimal cell survival. FIG. 26.

Example 7—Different NM23 Multimers are Generated and Assayed for Function

Example 7.1—Cloning of Recombinant NM23-Wt and NM23-S120G

WT NM23-H1 cDNA was amplified by polymerase chain reaction (PCR) using the following primer: 5'-atc gat gga tcc gat ggc caa ctg tga gcg tac c-3' (SEQ ID NO:38) and 5'-gtg gtg ctc gag ttc ata gat cca gtt ctg agc-3' (SEQ ID NO:39). After digestion with BamHI and XhoI restriction enzymes (New England Biolabs), the purified fragment was cloned into the pET21b vector (Novagen) digested with the same restriction enzymes. We then generated the NM23-H1 mutant S120G (serine #120 mutated to a glycine) using the GeneTailor™ Site-directed mutagenesis system (Life Technologies) following the manufacturer instructions using the following primers: 5'-gcaggaacattatacatggcggtgattctg-3' (SEQ ID NO:40) and 5'-gccatgtataatgttcctgccaacttgtat-3' (SEQ ID NO:41). After sequence confirmation, the WT and mutant NM23-H1 constructs were transformed into BL21 (DE3) cells (Life Technologies) for recombinant protein expression.

NM23 S120G-DNA sequence
(SEQ ID NO: 42)
atggccaactgtgagcgtaccttcattgcgatcaaaccagatggggtcca gcggggtcttgtgggagagattatcaagcgttttgagcagaaaggattcc gccttgttggtctgaaattcatgcaagcttccgaagatcttctcaaggaa cactacgttgacctgaaggaccgtccattctttgccggcctggtgaaata catgcactcagggccggtagttgccatggtctgggaggggctgaatgtgg tgaagacgggccgagtcatgctcggggagaccaaccctgcagactccaag cctgggaccatccgtggagacttctgcatacaagttggcaggaacattat acatggcggtgattctgtggagagtgcagagaaggagatcggcttgtggt ttcaccctgaggaactggtagattacacgagctgtgctcagaactggatc tatgaactcgagcaccaccaccaccaccactga NM23 S120G-amino acid sequence
(SEQ ID NO: 43)
MANCERTFIAIKPDGVQRGLVGEIIKRFEQKGFRLVGLKFMQASEDLLKE

HYVDLKDRPFFAGLVKYMHSGPVVAMVWEGLNVVKTGRVMLGETNPADSK

PGTIRGDFCIQVGRNIIHGGDSVESAEKEIGLWFHPEELVDYTSCAQNWI

YELEHHHHHH

Example 7.2—Recombinant NM23-Wt and NM23-S120G Expression/Purification

LB broth (Luria-Bertani broth) was inoculated with 1/10 of an overnight culture and cultured at 37° c. until OD600 reached ~0.5. At this point, recombinant protein expression was induced with 0.4 mM Isopropyl-β-D-thio-galactoside (IPTG, Sigma) and culture was stopped after 4 h. After harvesting the cells by centrifugation (6000 rpm for 10 min at 4° c.), cell pellet was resupended with running buffer: PBS pH7.4, 360 mM NaCl and 80 mM imidazole. Then lysozyme (1 mg/mL, Sigma), $MgCl_2$ (0.5 mM) and DNAse (0.5 ug/mL, Sigma) was added. Cell suspension was incubated on a rotating platform (275 rpm) for 30 min at 37° c. and sonicated on ice for 5 min. Insoluble cell debris was removed by centrifugation (20000 rpm for 30 min at 4° c.). The cleared lysate was then applied to a Ni-NTA column (Qiagen) equilibrated with the running buffer. The column was washed before eluting the protein off the column with the running buffer supplemented with 420 mM imidazole. The elution fractions were analyzed on a non-reducing SDS-PAGE and fractions containing the protein were combined. All components were from Sigma unless otherwise stated.

Example 7.3—Protein Refolding

NM23 H1 S120G was denatured with denaturing buffer: 100 mM Tris pH 8.0 and 8M urea. The denatured protein was then subjected to refolding by dialysis. The protein was dialyzed successively for 24 h against: 1) 100 mM Tris pH8.0, 4M urea, 0.2M imidazole, 0.4M L-Arginine, 1 mM EDTA (Fluka) and 5% glycerol (Acros), 2) 100 mM Tris pH8.0, 2M urea, 0.2M imidazole, 0.4M L-Arginine, 1 mM EDTA and 5% glycerol and 3) 100 mM Tris pH8.0, 1M urea, 0.2M imidazole, 0.4M L-Arginine, 1 mM EDTA and 5% glycerol. The protein was then dialysed against 100 mM Tris pH8.0, 0.2M imidazole, 0.4M L-Arginine, 1 mM EDTA and 5% glycerol for 9 h and against 25 mM Tris pH8.0, 0.2M imidazole, 0.1M L-Arginine, 1 mM EDTA and 5% glycerol overnight. Finally, the protein was dialyzed against PBS pH7.4, 0.2M imidazole, 1 mM EDTA and 5% glycerol for 24 h with four buffer changes. All components were from Sigma unless otherwise stated. Insoluble aggregate was removed by centrifugation (20000 rpm for 30 min at 4° C.) and the dimer (~37 KDa) was purified by size exclusion chromatography on a Superdex 200 10/300 GL column (GE healthcare) using PBS pH7.4 as running buffer. The peak fractions were analyzed on a non-reducing SDS-PAGE and fractions containing the dimer were combined.

Example 7.4—Protein Oligomerization State

The oligomerization state of the NM23 proteins was estimated by size exclusion chromatography using a Superdex 200 10/300 GL column (GE healthcare) calibrated with gel filtration standards (Bio-Rad). A significant feature of NM23 function is its multimerization state, wherein the dimeric form of NM23 is the active form that promotes pluripotency and cell growth.

NM23 H1 isoform was expressed as both the wild type protein (wt) and also bearing the single point mutation, S120G. Analysis by size exclusion chromatography (FIG. 22a), native gel, and Western blot (FIG. S22) indicated that, at concentrations from 8 nM to 13 uM, soluble NM23-wt and soluble NM23-S120G was predominantly hexameric ($NM23_{S120G}$-hexamer). However, using the protein refolding method given above, $NM23_{S120G}$ was denatured and refolded to produce a population consisting primarily of dimer, and which was further purified by size exclusion chromatography to recover a stable population of essentially all dimer ($NM23_{S120G}$-dimer). Thus, we produced NM23-wt and S120G mutant that were both comprised of hexamers and refolded, FPLC purified $NM23_{S120G}$ that was essentially all dimer (FIG. 22a and FIG. S22a-b).

We tested the ability of NM23 hexamers and dimers to bind to the $MUC1*_{ecd}$ peptide in a direct binding assay using Surface Plasmon Resonance, in a Biacore 3000 instrument. A synthetic $MUC1*_{ecd}$ peptide ($PSMGFR-HIS_{6\ tag}$) was immobilized onto a gold chip. NM23-wt, $NM23_{S120G}$-dimer, $NM23_{S120G}$-hexamer, or a sample containing 50% of $NM23_{S120G}$ dimers were separately flowed over the peptide surfaces. The amount of NM23 that bound to the peptide surface was a function of the amount of dimer present in each sample (FIG. 22b). $NM23_{S120G}$-dimers showed robust binding to the immobilized MUC1* peptide, while NM23-wt and $NM23_{S120G}$-hexamer, which are mainly hexamers, showed minimal binding. Note that the SPR signal is directly proportional to the mass of the molecular species bound at the solution-peptide surface interface. Therefore, if the hexameric form of NM23 bound to the MUC1* peptide surface, the greater mass of the hexamer should result in 3-times more resonance units (RUs) than the dimer. The fact that the amount of hexamer binding was minimal is consistent with the idea that NM23 hexamers do not bind to the MUC1* receptor.

A nanoparticle assay was used to characterize the binding of NM23 dimers versus hexamers. A $MUC1*_{ecd}$ peptide (QFNQYKTEAAS-RYNLTISDVSVSDVPFPFSAQSGAHHHHHH) (SEQ ID NO:44) was immobilized on NTA-SAM-coated gold colloids. NM23-wt, $NM23_{S120G}$-dimer and $NM23_{S120G}$-hexamer were expressed and purified with the Strep-tag II (FIG. 22c). The addition of $NM23_{S120G}$-dimer induced a pink to blue solution color change, indicating a specific binding, which was then inhibited by the addition of an anti-MUC1* Fab. Conversely, the addition of NM23-wt or NM23$_{S120G}$-hexamer did not induce a color change, indicating that the hexamers do not bind to the MUC1* receptor (FIG. 22d).

The different NM23 multimers were tested for their ability to maintain pluripotent stem cell growth. Human H9 ES cells were cultured in minimal media (MM) with either NM23-wt, NM23$_{S120G}$-dimer or NM23$_{S120G}$-hexamer. NM23$_{S120G}$-dimers, produced completely undifferentiated stem cells (FIG. 22e), but NM23$_{S120G}$-hexamer and NM23-wt (mostly hexamers) rapidly differentiated (FIG. 22f, g). To further demonstrate that it is the specific interaction of NM23-dimers with MUC1* extra cellular domain that promotes pluripotent growth, we added the synthetic MUC1*$_{ecd}$ peptide (PSMGFR) to stem cells growing in NM23-dimers in minimal media to competitively inhibit this interaction. Disruption of the NM23 dimer-MUC1* interaction resulted in the highest degree of differentiation (FIG. 22h).

Example 7.5—miR-145 Spikes when NM23-MUC1* Interaction is Inhibited

An increase in miR-145 expression signals the stem cells' exit from pluripotency. When growth factor is withheld from stem cell media, which is the standard method for inducing differentiation, there is a corresponding spike in miR-145 expression. RT-PCR measurements showed that competitive inhibition of the NM23$_{S120G}$-dimer-MUC1* interaction by the free MUC1*$_{ecd}$ peptide resulted in an earlier and larger spike in the expression of miR-145 than that caused by allowing cells to differentiate by simply withholding the growth factor NM23$_{S120G}$-dimer or bFGF (FIG. 22i). These results demonstrate that it is the specific interaction of NM23$_{S120G}$-dimer binding to the extra cellular domain of the MUC1* growth factor receptor that promotes pluripotency.

Total RNA was extracted from the samples using the mirVana™ kit (Applied Biosystem, P/N: AM1561) per manufacturer's instructions. For each total RNA sample, two cDNA samples were synthesized using the TaqMan® MicroRNA Reverse Transcription Kit (Applied Biosystems, P/N: 4366596) and two different stem-loop primers specific for miR-145 and the small nuclear RNA U6B (RNU6B), which served as an endogenous control. Quantification of miR-145 and RNU6B in the cDNA samples was performed using TaqMan® MicroRNA Assays (Applied Biosystems, P/N: 4427975) per manufacturer's instructions. The real-time PCR data were analyzed using the comparative $C_t$ method. The relative amount of miR-145 in each sample was obtained by computing the difference between the miR-145 $C_t$ and the corresponding RNU6B $C_t$ ($\Delta C_t$). A second normalization was performed by subtracting the smallest $\Delta C_t$ from all the others in the data set ($\Delta\Delta C_t$).

FIG. 22a shows recombinant NM23 wild type and NM23-S120G mutant were expressed using different protocols that resulted in the formation of different multimerization states and characterized, then purified by size exclusion chromatography. The NM23-S120G mutant was denatured and refolded using a protocol that produces a stable population of dimers. A mixture of the hexamers, tetramers and dimers was generated such that it contained ~50% dimer. FIG. 22b shows that NM23-S120G or wild type multimers were tested by Surface Plasmon Resonance (SPR) to determine their ability to bind to a synthetic MUC1* extra cellular domain (ecd) peptide. The amount of NM23 binding to the MUC1* peptide corresponds to the concentration of dimer present in each sample. FIG. 22c shows recombinant NM23-wt, NM23$_{S120G}$-hexamer and NM23$_{S120G}$-dimer containing the Strep-tag II were characterized by size exclusion chromatography. FIG. 22d shows nanoparticles presenting the MUC1*$_{ecd}$ peptide were mixed with NM23-wt, NM23$_{S120G}$-dimers or -hexamers containing the Strep-tag II. A nanoparticle color change from pink to blue/gray indicates binding. NM23 dimers bind to the MUC1*$_{ecd}$ peptide at 64 nM while the hexamers, whether wild type or S120G mutant, do not. The interaction was competitively inhibited by an anti-MUC1* Fab, showing that the color change was due to the specific interaction between NM23-dimers and MUC1*$_{ecd}$. H9 hES cells were cultured in NM23$_{S120G}$-dimers (FIG. 22e), NM23$_{S120G}$-hexamers (FIG. 22f), wild type (FIG. 22g) or NM23$_{S120G}$-dimers plus a synthetic MUC1*$_{ecd}$ peptide (FIG. 22h). Only NM23$_{S120G}$-dimers supported pluripotent stem cell growth. Hexamers or inhibition of the NM23$_{S120G}$-dimers-MUC1* interaction resulted in immediate differentiation. FIG. 22i shows that H9 hES cells were cultured in either bFGF plus conditioned media or in NM23$_{S120G}$-dimers, then allowed to differentiate by withholding the growth factor. Some cells cultured in NM23$_{S120G}$-dimers continued to receive the growth factor but were also given the MUC1*$_{ecd}$ peptide to competitively inhibit the NM23-MUC1* interaction. miR-145, a marker for exit from pluripotency, is measured by RT-PCR as a function of time.

FIG. S22 shows protocol developed that produces recombinant NM23 as a stable population of dimers. FIG. 22a shows recombinant NM23-wt or S120G mutants that had been purified from the soluble portion, denatured then refolded to form a dimer population or preparation that resulted in an approximate 50/50 mix of dimers and hexamers were analyzed on a native gel to determine which protocols produced which multimers. Protein was loaded at 5 ug and 10 ug total protein per well. FIG. 22b shows that Western blot was performed on a native gel in which the various preparations of NM23-wt or S120G mutant were loaded at very low concentrations comparable to those used in our stem cell culture (8, 16 and 32 nM). FIG. 22c shows that The stability of NM23$_{S120G}$-dimer under culture conditions was tested. NM23$_{S120G}$-dimer was added to cell culture media and kept in a $CO_2$ incubator for up to 48 hours, then analyzed by SDS-PAGE, which showed that no denaturation occurred within the time frame required for use in stem cell culture.

Example 8

Human ES cells cultured long-term in NM23-MM differentiate normally down all three germlines and in most cases displayed coordinated differentiation. H9 hES cells on Matrigel were cultured for six passages in either 8 nM NM23 dimers in MM (minimal stem cell media) or in 4 ng/mL bFGF in MM plus MEF conditioned media, then allowed to differentiate by the embryoid body method. Subsequent staining with nuclear marker DAPI and antibodies against markers of the three germlines: FIG. 23a shows endoderm—alpha feto protein, FIG. 23b shows ectoderm—nestin, and FIG. 23c shows mesoderm—smooth muscle actin. Stem cells cultured in NM23-MM differentiated down all three germlines, wherein most cells in a single cluster stained positive for the same marker. Stem cells cultured in bFGF and MEF conditioned media also differentiated down all three germlines but more often did not display coordinated differentiation, wherein nuclei of nearest neighbors stain negative for the germ line marker being tested (FIGS. 23d-23f).

Example 9—MN-C3 (2D6C3), a Monoclonal Anti-MUC1* Antibody Coated onto Plastic Cell Culture Plates Fully Supports Pluripotent Stem Cell Growth in Combination with Our NM23-Minimal Media 2D6C3 or 2D6C8 monoclonal antibody was coated onto the surfaces of tissue culture treated plates at concentrations from 3.25 to 125 µg/mL and incubated at room temperature for 3 hours or at 4 degrees C. overnight. Human ES and iPS cells readily attached and could be serially passaged on these antibody-coated surfaces. The resultant stem cells were pluripotent as evidenced by ICC staining and RT-PCR for the pluripotency markers.

Example 9.1—Stem Cell Growth Surface

A Vita surface was coated with a monoclonal MUC1*$_{ecd}$ antibody (D26C3) that functions as both a method for stem cell attachment and for stimulating growth by dimerizing the MUC1* receptor. FIGS. 24a-c show that stem cells attached and proliferated as a function of the D26C3 antibody coating density, whereas no stem cell attachment was observed when control antibodies were used. Stem cells proliferated on these MUC1* antibody surfaces even when cultured in minimal stem cell media alone, in the absence of any growth factor—NM23 or bFGF—due to the dimerization of MUC1* from the surface-immobilized antibodies. However, the growth rate was vastly improved by the use of NM23 in the minimal media. In some cases, a Rho kinase inhibitor was present during the first 48 hours, which increased attachment to the surfaces, but did not affect survival. ES and iPS cells were serially passaged on these MUC1* antibody surfaces in NM23-MM for more than 20 passages without a decrease in growth rate or pluripotency. Furthermore, stem cells growing on MUC1* antibody surfaces in NM23-MM undergo a dramatic increase in growth rate with each consecutive passage. By the fourth passage, 600,000 iPS cells plated increased 13-fold to 7.9M undifferentiated stem cells in four days. Similarly, by the fifth passage, H9 cells increased 17-fold (FIGS. 24d-f). ICC staining for the typical pluripotency markers confirmed that the cells were pluripotent and had normal karyotype (FIG. S24a and S24b). In addition, the resultant ES and iPS cells were able to differentiate down all three germlines (FIG. 24 g-l). In summary, growth in NM23-MM on D26C3 antibody surfaces produced more undifferentiated stem cells, in less time, with no manual dissection.

FIG. 24a shows that an anti-MUC1* rabbit polyclonal antibody or a control IgG antibody were adsorbed at varying concentrations onto a tissue culture treated surface. BGO1V/hOG hES cells were plated onto the surfaces and allowed to grow for 96 hours. A Calcein assay to quantify cell number was performed. BGO1V/hOG hES cells were cultured for 20 passages in NM23-MM without a decrease in pluripotency or change in karyotype. H9 hES cells were plated onto Vita surfaces coated with 3.12 ug FIG. 24b or 12.5 ug FIG. 24c of a monoclonal anti-MUC1* antibody, MN-C3. Cells attached and proliferated as a function of antibody concentration. FIG. 24d shows the growth rate of human H9 ES cells or iPS cells increased exponentially after being plated onto the antibody coated surfaces and cultured in NM23-MM. We grew human ES and iPS cells on MN-C3 coated Vita™ plates and cultured them in NM23-MM. At the start of each passage 600,000 cells were plated and then counted after a growth period of 4-6 days. This was repeated for 5-6 passages, each time starting with 600,000 cells from the previous passage. By the fourth passage, 600,000 iPS cells plated increased 13-fold to 7.9M undifferentiated stem cells in four days. By the fifth passage, H9 cells increased 17-fold. It was noted that after three (3) passages on the MN-C3 surfaces, both ES and iPS cells grew to nearly 100% confluency by Day 4 with essentially no differentiation. Photos were taken of the iPS cells (FIG. 24e) and H9 ES cells (FIG. 24f) cultured in NM23-MM on MN-C3 antibody surfaces after passage 4. After 6 passages, resultant cells were allowed to differentiate by embryoid body method. Staining with nuclear marker DAPI and antibodies against markers of the three germlines, endoderm—alpha feto protein (FIGS. 24g and 24j), ectoderm—beta-tubulin (FIGS. 24h and 24K)), and mesoderm—smooth muscle actin (FIGS. 24i and 24l) show that the cells differentiate normally after serial passaging in NM23-MM on anti-MUC1*-coated surfaces.

FIG. S24a shows that hES cultured in NM23-MM on a novel and defined surface for at least 7 passages express typical pluripotency markers. H9s cells on a monoclonal anti-MUC1* antibody (MN-C3) surface were assayed for the presence of the typical pluripotency markers after seven passages. Cells stained positive for typical pluripotency markers and had normal karyotype.

FIG. S24b shows that iPS cultured in NM23-MM on a novel and defined surface for at least 7 passages express typical pluripotency markers. iPS cells (iPS FTD19 clone 42) on a monoclonal anti-MUC1* antibody (MN-C3) surface were assayed for the presence of the typical pluripotency markers after seven passages. Cells stained positive for typical pluripotency markers and had normal karyotype.

Figure 25A:
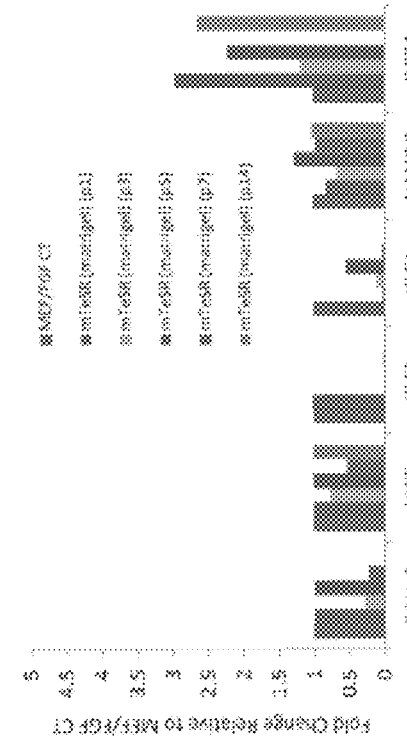

Example 10—Human Stem Cells Cultured in NM23-MM Over MUC1* Antibody Surfaces Express Higher Levels of Naïve Cell Markers and Lower Levels of Primed Cell Markers Example 10.1—Naïve or Primed Cells To further assess the quality of stem cells cultured in NM23-MM on MUC1* antibody surfaces, we measured expression levels of genes that are indicators of human stem cells being in the "naïve" or ground state. Klf4 and Klf2 are usually high in naïve stem cells, while FoxA2 and XIST (an indicator of X-inactivation) are very low or not expressed. The reverse pattern of gene expression happens when cells are in the "primed" state, which is a more differentiated state. We compared expression levels of these genes in stem cells that were cultured in either NM23-MM on MUC1* antibody surfaces, bFGF on MEF feeder cells or mTeSR on Matrigel. Stem cells cultured in NM23-MM on MUC1* antibody surfaces expressed higher levels of the naïve markers and lower levels of the primed markers than cells cultured in bFGF on MEFs. Cells cultured in mTeSR on Matrigel expressed higher levels of Foxa2 and XIST, which are indicators of the primed state, and lower levels of some of the naïve markers compared to cells cultured in bFGF over MEFs (FIG. 25a).

Figure 25B:
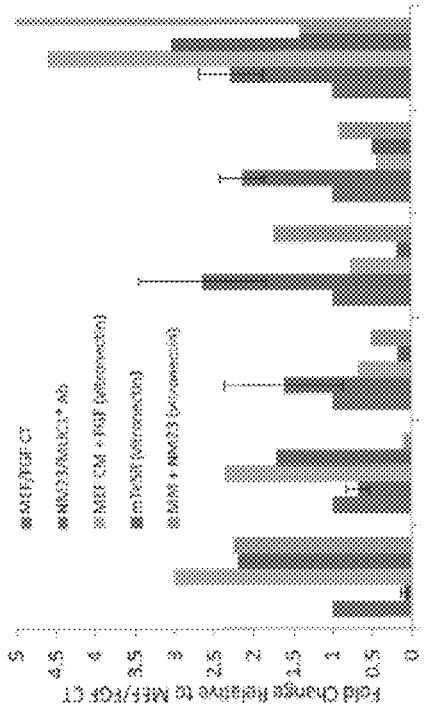
Figure 25C:
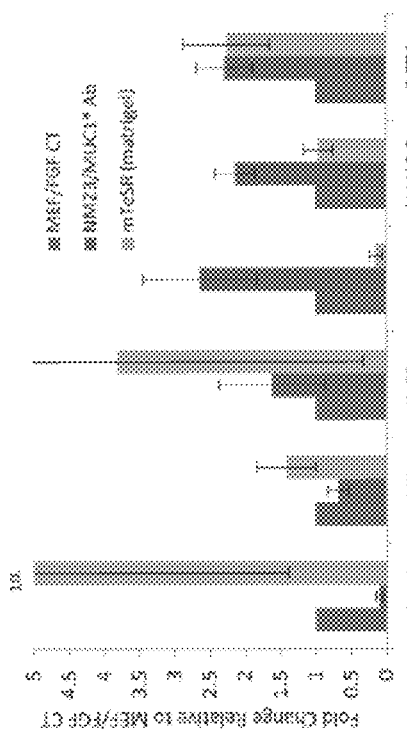

With successive passage number, a trend toward the naïve state was noted when NM23-MM was used (FIG. 25c), but not when mTeSR was used (FIG. 25b). FIG. 37 shows RT-PCR measurements of human stem cells cultured in bFGF over MEF feeders (n=3), mTeSR over Matrigel (n=5)

or NM23-S120G dimers in minimal stem cell media over a Vita surface coated with 12.5 ug/ml of 2D6C3 the monoclonal anti-MUC1* antibody (n=6). In this experiment, two additional primed cell markers, OTX2 and LHX2, were also measured. The graph of FIG. 37 shows that consistent with other experiments, growth in NM23 over a surface presenting ligands for MUC1* increases expression of naïve markers and decreases expression of primed markers.

Figure 25D:
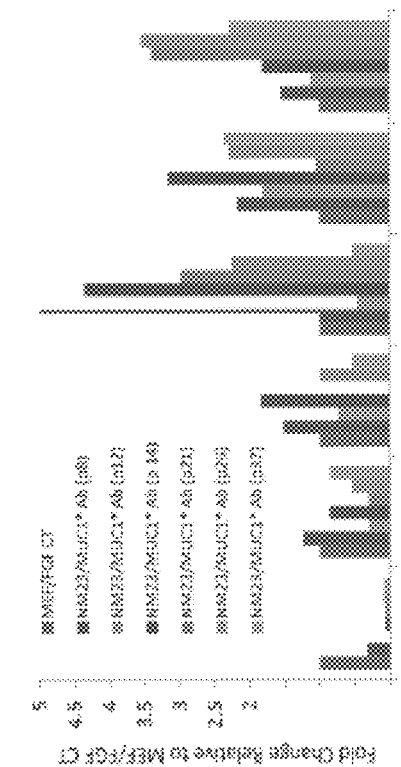
Figure 26A:
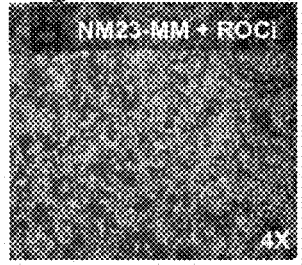
Figure 26B:
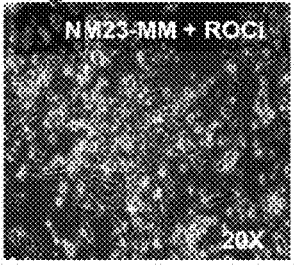
Figure 26C:
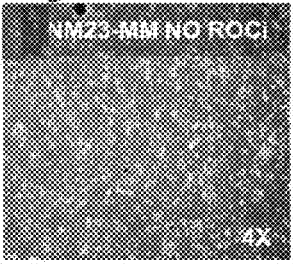
Figure 26D:
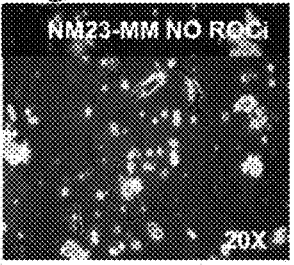
Figure 26E:
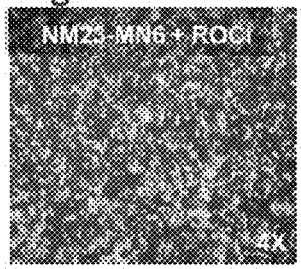
Figure 26F:
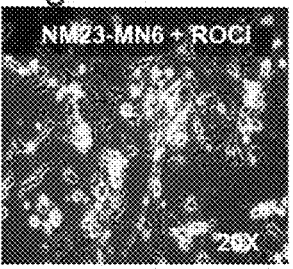
Figure 26G:
Figure 26H:
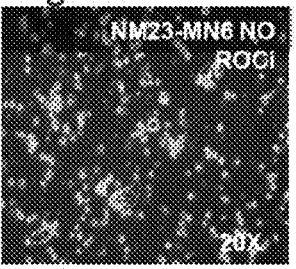
Figure 26I:
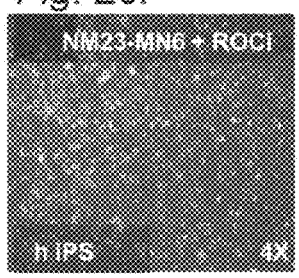
Figure 26J:
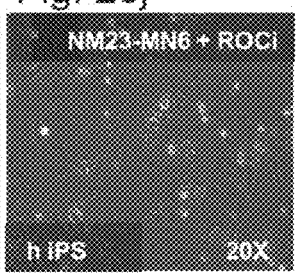
Figure 26K:
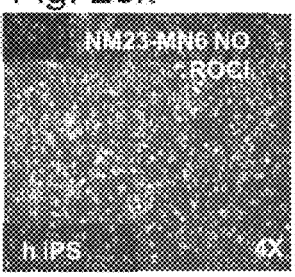
Figure 26L:
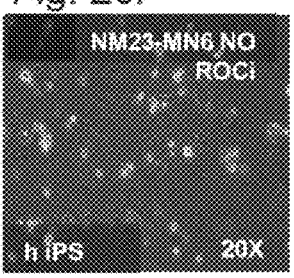
Figure 26M:
Figure 26N:
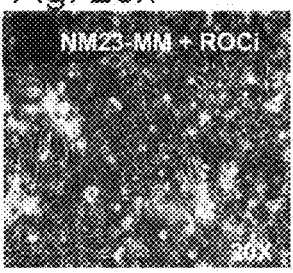
Figure 26O:
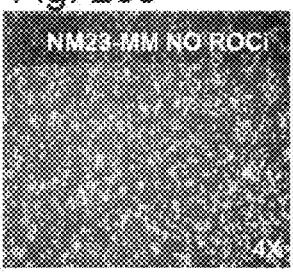
Figure 26P:
Figure 26Q:
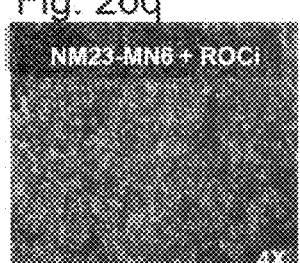
Figure 26R:
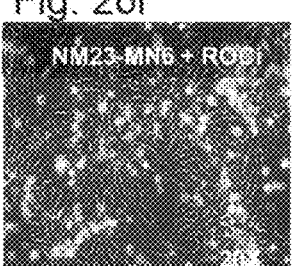
Figure 26S:
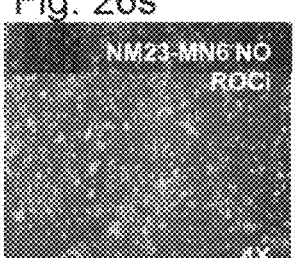
Figure 26T:
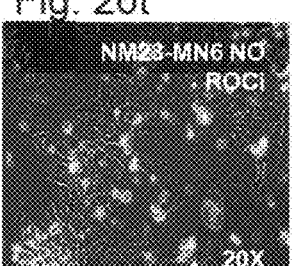

To assess the contribution of surface alone, we plated ES cells that had been growing for 45 passages in bFGF on MEFs onto a layer of recombinant Vitronectin. The cells were then cultured in either NM23-MM, bFGF plus MEF conditioned media or mTeSR for a single passage then assayed for expression of a subset of the naïve and primed markers. Although cells cultured in NM23-MM showed higher expression of the naïve markers and lower expression of the primed markers than either bFGF or mTeSR, growth on Vitronectin resulted in decreased expression of naïve markers and increased expression of primed markers for all the media tested (FIG. 25d). These results show that growth on Vitronectin drives human stem cells to the primed state and negatively impacts the integrity of stem cells.

Example 10.2—Real Time PCR Method for Quantifying Naïve or Primed Gene Expression Cells grown in different conditions were collected. The cells were pelleted and frozen at −70° C. until time of analysis. Total RNA was extracted from the samples using TRIzol® Reagent (Life Technologies) per manufacturer's instructions. Quantification of FOXa2 (Applied Biosystems, Assay ID: Hs00232764 ml), KLF4 (Applied Biosystems, Assay ID:Hs00358836_m1), NANOG (Applied Biosystems, Assay ID: Hs02387400_g1), KLF2 (Applied Biosystems Assay ID: Hs00360439_g1), XIST (Applied biosystems Assay ID: Hs01079824_m1), OCT4 (POU class 5 homeobox 1) (ABI assay ID Hs00999634_gH) and GAPDH (Applied Biosystems, P/N: 4310884E), in the RNA samples was performed using TaqMan® One Step RT-PCR Master Mix Reagents (Applied Biosystems, P/N: 4309169) per manufacturer's instructions. The real-time PCR data were analyzed using the comparative $C_t$ method. The relative amount of each transcript in each sample was obtained by computing the difference between the target $C_t$ and the corresponding GAPDH ($\Delta C_t$). A second normalization was performed by subtracting the MEF/FGF sample $\Delta C_t$ from all the others in the data set ($\Delta \Delta C_t$).

FIG. 25 shows that RT-PCR was used to quantify expression of a subset of naïve markers that included OCT4, NANOG, KLF4 and KLF2, which should be high in the naïve state, and a subset of primed markers that included XIST and FOXA2, which are high in the primed state. Measurements were normalized to housekeeping gene GAPDH and expressed as fold change to H9 ES cells cultured in 4 ng/ml bFGF over MEFs (control). FIG. 25a shows that H9 ES cells cultured in NM23-MM on MUC1* antibody (MN-C3) surfaces, on average, showed increased expression of naïve markers and decreased expression of primed markers (n=6). Conversely, H9 cells cultured in mTeSR over Matrigel showed decreased expression of naïve markers and increased expression of primed markers (n=5). Individual measurements of the subset of naïve or primed markers are plotted as a function of passage number for NM23-MM over anti-MUC1* antibody surfaces (FIG. 25b) and for mTeSR over Matrigel (FIG. 25c). The trend toward the naïve state increased with successive passage in NM23-MM but not with mTeSR. FIG. 25d shows that to correct for differences due to passage number or surfaces, H9 cells that had been serially passaged in bFGF on MEFs for 45 passages were used as the cell source. Cells were plated onto a layer of vitronectin and cultured in either bFGF plus MEF conditioned media, mTeSR, or NM23-MM for a single passage. All values were expressed as fold change to the control of H9 ES cells cultured in 4 ng/ml bFGF over MEFs and values for NM23-MM over MUC1* antibody surface is added for comparison. Overall, expression of naïve markers decreased and primed markers increased after plating onto vitronectin.

Example 11—NM23 in 6-Component Defined and Xeno-Free Media Supports Pluripotent Stem Cell Growth on MUC1* Antibody Surfaces We tested the ability of NM23 to support ES and iPS cell growth as the single growth factor in a fully defined, xeno-free 6-component media (MN6). Our results show that NM23-MN6 fully supported serial passaging of pluripotent stem cells on our MUC1* antibody surfaces as well as on other surfaces such as Vitronectin at 12.5 ug per well (FIG. 26 a-f). Surprisingly, the use of the MN6 media with NM23 appears to eliminate the need for a Rho Kinase inhibitor in the first 24-48 hours (FIG. 26 g-l).

FIG. 26 shows that hES and hiPS cells were serially cultured in NM23 in a 6-component media (MN6) that is fully defined-xeno-free on either a MUC1* antibody surface or on a layer of Vitronectin. FIGS. 26a-26h shows that hES H9s cultured in NM23-MN6 on MN-C3 antibody surface coated onto a Vita™ plate in the presence or absence of a Rho kinase inhibitor (ROCi) for the first 48 hours. FIGS. 26i-26l iPS cells cultured in NM23-MN6 on MN-C3 antibody surface coated onto a Vita™ plate. FIGS. 26m-26t show hES H9 cells cultured in NM23-MN6 on Vitronectin surface coated onto tissue culture treated plates in the presence or absence of a Rho kinase inhibitor (ROCi). The helping effect of a Rho kinase inhibitor for the first 48 hours was minimized when cells were cultured in NM23-MN6 on MN-C3 antibody surfaces.

Example 12—Human Stem Cells Cultured in Either NM23 or FGF Over Human or Mouse Feeder Cells are Probed for the Presence of Markers of Either Naïve State or Primed State We started with H9 embryonic stem cells that were primed. They had been cultured in bFGF and over mouse MEF feeder cells for approximately 30 passages. A first set of cells was continued to be cultured in bFGF over MEFs. A second group was transitioned onto human feeder cells (HS27s) but still cultured in 4 ng/ml of bFGF. A third set of cells was cultured in NM23-S120G but remained on the mouse MEF feeder cells. A fourth set of the cells was transitioned onto human feeder cells (HS27s) and cultured in NM23-S120G. All cells were cultured according to these conditions for an additional 6 passages. The cells were then stained for the presence of Klf4 which is a marker for naïve stem cell state and Foxa2 which is a marker for the primed stem cell state. FIGS. 27-35 show that only cells cultured in NM23 and exposed to human feeder cells expressed naïve stem cell marker Klf4 and did not express any Foxa2 which is the primed stem cell marker.

Example 13—NM23 Mutants that Preferentially Form Dimers and Resist Formation of Inactive Tetramers and Hexamers NM23 mutants that prefer dimer formation have been identified in human cancers. Some of these mutants resist the formation of tetramers and hexamers that do not bind to MUC1* and do not promote pluripotency. Mutants such as NM23-S20G prefer dimer formation over the wild type (wt) protein, but to obtain a solution in which a high concentration of hexamers does not induce differentiation, the S120G mutant is optionally denatured, refolded and the dimer fraction is purified using methods such as FPLC. Mutant NM23-P96S also prefers dimer formation and is more soluble when expressed as the recombinant protein than the S120G mutant. NM23 was generated by typical methods such that it contained the P96S mutation plus 0, 1, 2 or 6 amino acid deletions at the C-terminus. FIG. 36 is an overlay of FPLC traces of the soluble fraction of the expression of the recombinant proteins. FIG. 36 shows that NM23-P96S plus 2 or 6 C-terminal deletions has significant fraction of NM23 in the dimeric form, suitable for MUC1* activation. Preferred is NM23-P96S plus 6 C-terminal deletions because it is predominantly in dimer form as the soluble protein.

Example 14—NM23 P96S and Deletion Constructs

We generated the NM23-H1 mutant P96S (proline #96 mutated to a serine) using the QuickChange site-directed mutagenesis kit (Agilent) following the manufacturer instructions using the following primers: 5'-tcggggagac-caactctgcagactccaag-3' (SEQ ID NO:45) and 5'-cttg-gagtctgcagagttggtctccccga-3' (SEQ ID NO:46). After sequence confirmation, the deletion constructs were generated by PCR. NM23 P96S ΔC1 was amplified using the following primers: 5'-atcgatcatatggccaactgtgagcgtaccttc-3' (SEQ ID NO:47) and 5'-gtggtgaccggtatagatccagttctgagcaca-3' (SEQ ID NO:48). NM23 P96S ΔC2 was amplified using the following primers: 5'-atcgatcatatggccaactgtgagcgtaccttc-3' (SEQ ID NO:49) and 5'-gtggtgaccggtgatccagttct-gagcacagct-3' (SEQ ID NO:50). NM23 P96S ΔC6 was amplified using the following primers: 5'-atcgatcatatggc-caactgtgagcgtaccttc-3' (SEQ ID NO:51) and 5'-gtggtgaccggtagcacagctcgtgtaatctacca-3' (SEQ ID NO:52). The resulting fragments were purified, digested (NdeI, AgeI) and cloned between NdeI and AgeI restriction sites of the expression vector pET21b. The pET21b was previously modified by replacing the XhoI restriction by AgeI.

After sequence confirmation, all constructs were transformed into BL21 (DE3) cells (New England Biolabs) for recombinant protein expression.

NM23 P96S-DNA sequence (SEQ ID NO: 53)
atggccaactgtgagcgtaccttcattgcgatcaaaccagatggggtcc
agcggggtcttgtgggagagattatcaagcgttttgagcagaaaggatt
ccgccttgttggtctgaaattcatgcaagcttccgaagatcttctcaag
gaacactacgttgacctgaaggaccgtccattctttgccggcctggtga
aatacatgcactcagggccggtagttgccatggtctgggaggggctgaa
tgtggtgaagacgggccgagtcatgctcggggagaccaactctgcagac
tccaagcctgggaccatccgtggagacttctgcatacaagttggcagga
acattatacatggcagtgattctgtggagagtgcagagaaggagatcgg
cttgtggtttcaccctgaggaactggtagattacacgagctgtgctcag
aactggatctatgaactcgagcaccaccaccaccactga NM23 P96S-amino acid sequence (SEQ ID NO: 54)
MANCERTFIAIKPDGVQRGLVGEIIKRFEQKGFRLVGLKFMQASEDLLK
EHYVDLKDRPFFAGLVKYMHSGPVVAMVWEGLNVVKTGRVMLGETNSAD
SKPGTIRGDFCIQVGRNIIHGSDSVESAEKEIGLWFHPEELVDYTSCAQ
NWIYELEHHHHHH NM23 P96S ΔC2-DNA sequence (SEQ ID NO: 55)
atggccaactgtgagcgtaccttcattgcgatcaaaccagatggggtcc
agcggggtcttgtgggagagattatcaagcgttttgagcagaaaggatt
ccgccttgttggtctgaaattcatgcaagcttccgaagatcttctcaag
gaacactacgttgacctgaaggaccgtccattctttgccggcctggtga
aatacatgcactcagggccggtagttgccatggtctgggaggggctgaa
tgtggtgaagacgggccgagtcatgctcggggagaccaactctgcagac
tccaagcctgggaccatccgtggagacttctgcatacaagttggcagga
acattatacatggcagtgattctgtggagagtgcagagaaggagatcgg
cttgtggtttcaccctgaggaactggtagattacacgagctgtgctcag
aactggatcaccggtcaccaccaccaccaccactga NM23 P96S ΔC2-amino acid sequence (SEQ ID NO: 56)
MANCERTFIAIKPDGVQRGLVGEIIKRFEQKGFRLVGLKFMQASEDLLK
EHYVDLKDRPFFAGLVKYMHSGPVVAMVWEGLNVVKTGRVMLGETNSAD
SKPGTIRGDFCIQVGRNIIHGSDSVESAEKEIGLWFHPEELVDYTSCAQ
NWITGHHHHHH NM23 P96S ΔC6-DNA sequence (SEQ ID NO: 57)
atggccaactgtgagcgtaccttcattgcgatcaaaccagatggggtcc
agcggggtcttgtgggagagattatcaagcgttttgagcagaaaggatt
ccgccttgttggtctgaaattcatgcaagcttccgaagatcttctcaag
gaacactacgttgacctgaaggaccgtccattctttgccggcctggtga
aatacatgcactcagggccggtagttgccatggtctgggaggggctgaa
tgtggtgaagacgggccgagtcatgctcggggagaccaactctgcagac
tccaagcctgggaccatccgtggagacttctgcatacaagttggcagga
acattatacatggcagtgattctgtggagagtgcagagaaggagatcgg
cttgtggtttcaccctgaggaactggtagattacacgagctgtgctacc
ggtcaccaccaccaccactga NM23 P96S ΔC6-amino acid sequence (SEQ ID NO: 58)
MANCERTFIAIKPDGVQRGLVGEIIKRFEQKGFRLVGLKFMQASEDLLK
EHYVDLKDRPFFAGLVKYMHSGPVVAMVWEGLNVVKTGRVMLGETNSAD
SKPGTIRGDFCIQVGRNIIHGSDSVESAEKEIGLWFHPEELVDYTSCAT
GHHHHHH NM23 P96S ΔC1-DNA sequence (SEQ ID NO: 65)
atggccaactgtgagcgtaccttcattgcgatcaaaccagatggggtcc
agcggggtcttgtgggagagattatcaagcgttttgagcagaaaggatt
ccgccttgttggtctgaaattcatgcaagcttccgaagatcttctcaag
gaacactacgttgacctgaaggaccgtccattctttgccggcctggtga
aatacatgcactcagggccggtagttgccatggtctgggaggggctgaa
tgtggtgaagacgggccgagtcatgctcggggagaccaactctgcagac
tccaagcctgggaccatccgtggagacttctgcatacaagttggcagga
acattatacatggcagtgattctgtggagagtgcagagaaggagatcgg
cttgtggtttcaccctgaggaactggtagattacacgagctgtgctcag
aactggatctataccggtcaccaccaccaccactga NM23 P96S ΔC1-amino acid sequence (SEQ ID NO: 66)
MANCERTFIAIKPDGVQRGLVGEIIKRFEQKGFRLVGLKFMQASEDLLK
EHYVDLKDRPFFAGLVKYMHSGPVVAMVWEGLNVVKTGRVMLGETNSAD
SKPGTIRGDFCIQVGRNIIHGSDSVESAEKEIGLWFHPEELVDYTSCAQ
NWIYTGHHHHHH Below is a comparative amino acid sequences of various NM23 variants.

```
NM23_S120G     MANCERTFTATKPDGVQRGLVGETTKRFEQKGFRLVGLKFMQASEDLLKEHYVDLKDRPF    60
NM23_P96S      MANCERTFTATKPDGVQRGLVGETTKRFEQKGFRLVGLKFMQASEDLLKEHYVDLKDRPF    60
NM23_P96S_C1   MANCERTFTATKPDGVQRGLVGETTKRFEQKGFRLVGLKFMQASEDLLKEHYVDLKDRPF    60
NM23_P96S_C2   MANCERTFTATKPDGVQRGLVGETTKRFEQKGFRLVGLKFMQASEDLLKEHYVDLKDRPF    60
NM23_P96S_C6   MANCERTFTATKPDGVQRGLVGETTKRFEQKGFRLVGLKFMQASEDLLKEHYVDLKDRPF    60

NM23_S120G     FAGLVKYMHSGPVVAMVWEGLNVVKTGRVMLGETNPADSKPGTIRGDFCTQVGRNITHGG   120
NM23_P96S      FAGLVKYMHSGPVVAMVWEGLNVVKTGRVMLGETNSADSKPGTIRGDFCTQVGRNITHGS   120
NM23_P96S_C1   FAGLVKYMHSGPVVAMVWEGLNVVKTGRVMLGETNSADSKPGTIRGDFCTQVGRNITHGS   120
NM23_P96S_C2   FAGLVKYMHSGPVVAMVWEGLNVVKTGRVMLGETNSADSKPGTIRGDFCTQVGRNITHGS   120
NM23_P96S_C6   FAGLVKYMHSGPVVAMVWEGLNVVKTGRVMLGETNSADSKPGTIRGDFCTQVGRNITHGS   120

NM23_S120G     DSVESAEKETGLWFHPEELVDYTSCAQNWTYELEHHHHHH-                     160
NM23_P96S      DSVESAEKETGLWFHPEELVDYTSCAQNWTYELEHHHHHH-                     160
NM23_P96S_C1   DSVESAEKETGLWFHPEELVDYTSCAQNWTY-TGHHHHHH-                     159
NM23_P96S_C2   DSVESAEKETGLWFHPEELVDYTSCAQNWT--TGHHHHHH-                     158
NM23_P96S_C6   DSVESAEKETGLWFHPEELVDYTSCA------TGHHHHHH-                     154
```

Example 15—Protein Expression/Purification

LB broth (Luria-Bertani broth) was inoculated with 1/10 of an overnight culture and cultured at 37° c. until OD600 reached ~-0.5. At this point, recombinant protein expression was induced with 0.4 mM Isopropyl-β-D-thio-galactoside (IPTG, Sigma) and culture was stopped after 4 h. After harvesting the cells by centrifugation (6000 rpm for 10 min at 4° c.), cell pellet was resuspended with running buffer: PBS pH7.4, 360 mM NaCl and 80 mM imidazole. Then lysozyme (1 mg/mL, Sigma), MgCl$_2$ (0.5 mM) and DNAse (0.5 ug/mL, Sigma) were added. Cell suspension was incubated on a rotating platform (275 rpm) for 30 min at 37° c. and sonicated on ice for 5 min. Insoluble cell debris was removed by centrifugation (20000 rpm for 30 min at 4° c.). The cleared lysate was then applied to a Ni-NTA column (Qiagen) equilibrated with the running buffer. The column was washed (8CV) before eluting the protein off the column with the running buffer (6CV) supplemented with 420 mM imidazole. The proteins were further purified by size exclusion chromatography (Superdex 200).

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

---

What is claimed is:

1. An antibody or antibody variant that specifically binds to Primary Sequence of the MUC1 Growth Factor Receptor (PSMGFR), the antibody comprising light chain complementarity-determining regions (CDR-L1, CDR-L2, and CDR-L3) and heavy chain complementarity-determining regions (CDR-H1, CDR-H2, and CDR-H3), wherein:
the CDR-L1 comprises the amino acid sequence of SEQ ID NO: 32;
the CDR-L2 comprises the amino acid sequence of SEQ ID NO: 33;
the CDR-L3 comprises the amino acid sequence of SEQ ID NO: 34;
the CDR-H1 comprises the amino acid sequence of SEQ ID NO: 35;
the CDR-H2 comprises the amino acid sequence of SEQ ID NO: 36; and
the CDR-H3 comprises the amino acid sequence of SEQ ID NO: 37.

2. The antibody or antibody variant of claim 1, which is bivalent.

3. The antibody of claim 1, which is a monoclonal antibody.

4. The antibody or antibody variant of claim 1, comprising a kappa light chain variable region comprising the amino acid sequence of SEQ ID NO: 63.

5. The antibody or antibody variant of claim 1, comprising a heavy chain variable region comprising the amino acid sequence of SEQ ID NO: 64.

6. The antibody or antibody variant of claim 1, comprising a kappa light chain variable region comprising the amino acid sequence of SEQ ID NO: 63 and a heavy chain variable region comprising the amino acid sequence of SEQ ID NO: 64.

* * * * *

SEQUENCE LISTING

```
Sequence total quantity: 66
SEQ ID NO: 1            moltype = AA   length = 1255
FEATURE                 Location/Qualifiers
REGION                  1..1255
                        note = Full-length MUC1 Receptor
source                  1..1255
                        mol_type = protein
                        organism = synthetic construct
SEQUENCE: 1
MTPGTQSPFF LLLLLTVLTV VTGSGHASST PGGEKETSAT QRSSVPSSTE KNAVSMTSSV    60
LSSHSPGSGS STTQGQDVTL APATEPASGS AATWGQDVTS VPVTRPALGS TTPPAHDVTS   120
APDNKPAPGS TAPPAHGVTS APDTRPAPGS TAPPAHGVTS APDTRPAPGS TAPPAHGVTS   180
APDTRPAPGS TAPPAHGVTS APDTRPAPGS TAPPAHGVTS APDTRPAPGS TAPPAHGVTS   240
APDTRPAPGS TAPPAHGVTS APDTRPAPGS TAPPAHGVTS APDTRPAPGS TAPPAHGVTS   300
APDTRPAPGS TAPPAHGVTS APDTRPAPGS TAPPAHGVTS APDTRPAPGS TAPPAHGVTS   360
APDTRPAPGS TAPPAHGVTS APDTRPAPGS TAPPAHGVTS APDTRPAPGS TAPPAHGVTS   420
APDTRPAPGS TAPPAHGVTS APDTRPAPGS TAPPAHGVTS APDTRPAPGS TAPPAHGVTS   480
APDTRPAPGS TAPPAHGVTS APDTRPAPGS TAPPAHGVTS APDTRPAPGS TAPPAHGVTS   540
APDTRPAPGS TAPPAHGVTS APDTRPAPGS TAPPAHGVTS APDTRPAPGS TAPPAHGVTS   600
APDTRPAPGS TAPPAHGVTS APDTRPAPGS TAPPAHGVTS APDTRPAPGS TAPPAHGVTS   660
APDTRPAPGS TAPPAHGVTS APDTRPAPGS TAPPAHGVTS APDTRPAPGS TAPPAHGVTS   720
APDTRPAPGS TAPPAHGVTS APDTRPAPGS TAPPAHGVTS APDTRPAPGS TAPPAHGVTS   780
APDTRPAPGS TAPPAHGVTS APDTRPAPGS TAPPAHGVTS APDTRPAPGS TAPPAHGVTS   840
APDTRPAPGS TAPPAHGVTS APDTRPAPGS TAPPAHGVTS APDTRPAPGS TAPPAHGVTS   900
APDTRPAPGS TAPPAHGVTS APDTRPAPGS TAPPAHGVTS APDNRPALGS TAPPVHNVTS   960
ASGSASGSAS TLVHNGTSAR ATTTPASKST PFSIPSHHSD TPTTLASHST KTDASSTHHS  1020
SVPPLTSSNH STSPQLSTGV SFFFLSFHIS NLQFNSSLED PSTDYYQELQ RDISEMFLQI  1080
YKQGGFLGLS NIKFRPGSVV VQLTLAFREG TINVHDVETQ FNQYKTEAAS RYNLTISDVS  1140
VSDVPFPFSA QSGAGVPGWG IALLVLVCVL VALAIVYLIA LAVCQCRRKN YGQLDIFPAR  1200
DTYHPMSEYP TYHTHGRYVP PSSTDRSPYE KVSAGNGGSS LSYTNPAVAA ASANL       1255

SEQ ID NO: 2            moltype = AA   length = 19
FEATURE                 Location/Qualifiers
REGION                  1..19
                        note = N-terminal MUC-1 signaling sequence for directing
                        MUC1 receptor and truncated isoforms to cell membrane
```

```
                                surface
source                          1..19
                                mol_type = protein
                                organism = synthetic construct
SEQUENCE: 2
MTPGTQSPFF LLLLLTVLT                                                            19

SEQ ID NO: 3                    moltype = AA   length = 23
FEATURE                         Location/Qualifiers
REGION                          1..23
                                note = N-terminal MUC-1 signaling sequence for directing
                                 MUC1 receptor and truncated isoforms to cell membrane
                                 surface
source                          1..23
                                mol_type = protein
                                organism = synthetic construct
SEQUENCE: 3
MTPGTQSPFF LLLLLTVLTV VTA                                                       23

SEQ ID NO: 4                    moltype = AA   length = 23
FEATURE                         Location/Qualifiers
REGION                          1..23
                                note = N-terminal MUC-1 signaling sequence for directing
                                 MUC1 receptor and truncated isoforms to cell membrane
                                 surface
source                          1..23
                                mol_type = protein
                                organism = synthetic construct
SEQUENCE: 4
MTPGTQSPFF LLLLLTVLTV VTG                                                       23

SEQ ID NO: 5                    moltype = AA   length = 146
FEATURE                         Location/Qualifiers
REGION                          1..146
                                note = A truncated MUC1 receptor isoform having nat-PSMGFR
                                 at its N-terminus and including the transmembrane and
                                 cytoplasmic sequences of a full-length MUC1 receptor
source                          1..146
                                mol_type = protein
                                organism = synthetic construct
SEQUENCE: 5
GTINVHDVET QFNQYKTEAA SRYNLTISDV SVSDVPFPFS AQSGAGVPGW GIALLVLVCV   60
LVALAIVYLI ALAVCQCRRK NYGQLDIFPA RDTYHPMSEY PTYHTHGRYV PPSSTDRSPY  120
EKVSAGNGGS SLSYTNPAVA AASANL                                      146

SEQ ID NO: 6                    moltype = AA   length = 171
FEATURE                         Location/Qualifiers
REGION                          1..171
                                note = A truncated MUC1 receptor isoform having nat-PSMGFR
                                 and PSIBR at its N-terminus and including the
                                 transmembrane and cytoplasmic sequences of a full-length
                                 MUC1 receptor
source                          1..171
                                mol_type = protein
                                organism = synthetic construct
SEQUENCE: 6
GFLGLSNIKF RPGSVVVQLT LAFREGTINV HDVETQFNQY KTEAASRYNL TISDVSVSDV   60
PFPFSAQSGA GVPGWGIALL VLVCVLVALA IVYLIALAVC QCRRKNYGQL DIFPARDTYH  120
PMSEYPTYHT HGRYVPPSST DRSPYEKVSA GNGGSSLSYT NPAVAAASAN L           171

SEQ ID NO: 7                    moltype = AA   length = 275
FEATURE                         Location/Qualifiers
REGION                          1..275
                                note = A truncated MUC1 receptor isoform having nat-PSMGFR
                                 + PSIBR + Unique Region at its N-terminus and including
                                 the transmembrane and cytoplasmic sequences of a
                                 full-length MUC1 receptor
source                          1..275
                                mol_type = protein
                                organism = synthetic construct
SEQUENCE: 7
ATTTPASKST PFSIPSHHSD TPTTLASHST KTDASSTHHS TVPPLTSSNH STSPQLSTGV   60
SFFFLSPHIS NLQFNSSLED PSTDYYQELQ RDISEMFLQI YKQGGFLGLS NIKFRPGSVV  120
VQLTLAFREG TINVHDVSVS FNQYKTEAAS RYNLTISDVS VSDVPFPFSA QSGAGVPGWG  180
IALLVLVCVL VALAIVYLIA LAVCQCRRKN YGQLDIFPAR DTYHPMSEYP TYHTHGRYVP  240
PSSTDRSPYE KVSAGNGGSS LSYTNPAVAA ASANL                            275

SEQ ID NO: 8                    moltype = AA   length = 233
FEATURE                         Location/Qualifiers
```

```
REGION                  1..233
                        note = A truncated MUC1 receptor isoform including the
                         transmembrane and cytoplasmic sequences of a full-length
                         MUC1 receptor
source                  1..233
                        mol_type = protein
                        organism = synthetic construct
SEQUENCE: 8
GSGHASSTPG GEKETSATQR SSVPSSTEKN AFNSSLEDPS TDYYQELQRD ISEMFLQIYK    60
QGGFLGLSNI KFRPGSVVVQ LTLAFREGTI NVHDMETQFN QYKTEAASRY NLTISDVSVS   120
DVPFPFSAQS GAGVPGWGIA LLVLVCVLVA LAIVYLIALA VCQCRRKNYG QLDIFPARDT   180
YHPMSEYPTY HTHGRYVPPS STDRSPYEKV SAGNGGSSLS YTNPAVAATS ANL          233

SEQ ID NO: 9            moltype = AA   length = 863
FEATURE                 Location/Qualifiers
REGION                  1..863
                        note = A truncated MUC1 receptor isoform having nat-PSMGFR
                         + PSIBR + Unique Region + Repeats at its N-terminus and
                         including the transmembrane and cytoplasmic sequences of a
                         full-length MUC1 receptor
source                  1..863
                        mol_type = protein
                        organism = synthetic construct
SEQUENCE: 9
LDPRVRTSAP DTRPAPGSTA PQAHGVTSAP DTRPAPGSTA PPAHGVTSAP DTRPAPGSTA    60
PPAHGVTSAP DTRPAPGSTA PPAHGVTSAP DTRPAPGSTA PPAHGVTSAP DTRPAPGSTA   120
PPAHGVTSAP DTRPAPGSTA PPAHGVTSAP DTRPAPGSTA PPAHGVTSAP DTRPAPGSTA   180
PPAHGVTSAP DTRPAPGSTA PPAHGVTSAP DTRPAPGSTA PPAHGVTSAP DTRPAPGSTA   240
PPAHGVTSAP DTRPAPGSTA PPAHGVTSAP DTRPAPGSTA PPAHGVTSAP DTRPAPGSTA   300
PPAHGVTSAP DTRPAPGSTA PPAHGVTSAP DTRPAPGSTA PPAHGVTSAP DTRPAPGSTA   360
PPAHGVTSAP DTRPAPGSTA PPAHGVTSAP DTRPAPGSTA PPAHGVTSAP DTRPAPGSTA   420
PPAHGVTSAP DTRPAPGSTA PPAHGVTSAP DTRPAPGSTA PPAHGVTSAP DTRPAPGSTA   480
PPAHGVTSAP DTRPAPGSTA PPAHGVTSAP DTRPAPGSTA PPAHGVTSAP DTRPAPGSTA   540
PPAHGVTSAP DNRPALGSTA PPVHNVTSAS GSASGSASTL VHNGTSARAT TTPASKSTPF   600
SIPSHHSDTP TTLASHSTKT DASSTHHSSV PPLTSSNHST SPQLSTGVSF FFLSPHISNL   660
QFNSSLEDPS TDYYQELQRD ISEMFLQIYK QGGFLGLSNI KFRPGSVVVQ LTLAFREGTI   720
NVHDVETQFN QYKTEAASRY NLTISDVSVS DVPFPFSAQS GAGVPGWGIA LLVLVCVLVA   780
LAIVYLIALA VCQCRRKNYG QLDIFPARDT YHPMSEYPTY HTHGRYVPPS STDRSPYEKV   840
SAGNGGSSLS YTNPAVAAAS ANL                                          863

SEQ ID NO: 10           moltype = AA   length = 45
FEATURE                 Location/Qualifiers
REGION                  1..45
                        note = Native Primary Sequence of the MUC1 Growth Factor
                         Receptor
source                  1..45
                        mol_type = protein
                        organism = synthetic construct
SEQUENCE: 10
GTINVHDVET QFNQYKTEAA SRYNLTISDV SVSDVPFPFS AQSGA                    45

SEQ ID NO: 11           moltype = AA   length = 44
FEATURE                 Location/Qualifiers
REGION                  1..44
                        note = Native Primary Sequence of the MUC1 Growth Factor
                         Receptor
source                  1..44
                        mol_type = protein
                        organism = synthetic construct
SEQUENCE: 11
TINVHDVETQ FNQYKTEAAS RYNLTISDVS VSDVPFPFSA QSGA                     44

SEQ ID NO: 12           moltype = AA   length = 45
FEATURE                 Location/Qualifiers
REGION                  1..45
                        note = "SPY" functional variant of the native Primary
                         Sequence of the MUC1 Growth Factor Receptor having
                         enhanced stability
source                  1..45
                        mol_type = protein
                        organism = synthetic construct
SEQUENCE: 12
GTINVHDVET QFNQYKTEAA SPYNLTISDV SVSDVPFPFS AQSGA                    45

SEQ ID NO: 13           moltype = AA   length = 44
FEATURE                 Location/Qualifiers
REGION                  1..44
                        note = "SPY" functional variant of the native Primary
                         Sequence of the MUC1 Growth Factor Receptor having
```

-continued

```
                           enhanced stability
source                     1..44
                           mol_type = protein
                           organism = synthetic construct
SEQUENCE: 13
TINVHDVETQ FNQYKTEAAS PYNLTISDVS VSDVPFPFSA QSGA               44

SEQ ID NO: 14              moltype = AA  length = 33
FEATURE                    Location/Qualifiers
REGION                     1..33
                           note = Truncated PSMGFR receptor
source                     1..33
                           mol_type = protein
                           organism = synthetic construct
SEQUENCE: 14
GTINVHDVET QFNQYKTEAA SPYNLTISDV SVS                           33

SEQ ID NO: 15              moltype = AA  length = 48
FEATURE                    Location/Qualifiers
REGION                     1..48
                           note = Extended Sequence of MUC1 Growth Factor Receptor
source                     1..48
                           mol_type = protein
                           organism = synthetic construct
SEQUENCE: 15
VQLTLAFREG TINVHDVETQ FNQYKTEAAS PYNLTISDVS VSDVPFPF           48

SEQ ID NO: 16              moltype = AA  length = 57
FEATURE                    Location/Qualifiers
REGION                     1..57
                           note = Tumor-Specific Extended Sequence of MUC1 Growth
                            Factor Receptor
source                     1..57
                           mol_type = protein
                           organism = synthetic construct
SEQUENCE: 16
SVVVQLTLAF REGTINVHDV ETQFNQYKTE AASPYNLTIS DVSVSDVPFP FSAQSGA  57

SEQ ID NO: 17              moltype = AA  length = 25
FEATURE                    Location/Qualifiers
REGION                     1..25
                           note = Primary Sequence of the Interchain Binding Region
source                     1..25
                           mol_type = protein
                           organism = synthetic construct
SEQUENCE: 17
GFLGLSNIKF RPGSVVVQLT LAFRE                                    25

SEQ ID NO: 18              moltype = AA  length = 13
FEATURE                    Location/Qualifiers
REGION                     1..13
                           note = Truncated Interchain Binding Region
source                     1..13
                           mol_type = protein
                           organism = synthetic construct
SEQUENCE: 18
SVVVQLTLAF REG                                                 13

SEQ ID NO: 19              moltype = AA  length = 40
FEATURE                    Location/Qualifiers
REGION                     1..40
                           note = Repeat Motif 2
source                     1..40
                           mol_type = protein
                           organism = synthetic construct
SEQUENCE: 19
PDTRPAPGST APPAHGVTSA PDTRPAPGST APPAHGVTSA                    40

SEQ ID NO: 20              moltype = AA  length = 16
FEATURE                    Location/Qualifiers
REGION                     1..16
                           note = 2D6C3 Kappa Chain Variable Region - CDR1
source                     1..16
                           mol_type = protein
                           organism = synthetic construct
SEQUENCE: 20
RSSQTIVHSN GNTYLE                                              16

SEQ ID NO: 21              moltype = AA  length = 7
```

```
                            -continued

FEATURE              Location/Qualifiers
REGION               1..7
                     note = 2D6C3 Kappa Chain Variable Region - CDR2
source               1..7
                     mol_type = protein
                     organism = synthetic construct
SEQUENCE: 21
KVSNRFS                                                                  7

SEQ ID NO: 22        moltype = AA  length = 9
FEATURE              Location/Qualifiers
REGION               1..9
                     note = 2D6C3 Kappa Chain Variable Region - CDR3
source               1..9
                     mol_type = protein
                     organism = synthetic construct
SEQUENCE: 22
FQGSHVPFT                                                                9

SEQ ID NO: 23        moltype = AA  length = 5
FEATURE              Location/Qualifiers
REGION               1..5
                     note = 2D6C3 Heavy Chain Variable Region - CDR1
source               1..5
                     mol_type = protein
                     organism = synthetic construct
SEQUENCE: 23
GYAMS                                                                    5

SEQ ID NO: 24        moltype = AA  length = 17
FEATURE              Location/Qualifiers
REGION               1..17
                     note = 2D6C3 Heavy Chain Variable Region - CDR2
source               1..17
                     mol_type = protein
                     organism = synthetic construct
SEQUENCE: 24
TISSGGTYIY YPDSVKG                                                      17

SEQ ID NO: 25        moltype = AA  length = 9
FEATURE              Location/Qualifiers
REGION               1..9
                     note = 2D6C3 Heavy Chain Variable Region - CDR3
source               1..9
                     mol_type = protein
                     organism = synthetic construct
SEQUENCE: 25
LGGDNYYEY                                                                9

SEQ ID NO: 26        moltype = AA  length = 15
FEATURE              Location/Qualifiers
REGION               1..15
                     note = 2D6C8 Kappa Chain Variable Region - CDR1
source               1..15
                     mol_type = protein
                     organism = synthetic construct
SEQUENCE: 26
RASKSVSTSG YSYMH                                                        15

SEQ ID NO: 27        moltype = AA  length = 7
FEATURE              Location/Qualifiers
REGION               1..7
                     note = 2D6C8 Kappa Chain Variable Region - CDR2
source               1..7
                     mol_type = protein
                     organism = synthetic construct
SEQUENCE: 27
LVSNLES                                                                  7

SEQ ID NO: 28        moltype = AA  length = 10
FEATURE              Location/Qualifiers
REGION               1..10
                     note = 2D6C8 Kappa Chain Variable Region - CDR3
source               1..10
                     mol_type = protein
                     organism = synthetic construct
SEQUENCE: 28
QHIRELTRSE                                                              10
```

```
SEQ ID NO: 29          moltype = AA  length = 5
FEATURE                Location/Qualifiers
REGION                 1..5
                       note = 2D6C8 Heavy Chain Variable Region - CDR1
source                 1..5
                       mol_type = protein
                       organism = synthetic construct
SEQUENCE: 29
GYAMS                                                                    5

SEQ ID NO: 30          moltype = AA  length = 17
FEATURE                Location/Qualifiers
REGION                 1..17
                       note = 2D6C8 Heavy Chain Variable Region - CDR2
source                 1..17
                       mol_type = protein
                       organism = synthetic construct
SEQUENCE: 30
TISSGGTYIY YPDSVKG                                                       17

SEQ ID NO: 31          moltype = AA  length = 9
FEATURE                Location/Qualifiers
REGION                 1..9
                       note = 2D6C8 Heavy Chain Variable Region - CDR3
source                 1..9
                       mol_type = protein
                       organism = synthetic construct
SEQUENCE: 31
LGGDNYYEY                                                                9

SEQ ID NO: 32          moltype = AA  length = 15
FEATURE                Location/Qualifiers
REGION                 1..15
                       note = 3C2B1 Kappa Chain Variable Region - CDR1
source                 1..15
                       mol_type = protein
                       organism = synthetic construct
SEQUENCE: 32
RASKSISTSD YNYIH                                                         15

SEQ ID NO: 33          moltype = AA  length = 7
FEATURE                Location/Qualifiers
REGION                 1..7
                       note = 3C2B1 Kappa Chain Variable Region - CDR2
source                 1..7
                       mol_type = protein
                       organism = synthetic construct
SEQUENCE: 33
LASNLES                                                                  7

SEQ ID NO: 34          moltype = AA  length = 10
FEATURE                Location/Qualifiers
REGION                 1..10
                       note = 3C2B1 Kappa Chain Variable Region - CDR3
source                 1..10
                       mol_type = protein
                       organism = synthetic construct
SEQUENCE: 34
QHSRELPLTF                                                               10

SEQ ID NO: 35          moltype = AA  length = 5
FEATURE                Location/Qualifiers
REGION                 1..5
                       note = 3C2B1 Heavy Chain Variable Region - CDR1
source                 1..5
                       mol_type = protein
                       organism = synthetic construct
SEQUENCE: 35
TYTMS                                                                    5

SEQ ID NO: 36          moltype = AA  length = 17
FEATURE                Location/Qualifiers
REGION                 1..17
                       note = 3C2B1 Heavy Chain Variable Region - CDR2
source                 1..17
                       mol_type = protein
                       organism = synthetic construct
SEQUENCE: 36
TISTGGDKTY YSDSVKG                                                       17
```

```
SEQ ID NO: 37              moltype = AA   length = 10
FEATURE                    Location/Qualifiers
REGION                     1..10
                           note = 3C2B1 Heavy Chain Variable Region - CDR3
source                     1..10
                           mol_type = protein
                           organism = synthetic construct
SEQUENCE: 37
GTTAMYYYAM                                                                 10

SEQ ID NO: 38              moltype = DNA   length = 34
FEATURE                    Location/Qualifiers
misc_feature               1..34
                           note = Primer for WT NM23-H1 cDNA
source                     1..34
                           mol_type = other DNA
                           organism = synthetic construct
SEQUENCE: 38
atcgatggat ccgatggcca actgtgagcg tacc                                      34

SEQ ID NO: 39              moltype = DNA   length = 33
FEATURE                    Location/Qualifiers
misc_feature               1..33
                           note = Primer for WT NM23-H1 cDNA
source                     1..33
                           mol_type = other DNA
                           organism = synthetic construct
SEQUENCE: 39
gtggtgctcg agttcataga tccagttctg agc                                       33

SEQ ID NO: 40              moltype = DNA   length = 30
FEATURE                    Location/Qualifiers
misc_feature               1..30
                           note = Primer for NM23-H1 mutant S120G
source                     1..30
                           mol_type = other DNA
                           organism = synthetic construct
SEQUENCE: 40
gcaggaacat tatacatggc ggtgattctg                                           30

SEQ ID NO: 41              moltype = DNA   length = 30
FEATURE                    Location/Qualifiers
misc_feature               1..30
                           note = Primer for NM23-H1 mutant S120G
source                     1..30
                           mol_type = other DNA
                           organism = synthetic construct
SEQUENCE: 41
gccatgtata atgttcctgc caacttgtat                                           30

SEQ ID NO: 42              moltype = DNA   length = 483
FEATURE                    Location/Qualifiers
misc_feature               1..483
                           note = NM23 S120G
source                     1..483
                           mol_type = other DNA
                           organism = synthetic construct
SEQUENCE: 42
atggccaact gtgagcgtac cttcattgcg atcaaaccag atggggtcca gcggggtctt          60
gtgggagaga ttatcaagcg ttttgagcag aaaggattcc gccttgttgg tctgaaattc         120
atgcaagctt ccgaagatct tctcaaggaa cactacgttg acctgaagga ccgtccattc         180
tttgccggcc tggtgaaata catgcactca gggccgtag ttgccatggt ctgggagggg          240
ctgaatgtgg tgaagacggg ccgagtcatg ctcgggggaga ccaaccctgc agactccaag        300
cctgggacca tccgtggaga cttctgcata caagttggca ggaacattat acatggcggt         360
gattctgtgg agagtgcaga aaggagatc ggcttgtggt ttcaccctga ggaactggta          420
gattacacga gctgtgctca gaactggatc tatgaactcg agcaccacca ccaccaccac         480
tga                                                                      483

SEQ ID NO: 43              moltype = AA   length = 160
FEATURE                    Location/Qualifiers
REGION                     1..160
                           note = NM23 S120G
source                     1..160
                           mol_type = protein
                           organism = synthetic construct
SEQUENCE: 43
MANCERTFIA IKPDGVQRGL VGEIIKRFEQ KGFRLVGLKF MQASEDLLKE HYVDLKDRPF          60
FAGLVKYMHS GPVVAMVWEG LNVVKTGRVM LGETNPADSK PGTIRGDFCI QVGRNIIHGG        120
```

```
DSVESAEKEI GLWFHPEELV DYTSCAQNWI YELEHHHHHH                                  160

SEQ ID NO: 44           moltype = AA   length = 41
FEATURE                 Location/Qualifiers
REGION                  1..41
                        note = MUC1*ecd peptide
source                  1..41
                        mol_type = protein
                        organism = synthetic construct
SEQUENCE: 44
QFNQYKTEAA SRYNLTISDV SVSDVPFPFS AQSGAHHHHH H                                 41

SEQ ID NO: 45           moltype = DNA   length = 29
FEATURE                 Location/Qualifiers
misc_feature            1..29
                        note = Primer for NM23-H1 mutant P96S
source                  1..29
                        mol_type = other DNA
                        organism = synthetic construct
SEQUENCE: 45
tcggggagac caactctgca gactccaag                                              29

SEQ ID NO: 46           moltype = DNA   length = 29
FEATURE                 Location/Qualifiers
misc_feature            1..29
                        note = Primer for NM23-H1 mutant P96S
source                  1..29
                        mol_type = other DNA
                        organism = synthetic construct
SEQUENCE: 46
cttggagtct gcagagttgg tctccccga                                              29

SEQ ID NO: 47           moltype = DNA   length = 33
FEATURE                 Location/Qualifiers
misc_feature            1..33
                        note = Primer for NM23 P96S C1
source                  1..33
                        mol_type = other DNA
                        organism = synthetic construct
SEQUENCE: 47
atcgatcata tggccaactg tgagcgtacc ttc                                          33

SEQ ID NO: 48           moltype = DNA   length = 33
FEATURE                 Location/Qualifiers
misc_feature            1..33
                        note = Primer for NM23 P96S C1
source                  1..33
                        mol_type = other DNA
                        organism = synthetic construct
SEQUENCE: 48
gtggtgaccg gtatagatcc agttctgagc aca                                          33

SEQ ID NO: 49           moltype = DNA   length = 33
FEATURE                 Location/Qualifiers
misc_feature            1..33
                        note = Primer for NM23 P96S C2
source                  1..33
                        mol_type = other DNA
                        organism = synthetic construct
SEQUENCE: 49
atcgatcata tggccaactg tgagcgtacc ttc                                          33

SEQ ID NO: 50           moltype = DNA   length = 33
FEATURE                 Location/Qualifiers
misc_feature            1..33
                        note = Primer for NM23 P96S C2
source                  1..33
                        mol_type = other DNA
                        organism = synthetic construct
SEQUENCE: 50
gtggtgaccg gtgatccagt tctgagcaca gct                                          33

SEQ ID NO: 51           moltype = DNA   length = 33
FEATURE                 Location/Qualifiers
misc_feature            1..33
                        note = Primer for NM23 P96S C6
source                  1..33
                        mol_type = other DNA
                        organism = synthetic construct
```

```
SEQUENCE: 51
atcgatcata tggccaactg tgagcgtacc ttc                                    33

SEQ ID NO: 52           moltype = DNA   length = 35
FEATURE                 Location/Qualifiers
misc_feature            1..35
                        note = Primer for NM23 P96S C6
source                  1..35
                        mol_type = other DNA
                        organism = synthetic construct
SEQUENCE: 52
gtggtgaccg gtagcacagc tcgtgtaatc tacca                                  35

SEQ ID NO: 53           moltype = DNA   length = 483
FEATURE                 Location/Qualifiers
misc_feature            1..483
                        note = NM23 P96S
source                  1..483
                        mol_type = other DNA
                        organism = synthetic construct
SEQUENCE: 53
atggccaact gtgagcgtac cttcattgcg atcaaaccag atggggtcca gcggggtctt       60
gtgggagaga ttatcaagcg ttttgagcag aaaggattcc gccttgttgg tctgaaattc      120
atgcaagctt ccgaagatct tctcaaggaa cactacgttg acctgaagga ccgtccattc      180
tttgccggcc tggtgaaata catgcactca gggccggtag ttgccatggt ctgggagggg      240
ctgaatgtgg tgaagacggg ccgagtcatg ctcggggaga ccaactctgc agactccaag      300
cctgggacca tccgtggaga cttctgcata caagttggca ggaacattat acatggcagt      360
gattctgtgg agagtgcaga aaggagatc ggcttgtggt ttcaccctga gaactggta       420
gattacacga gctgtgctca aactggatc tatgaactcg agcaccacca ccaccaccac      480
tga                                                                    483

SEQ ID NO: 54           moltype = AA   length = 160
FEATURE                 Location/Qualifiers
REGION                  1..160
                        note = NM23 P96S
source                  1..160
                        mol_type = protein
                        organism = synthetic construct
SEQUENCE: 54
MANCERTFIA IKPDGVQRGL VGEIIKRFEQ KGFRLVGLKF MQASEDLLKE HYVDLKDRPF        60
FAGLVKYMHS GPVVAMVWEG LNVVKTGRVM LGETNSADSK PGTIRGDFCI QVGRNIIHGS      120
DSVESAEKEI GLWFHPEELV DYTSCAQNWI YELEHHHHHH                            160

SEQ ID NO: 55           moltype = DNA   length = 477
FEATURE                 Location/Qualifiers
misc_feature            1..477
                        note = NM23 P96S C2
source                  1..477
                        mol_type = other DNA
                        organism = synthetic construct
SEQUENCE: 55
atggccaact gtgagcgtac cttcattgcg atcaaaccag atggggtcca gcggggtctt       60
gtgggagaga ttatcaagcg ttttgagcag aaaggattcc gccttgttgg tctgaaattc      120
atgcaagctt ccgaagatct tctcaaggaa cactacgttg acctgaagga ccgtccattc      180
tttgccggcc tggtgaaata catgcactca gggccggtag ttgccatggt ctgggagggg      240
ctgaatgtgg tgaagacggg ccgagtcatg ctcggggaga ccaactctgc agactccaag      300
cctgggacca tccgtggaga cttctgcata caagttggca ggaacattat acatggcagt      360
gattctgtgg agagtgcaga aaggagatc ggcttgtggt ttcaccctga gaactggta       420
gattacacga gctgtgctca aactggatc accggtcacc accaccacca ccactga         477

SEQ ID NO: 56           moltype = AA   length = 158
FEATURE                 Location/Qualifiers
REGION                  1..158
                        note = NM23 P96S C2
source                  1..158
                        mol_type = protein
                        organism = synthetic construct
SEQUENCE: 56
MANCERTFIA IKPDGVQRGL VGEIIKRFEQ KGFRLVGLKF MQASEDLLKE HYVDLKDRPF        60
FAGLVKYMHS GPVVAMVWEG LNVVKTGRVM LGETNSADSK PGTIRGDFCI QVGRNIIHGS      120
DSVESAEKEI GLWFHPEELV DYTSCAQNWI TGHHHHHH                              158

SEQ ID NO: 57           moltype = DNA   length = 465
FEATURE                 Location/Qualifiers
misc_feature            1..465
                        note = NM23 P96S C6
source                  1..465
                        mol_type = other DNA
                        organism = synthetic construct
```

-continued

```
SEQUENCE: 57
atggccaact gtgagcgtac cttcattgcg atcaaaccag atggggtcca gcggggtctt      60
gtgggagaga ttatcaagcg ttttgagcag aaaggattcc gccttgttgg tctgaaattc     120
atgcaagctt ccgaagatct tctcaaggaa cactacgttg acctgaagga ccgtccattc     180
tttgccggcc tggtgaaata catgcactca gggccggtag ttgccatggt ctgggagggg     240
ctgaatgtgg tgaagacggg ccgagtcatg ctcggggaga ccaactctgc agactccaag     300
cctgggacca tccgtggaga cttctgcata caagttggca ggaacattat acatggcagt     360
gattctgtgg agagtgcaga gaaggagatc ggcttgtggt ttcaccctga ggaactggta     420
gattacacga gctgtgctac cggtcaccac caccaccacc actga                     465

SEQ ID NO: 58           moltype = AA   length = 154
FEATURE                 Location/Qualifiers
REGION                  1..154
                        note = NM23 P96S C6
source                  1..154
                        mol_type = protein
                        organism = synthetic construct
SEQUENCE: 58
MANCERTFIA IKPDGVQRGL VGEIIKRFEQ KGFRLVGLKF MQASEDLLKE HYVDLKDRPF      60
FAGLVKYMHS GPVVAMVWEG LNVVKTGRVM LGETNSADSK PGTIRGDFCI QVGRNIIHGS     120
DSVESAEKEI GLWFHPEELV DYTSCATGHH HHHH                                 154

SEQ ID NO: 59           moltype = AA   length = 102
FEATURE                 Location/Qualifiers
REGION                  1..102
                        note = 2D6C3 Kappa Chain Variable Region
source                  1..102
                        mol_type = protein
                        organism = synthetic construct
SEQUENCE: 59
DIVITQTPLS LPVSLGDQAS ISCRSSQTIV HSNGNTYLEW YLQKPGQSPK LLIYKVSNRF      60
SGVPDRFSGS GSGTDFTLKI NRVEAEDLGV YYCFQGSHVP FT                        102

SEQ ID NO: 60           moltype = AA   length = 107
FEATURE                 Location/Qualifiers
REGION                  1..107
                        note = 2D6C3 Heavy Chain Variable Region
source                  1..107
                        mol_type = protein
                        organism = synthetic construct
SEQUENCE: 60
EVMVVESGGG LVKPGGSLKL SCAASGFTFS GYAMSWVRQT PEKRLEWVAT ISSGGTYIYY      60
PDSVKGRFTI SRDNAKNTLY LQMSSLRSED TAMYYCARLG GDNYYEY                   107

SEQ ID NO: 61           moltype = AA   length = 102
FEATURE                 Location/Qualifiers
REGION                  1..102
                        note = 2D6C8 Kappa Chain Variable Region
source                  1..102
                        mol_type = protein
                        organism = synthetic construct
SEQUENCE: 61
DIVITQTPAS LAVSLGQRAT ISYRASKSVS TSGYSYMHWN QQKPGQPPRL LIYLVSNLES      60
GVPARFSGSG SGTDFTLNIH PVEEEDAATY YCQHIRELTR SE                        102

SEQ ID NO: 62           moltype = AA   length = 107
FEATURE                 Location/Qualifiers
REGION                  1..107
                        note = 2D6C8 Heavy Chain Variable Region
source                  1..107
                        mol_type = protein
                        organism = synthetic construct
SEQUENCE: 62
EVMVVESGGG LVKPGGSLKL SCAASGFTFS GYAMSWVRQT PEKRLEWVAT ISSGGTYIYY      60
PDSVKGRFTI SRDNAKNTLY LQMSSLRSED TAMYYCARLG GDNYYEY                   107

SEQ ID NO: 63           moltype = AA   length = 102
FEATURE                 Location/Qualifiers
REGION                  1..102
                        note = 3C2B1 Kappa Chain Variable Region
source                  1..102
                        mol_type = protein
                        organism = synthetic construct
SEQUENCE: 63
DIVLTQSPAS LAVSLGQRAT ISCRASKSIS TSDYNYIHWY QQKPGQPPKL LIYLASNLES      60
GVPARFSGSG SGTDFTLNIH PVEEEDAATY YCQHSRELPL TF                        102

SEQ ID NO: 64           moltype = AA   length = 108
FEATURE                 Location/Qualifiers
```

```
REGION                     1..108
                           note = 3C2B1 Heavy Chain Variable Region
source                     1..108
                           mol_type = protein
                           organism = synthetic construct
SEQUENCE: 64
EVMLVESGGG LVKPGGSLKL SCAASGITFS TYTMSWVRQT PEKRLEWVAT ISTGGDKTYY     60
SDSVKGRFTI SRDNAKNNLY LQMSSLRSED TALYYCARGT TAMYYYAM                 108

SEQ ID NO: 65              moltype = DNA  length = 480
FEATURE                    Location/Qualifiers
misc_feature               1..480
                           note = NM23 P96S C1
source                     1..480
                           mol_type = other DNA
                           organism = synthetic construct
SEQUENCE: 65
atggccaact gtgagcgtac cttcattgcg atcaaaccag atggggtcca gcggggtctt     60
gtgggagaga ttatcaagcg ttttgagcag aaaggattcc gccttgttgg tctgaaattc    120
atgcaagctt ccgaagatct tctcaaggaa cactacgttg acctgaagga ccgtccattc    180
tttgccggcc tggtgaaata catgcactca gggccgtag ttgccatggt ctgggagggg     240
ctgaatgtgg tgaagacggg ccgagtcatg tcgggggaca ccaactctgc agactccaag    300
cctgggacca tccgtggaga cttctgcata caagttggca ggaacattat acatggcagt    360
gattctgtgg agagtgcaga gaaggagatc ggcttgtggt tccaccctga ggaactggta    420
gattacacga gctgtgctca gaactggatc tataccggtc accaccacca ccaccactga    480

SEQ ID NO: 66              moltype = AA  length = 159
FEATURE                    Location/Qualifiers
REGION                     1..159
                           note = NM23 P96S C1
source                     1..159
                           mol_type = protein
                           organism = synthetic construct
SEQUENCE: 66
MANCERTFIA IKPDGVQRGL VGEIIKRFEQ KGFRLVGLKF MQASEDLLKE HYVDLKDRPF     60
FAGLVKYMHS GPVVAMVWEG LNVVKTGRVM LGETNSADSK PGTIRGDFCI QVGRNIIHGS    120
DSVESAEKEI GLWFHPEELV DYTSCAQNWI YTGHHHHHH                           159
```